United States Patent
Steidler et al.

(10) Patent No.: US 12,252,516 B2
(45) Date of Patent: *Mar. 18, 2025

(54) MUCOADHESIVE MICROORGANISM

(71) Applicant: INTREXON ACTOBIOTICS N.V., Zwijnaarde (BE)

(72) Inventors: Lothar Steidler, Lokeren (BE); Klaas Vandenbroucke, De Pinte (BE)

(73) Assignee: INTREXON ACTOBIOTICS N.V., Zwijnaarde (BE)

( * ) Notice: Subject to any disclaimer, the term of this patent is extended or adjusted under 35 U.S.C. 154(b) by 246 days.

This patent is subject to a terminal disclaimer.

(21) Appl. No.: 17/832,745

(22) Filed: Jun. 6, 2022

(65) Prior Publication Data

US 2023/0013523 A1    Jan. 19, 2023

Related U.S. Application Data

(60) Continuation of application No. 17/026,379, filed on Sep. 21, 2020, now Pat. No. 11,384,123, which is a division of application No. 16/331,660, filed as application No. PCT/IB2017/055470 on Sep. 11, 2017, now Pat. No. 10,808,014.

(60) Provisional application No. 62/394,024, filed on Sep. 13, 2016.

(51) Int. Cl.
| | |
|---|---|
| C07K 14/335 | (2006.01) |
| A61K 35/74 | (2015.01) |
| A61K 35/741 | (2015.01) |
| A61P 3/10 | (2006.01) |
| C07K 14/435 | (2006.01) |
| C07K 14/575 | (2006.01) |
| C12N 9/88 | (2006.01) |
| A61K 35/00 | (2006.01) |
| A61K 39/00 | (2006.01) |

(52) U.S. Cl.
CPC ............ *C07K 14/335* (2013.01); *A61K 35/74* (2013.01); *A61K 35/741* (2013.01); *A61P 3/10* (2018.01); *C07K 14/435* (2013.01); *C07K 14/575* (2013.01); *C12N 9/88* (2013.01); *A61K 2035/115* (2013.01); *A61K 39/00* (2013.01); *C07K 2319/00* (2013.01); *C07K 2319/036* (2013.01)

(58) Field of Classification Search
CPC ..... C07K 14/335; C07K 2319/00; A61P 3/10; A61P 3/00; A61K 35/741
See application file for complete search history.

(56) References Cited

U.S. PATENT DOCUMENTS

| | | | |
|---|---|---|---|
| 4,919,918 A | 4/1990 | Cole et al. | |
| 5,223,285 A | 6/1993 | DeMichele et al. | |
| 5,470,561 A | 11/1995 | Klugkist et al. | |
| 5,695,746 A | 12/1997 | Garlick, Jr. et al. | |
| 5,700,782 A | 12/1997 | Cope et al. | |
| 5,869,118 A | 2/1999 | Morris et al. | |
| 5,972,685 A | 10/1999 | Beitz et al. | |
| 5,993,785 A | 11/1999 | Johansen et al. | |
| 6,117,417 A | 9/2000 | Wicks et al. | |
| 6,165,494 A | 12/2000 | Picciano | |
| 6,171,611 B1 | 1/2001 | Picciano | |
| 6,348,187 B1 | 2/2002 | Pan et al. | |
| 6,387,352 B1 | 5/2002 | Johansen et al. | |
| 8,759,088 B2 | 6/2014 | Steidler et al. | |
| 9,200,249 B2 | 12/2015 | Remaut et al. | |
| 10,808,014 B2 * | 10/2020 | Steidler ................ | A61K 35/741 |
| 11,384,123 B2 * | 7/2022 | Steidler ................ | C07K 14/575 |
| 2002/0044910 A1 | 4/2002 | Johansen et al. | |
| 2003/0152530 A1 | 8/2003 | Johansen et al. | |
| 2004/0076590 A1 | 4/2004 | Wilkins | |
| 2010/0178273 A1 | 7/2010 | Rottiers | |

(Continued)

FOREIGN PATENT DOCUMENTS

| | | |
|---|---|---|
| CN | 103131725 A | 6/2013 |
| GB | 227835 A | 4/1925 |

(Continued)

OTHER PUBLICATIONS

Batchelor, H.K. et al., "An in vitro mucosal model for prediction of the bioadhesion of alginate solutions to the oesophagus," Int. J. Pharm., 238 (2002) 123-132.

(Continued)

*Primary Examiner* — Mary Maille Lyons

(74) *Attorney, Agent, or Firm* — BANNER & WITCOFF, LTD.

(57) ABSTRACT

The present disclosure provides genetically modified microorganisms (e.g., bacteria or yeast) with enhanced mucin-binding and/or cell-adhesion properties. For example, the present disclosure provides bacteria exhibiting increased in vitro binding to Caco-2 cells, and increased in vitro binding to mucins. Such microorganisms (e.g., bacteria) can be used, e.g., to deliver bioactive polypeptides to the gastrointestinal tract of a mammalian subject. Modifying the microorganism in the described manner allows for the modulation of gastrointestinal retention and transit times for the microorganism (e.g., bacterium). Exemplary microorganisms (e.g., lactic acid bacteria, such as *Lactococcus lactis*) contain an exogenous nucleic acid encoding a fusion protein containing a cell-adherence polypeptide, such as CmbA, and a mucin-binding polypeptide, such as a trefoil factor (TFF), e.g., human TFF3. The current disclosure further provides method for making and using the described microorganisms (e.g., bacteria).

22 Claims, 14 Drawing Sheets

Specification includes a Sequence Listing.

(56) References Cited

U.S. PATENT DOCUMENTS

| | | |
|---|---|---|
| 2012/0039853 A1 | 2/2012 | Corveleyn et al. |
| 2014/0105863 A1 | 4/2014 | Vanden-Broucke et al. |
| 2014/0234371 A1 | 8/2014 | Steidler et al. |

FOREIGN PATENT DOCUMENTS

| | | |
|---|---|---|
| JP | 2006-503545 A | 2/2006 |
| JP | 2009-539769 A | 11/2009 |
| JP | 2014-518634 A | 8/2014 |
| RU | 2583579 C2 | 5/2016 |
| TW | 201529847 A | 8/2015 |
| WO | WO-93/17117 | 9/1993 |
| WO | WO-96/32487 A1 | 10/1996 |
| WO | WO-99/47657 A2 | 9/1999 |
| WO | WO-2000/18377 | 4/2000 |
| WO | WO-2000/22909 | 4/2000 |
| WO | WO-01/02570 A1 | 1/2001 |
| WO | WO-02/090551 A2 | 11/2002 |
| WO | WO-2002102403 A1 | 12/2002 |
| WO | WO-03/068934 A2 | 8/2003 |
| WO | WO-2005/090396 A1 | 9/2005 |
| WO | WO-2007/025977 A2 | 3/2007 |
| WO | WO-2007/063075 A1 | 6/2007 |
| WO | WO-2007/143212 A1 | 12/2007 |
| WO | WO-2008/090223 A2 | 7/2008 |
| WO | WO-2010/086512 A2 | 8/2010 |
| WO | WO-2012/164083 A1 | 12/2012 |
| WO | WO-2012/168473 A2 | 12/2012 |
| WO | WO-2013/041673 A1 | 3/2013 |
| WO | WO-2014/066945 A1 | 5/2014 |
| WO | WO-2016/124239 A1 | 8/2016 |
| WO | WO-2017/122180 A1 | 7/2017 |
| WO | WO-2018/042390 A1 | 3/2018 |

OTHER PUBLICATIONS

Boekhorst, Jos et al., "Comparative analysis of proteins with a mucus binding domain found exclusively in lactic acid bacteria," *Microbiology* 2006, 152(1):273-280.

Braat, Henri et al., "A Phase I Trial with Transgenic Bacteria Expressing Interluekin-10 in Crohn's Disease," Clin. Gastroenterol. and Hepatol. 2006, 4(6):754-759.

Bruschi M. L. and de Freitas O., "Oral Bioadhesive Drug Delivery Systems," *Drug Development and Industrial Pharmacy*, 2005 31:293-310.

Caluwaerts, S. et al., "AG013, a mouth rinse formulation of Lactococcus lactis secreting human Trefoil Factor 1, provides a safe and efficacious therapeutic tool for treating oral mucositis," *Oral. Oncol.* 2010, 46:564-570.

Chang et al., "A new theory of enterorecirculation of amino acids and its use for depleting unwanted amino acids using oral enzyme-artificial cells, as in removing phenylalanine in phenylketonuria." *Artif. Cells Blood Substit. Immobil. Biotechnol.* 1995, 23(1):1-21.

Conlon et al., "Host-defense and trefoil factor family peptides in skin secretions of the Mawa clawed frog *Xenopus boumbaensis* (Pipidae)," *Peptides* 2015, 72:44-49.

Etzold, Sebrina et al., "Structural basis for adaptation of lactobacilli to gastrointestinal mucus," Environmental Microbiology (2014) 16(3), 888-903.

Fujita et al., "Molecular cloning and characterization of three distinct choriogenins in masu salmon, *Oncorhynchus masou*," Mol. Reprod. Dev. 2008, 75(7):1217-1228.

Gasson, M.J., "Plasmid Complements of *Streptococcus lactis* NCDO 712 and Other Lactic Streptococci After Protoplast-Induces Curing," 1983, *J. Bacteriol.* vol. 154, No. 1, pp. 1-9.

Gazzaniga et al., "Oral delayed release system for colonic specific delivery," *Int. J. Pharm.* (1994) 108:77-83.

Glenting et al., "A Plasmid Selection in *Lactococcus lactis* and Its Use for Gene Expression in *L. lactis* and Huma Kidney Fibroblasts," (2002) 68:5051-5056.

Harwood and Cutting, "Molecular Biological Methods for *Bacillus*," John Wiley & Co. 1990, pp. 341-344.

Hsueh, et al. "Increase of the adhesion ability and display of a rumen fungal xylanase on the cell surface of *Lactobacilus casei* by using a listerial cell-wall-anchoring protein," Journal of the Science of Food and Agriculture, vol. 94, No. 3, Jul. 31, 2013, pp. 576-584.

Law, Jean et al., "A System To Generate Chromosomal Mutations in *Lactococcus lactis* Which Allows Fast Analysis of Targeted Genes," J. Bacteriol. 1995, 177(24):7011-7018.

Jensen, Hanne et al., "Role of *Lactobacillus reuteri* cell and mucus-binding protein A (CmbA) in adhesion to intestinal epithelial cells and mucus in vitro," *Microbiology* 2014, 160(4):671-681.

Long, Anna E. et al., "Humoral Responses to Islet Antigen-2 and Zinc Transporter 8 Are Attenuated in Patients Carrying *HLA-A*24* Alleles at the Onset of Type 1 Diabetes," *Diabetes* 2013, 62 (6), 2067-2071.

Lukic, Jovanka et al., "Different Roles for Lactococcal Aggregation Factor and Mucin Binding Protein in Adhesion to Gastrointestinal Mucosa," *Appl. Environ. Microbiol.* 2012, 78(22):7993-8000.

Miyoshi, Yukihiro et al., "A Mucus Adhesion Promoting Protein, MapA, Mediates the Adhesion of *Lactobacillus reuteri* to Caco-2 Human Intestinal Epithelial Cells," Biosci. Biotechnol. Biochem., 70(7), 2006, 1622-1628.

Rapoport, Georges et al., "Gene Expression Using Bacillus," Current Opinion in Biotechnology 1990, 1:21-27.

Robert S. and Steidler L., "Recombinant *Lactococcus lactis* can make the difference in antigen-specific immune tolerance induction, the Type 1 Diabetes case," Microb. Cell Fact. 2014, 13 Suppl. 1: S11.

Rondas, Dieter et al., "Citrullinated Glucose-Regulated Protein 78 Is an Autoantigen in Type 1 Diabetes," *Diabetes* 2015; 64(2):573-586.

Sarkissian, C. N. et al., "Preclinical evaluation of multiple species of PEGylated recombinant phenylalanine ammonia lyase for the treatment of phenylketonuria," Proc. Natl. Acad. Sci. USA 2008, 105:20894-20899.

Sarkissian, C. N. et al., "A different approach to treatment of phenylketonuria: Phenylalanine degradation with recombinant phenylalanine ammonia lyase," Proc. Natl. Acad. Sci. USA 1999, 96: 2339-2344.

Sorensen et al. (2000) Appl. Environ. Microbiol. 66:1253-1258.

Steidler et al., Science 2000; 289(5483): 1352-1355.

Steidler et al., *Appl. Environ. Microbiol.* 1998, 64(1):342-5.

Steidler, L., et al., Nat. Biotechnol. 2003, 21(7): 785-789.

Strobel et al., "Immunological responses to fed protein antigens in mice," Immunology. Jul. 1983;49(3):451-6.

Termont, S. et al., "Intracellular Accumulation of Trehalose Protects *Lactococcus lactis* from Freeze-Drying Damage and Bile Toxicity and Increases Gastric Acid Resistance," *Appl. Environ. Microbiol.* 2006, 72: 7694-7700.

Tomasetto et al., "pS2/TFF1 Interacts Directly Wih the VWFC Cysteine-Rich Domains of Mucins," *Gastroenterology* 2000, 118(1):70-80.

Van Asseldonk et al., "Functional analysis of the Lactococcus lactis usp45 secretion signal in the secretion of a homologous proteinase and a heterologous a-amylase," Mol. Gen. Genet. 1993, 240:428-434.

Von Ossowski, Ingemar et al., "Functional Characterization of a Mucus-Specific LPXTG Surface Adhesin from Probiotic *Lactobacillus rhamnosus* GG," Applied and Environmental Microbilology, Jul. 2011, pp. 4465-4472.

Waterfield, N R, Lepage, R W F, Wilson, P W, et al. (1995), "The isolation of lactococcal promoters and their use in investigating bacterial luciferase synthesis in Lactococcus lactis" Gene 165(1):9-15.

Ye et al., "*Grp 78* Heterozygosity Promotes Adaptive Unfolded Protein Response and Attenuates Diet-Induced Obesity and Insulin Resistance," Diabetes 2010, 59(1):6-16.

International Search Report and Written Opinion mailed Jan. 10, 2018 for PCT/IP2017/055470.

Jensen et al., Microbiology (Reading, England), (Apr. 2014) vol. 160, No. Pt 4, pp. 671-681. (Year: 2014).

(56) References Cited

OTHER PUBLICATIONS

Vandenbroucke, K., de Haard, H., Beirnaert, E. et al. Orally administered *L. lactis* secreting an anti-TNF Nanobody demonstrate efficacy in chronic colitis. Mucosal Immunol 3, 49-56 (2010).
MacKenzie DA, Tailford LE, Hemmings AM, Juge N.. Crystal structure of a mucus-binding protein repeat reveals an unexpected functional immunoglobulin binding activity. J Biol Chem 284: 32444-32453.
Rojas M, Ascencio F, Conway PL. Purification and characterization of a surface protein from Lactobacillus fermentum 104R that binds to porcine small intestinal mucus and gastric mucin. *Appl Environ Microbiol.* 2002;68(5):2330-2336.
Roos, S. and Jonsson, H. (2002) A high molecular-mass cell-surface protein from *Lactobacillus reuteri* 1063 adheres to mucus components. Microbiology, 148, 433-442.
Vandenbroucke, Klaas et al. "Active delivery of trefoil factors by genetically modified Lactococcus lactis prevents and heals acute colitis in mice." Gastroenterology 127 2 (2004): 502-13.
Taupin, D., & Podolsky, D. K. (2003). Trefoil factors: Initiators of mucosal healing. Nature Reviews Molecular Cell Biology, 4(9), 721-732.
Van Tassell ML, Miller MJ. Lactobacillus adhesion to mucus. Nutrients. 2011;3(5):613-636.
Van Asseldonk MV, Rutten G, Oteman M, Siezen RJ, de Vos WM, Simons G. 1990. Cloning of usp45, a gene encoding a secreted protein from Lactococcus lactis subsp. lactis MG1363. Gene 95:155-160.
Mercier-Bonin M and Chapot-Chartier M-P (2017) Surface Proteins of Lactococcus lactis: Bacterial Resources for Muco-adhesion in the Gastrointestinal Tract. Front. Microbiol. 8:2247.
Le DT, Tran TL, Duviau MP, et al. Unraveling the role of surface mucus-binding protein and pili in muco-adhesion of Lactococcus lactis. *PLoS One.* 2013; 8(11): e79850. Published Nov. 18, 2013.
Mays ZJS, Chappell TC, Nair NU. Quantifying and Engineering Mucus Adhesion of Probiotics. ACS Synth Biol. 2020;9(2):356-367.
Radziwill-Bienkowska JM, Le DT, Szczesny P, et al. Adhesion of the genome-sequenced *Lactococcus lactis* subsp. cremoris IBB477 strain is mediated by specific molecular determinants. Appl Microbiol Biotechnol. 2016;100(22):9605-9617.
Radziwill-Bienkowska JM, Robert V, Drabot K, et al. Contribution of plasmid-encoded peptidase S8 (PrtP) to adhesion and transit in the gut of *Lactococcus lactis* IBB477 strain. Appl Microbiol Biotechnol. 2017;101(14):5709-5721.
Zhang, B., Zuo, F., Yu, R et al. Comparative genome-based identification of a cell wall-anchored protein from Lactobacillus plantarum increases adhesion of Lactococcus lactis to human epithelial cells. Sci Rep 5, 14109 (2015).
Nishiyama K, Sugiyama M, Mukai T. Adhesion Properties of Lactic Acid Bacteria on Intestinal Mucin. *Microorganisms*. 2016;4(3):34. Published Sep. 2, 20160.
Newton JL, Allen A, Westley BR, May FE. The human trefoil peptide, TFF1, is present in different molecular forms that are intimately associated with mucus in normal stomach. Gut. 2000;46(3):312-320.
Hoffmann W. TFF2, a MUC6-binding lectin stabilizing the gastric mucus barrier and more (Review). Int J Oncol. 2015;47(3):806-816.
Ruchaud-Sparagano MH, Westley BR, May FE. The trefoil protein TFF1 is bound to MUC5AC in human gastric mucosa. *Cell Mol Life Sci.* 2004;61(15):1946-1954.
Wright NA. Interaction of trefoil family factors with mucins: clues to their mechanism of action ?. *Gut.* 2001;48(3):293-294.
Wiede A, Jagla W, Welte T, Kohnlein T, Busk H, Hoffmann W. Localization of TFF3, a new mucus-associated peptide of the human respiratory tract. Am J Respir Crit Care Med. 1999;159(4 Pt 1):1330-1335.
Jacobitz AW, Kattke MD, Wereszczynski J, Clubb RT. Sortase Transpeptidases: Structural Biology and Catalytic Mechanism. Adv Protein Chem Struct Biol. 2017;109:223-264.
Bradshaw WJ, Davies AH, Chambers CJ, Roberts AK, Shone CC, Acharya KR. Molecular features of the sortase enzyme family. *FEBS J.* 2015;282(11):2097-2114.
Russian Office Action issued in Russian patent application No. 2019108553, dated Dec. 15, 2020.
Russian Office Action issued in Russian patent application No. 2019108553, dated May 14, 2021.
Hughes J. et al., "Precipitation of Autoimmune Diabetes With anti-PD-1 Immunotherapy, Diabetes Care", Apr. 2015, vol. 38, pp. e55-e57.
Japan Office Action issued in Japan patent application No. 2019-513897, dated May 25, 2021.
Apr. 28, 2023 (IN) First Examination Report Application No. 201917009525.

\* cited by examiner

```
  1  atgaaaaaaa agattatctc agctatttta atgtctacag tgatactttc tgctgcagcc
      m  k  k   r  l  s    a  i  l   m  s  t    v  i  l   s  a  a  a
      >.........SSusp45...................................>>

61  ccgttgtcag gtgtttacgc cgaagaatac gttggtcttt cagctaacca atgtgctgtt
      p  l  s   g  v  y    a  e  e   y  v  g  l  s  a  n   q  c  a  v
      >..........................hTFF3..................................>

121  ccagctaaag atcgtgttga ttgtggttac ccacacgtta ctccaaaaga atgtaacaac
      p  a  k   d  r  v   d  c  g  y  p  h  v   t  p  k   e  c  n  n
      >...........................hTFF3..................................>

181  cgtggtgtt gtttgatt acgtatccca ggtgttccat ggtgttttaa accacttcaa
      r  g  c  f  d   s  r  i   p  g  v  p   w  c  f  k   p  l  q
      >...........................hTFF3..................................>

241  gaagctgaat gtacttttta a
      e  a  e   c  t  f   -
      >.........hTFF3......>>
```

```
641  ctaatgatga gttagaaatt aaagcaacag atccgactaa ttatccaaac tgtggcgatg tgtatggcc attatttgaa
     a  n  d  e  l  e  i   k  a  t   d  p  t   n  y  p  n   c  g  d   v  y  g   p  l  f  e
     >...                                                                                 cmbA 721  ttggatgcta gcggaacagct tgttaataaa gatgaagtta tatctcttaa agatatgtat attttccaaa tattgaatt
     l  d  a   s  g  q   l  v  n  k   d  e  v   i  s  l   k  d  m  y   i  f  q   i  l  k
     >...                                                                                 cmbA 801  agtaaataca aaagatagtg actttccaata tgtaatatta acaatgaatc gtaaagatac tgcagatagg tctgtatatc
     i  v  n  t   k  d  s   d  f  q   y  v  i  l   t  m  n   r  k  d   t  a  d  r   s  v  y
     >...                                                                                 cmbA 881  tttttgtaac tggaagcaat tatagtaatg ctgttgttgt taaagtaaag ccaaatgatc cttatgaatt aagtaaaact
     l  f  v  t   g  s  n   y  s  n   a  v  v   k  v  k   p  n  d   t  y  e   l  s  k  t
     >...                                                                                 cmbA 961  ggatatagtg ttacttatac agaaccaaca actataaatg gacattatgt tgatggaact tttatggtta caggaagtac
     g  y  s   v  t  y  t   e  p  t   t  i  n   g  h  y   v  d  g  t   f  y  v   t  g  s
     >...                                                                                 cmbA 1041 ttacgatgat ggttttataa tgccagattg gcaactgcag cacctteaga ttatatatag tttaggaaat tatgatccaa
     t  y  d  d   g  f  i   m  p  d  w   q  l  q   h  l  q   i  y  i  s   l  g  n   y  d  p
     >...                                                                                 cmbA 1121 gcaatactga cgcaaccatca gtttgtgaaa taatgccaag gtaccggtaa gttaaagatatag tggagtacct
     s  n  t   d  a  t  s   v  c  e   i  m  p  s   y  e  k   v  p  v   i  k  y   s  g  v  p
     >...                                                                                 cmbA 1201 tcaaatatta gccaacctaa ggtttacaatt acgggttta cgggtcaaga gttaacgtt acagatatta ttaacaatta
     s  n  i   a  q  p   k  v  y  i   t  g  f   t  g  q   e  f  n  v   t  d  i   i  n  n
     >...                                                                                 cmbA 1281 taagaaagtt tttaaggct actatcattca aaatcctaat gtggcgtcca tggaactct ttcccaattt gaggaatgtg
     y  k  k  v   f  k  g   y  y  i   q  n  p  n   v  a  s   m  g  t   i  s  q  f   e  n  g
     >...                                                                                 cmbA
```

FIG. 5B

```
1361  gttattactt aaagacatat tatgataatg atggtaatgt tgactttaag ggcttgtatc atcaaattga tgatcagyga
      g  y  y  l  k  t  y  y  d  n  d  g  n  v  d  f  k  g  l  y  h  q  i  d  d  q  g
      >..........cmbA..........................................................................

1441  acaatgagtg tgagtgttct taatgcagat aataaaacaa ttgttggacc tgaaaatatt cttgctggta aatgcataa
      t  m  s  v  s  v  l  n  a  d  n  k  t  i  v  g  p  e  n  i  l  a  g  k  s  h
      >..........cmbA..........................................................................

1521  ctttaacttt aatgtcata actggattgc gcggaatcct tatgtcacta gttcagctca cgaagtcata ttaaagtatg
      n  f  n  f  n  g  h  n  w  i  a  r  n  p  y  v  t  s  s  a  h  e  v  i  l  k  y
      >..........cmbA..........................................................................

1601  ctaagttagg ttcagttatt cctgttgatg aaaacggaaa taaaataaac gatggattgc aatatgttaa tgatccagat
      a  k  l  g  s  v  i  p  v  d  e  n  g  n  k  i  n  d  g  w  q  y  v  n  d  p  d
      >..........cmbA..........................................................................

1681  gatgcttcca aagccactag cccatatgaa aaagcgccag ttatgtgatgg ttatgtagct gtaaatccag atgaaacgat
      d  a  s  k  a  t  s  p  y  e  k  a  p  v  i  d  g  y  v  a  v  n  p  d  e  t
      >..........cmbA..........................................................................

1761  cgttcttcct cataacttaa gtagtgacac aaagatttat taccgaaaga ggattaaaagt taccatatagt ggtagtgaca
      i  v  l  p  h  n  l  s  s  d  t  k  i  y  y  r  k  v  i  k  v  t  y  s  g  s  d
      >..........cmbA..........................................................................

1841  gcaagaccta cgatggtaac ccagctaact tcgagccaac gacagttcag tggagtggct tgaaaggact gaacacttca
      s  k  y  d  g  n  p  a  n  f  e  p  t  t  v  q  w  s  g  l  k  g  l  n  t  s
      >..........cmbA..........................................................................

1921  acctaacgt ccgctgactt cacgtggaat actgcggata agaaggcacc aacggatgcc ggtaagtaca cacttagttt
      t  l  t  s  a  d  f  t  w  n  t  a  d  k  k  a  p  t  d  a  g  k  y  t  l  s
      >..........cmbA..........................................................................

2001  gaatacgacc ggagaagcag ccttaacgtaa ggctaacccg aactatgatc tcaagacaat tagcggtagt tacaacctaca
      l  n  t  g  e  a  a  l  r  k  a  n  p  n  y  d  l  k  t  i  s  g  s  y  t  y
      >..........cmbA..........................................................................
```

FIG. 5C

```
2081  cgattaatcc actaggggatt gtgactgtaa attacaaggg ctatgataag aaagtctatg atggtcaaac tggaacgatt
       t  i  n  p  l  g  i  v  t  v  n  y  k  g  y  d  k  k  v  y  d  g  g  p  g  t  i
      >.........................................................................cmbA..........>

2161  aatccgggta aattaacgtg gagtaagttg ccagatggta cttcattgaa gatgccaaca tggagtatag atgatttcgc
       n  p  g  k  i  t  w  s  k  l  p  d  g  t  s  l  k  m  p  t  w  s  i  d  d  f
      >.........................................................................cmbA..........>

2241  ttgggaaaca gctgatggct tagcaccaaa ggcagtagga acttatcgga ttatcttgac ggatgctggt aaggctgcac
       w  e  t  a  d  g  l  a  p  t  a  v  g  t  y  r  i  i  l  t  d  a  g  k  a  a
      >.........................................................................cmbA..........>

2321  tcaagaagat taatccaaat tatgacttaa gcagtattac tggtgtcttt acttatgaaa ttaagccagc acagacacca
       l  k  k  i  n  p  n  y  d  l  s  s  i  t  g  v  f  t  y  e  i  k  p  a  q  t  p
      >.........................................................................cmbA..........>

2401  gaaatcttag gccaaacacc tgagcaacca ccaggccaaa atactaatca atcaaggagc gaaaacggct ttggttcttc
       e  i  l  g  q  t  p  e  q  p  p  g  q  n  t  n  q  s  g  a  e  n  g  f  g  s
      >.........................................................................cmbA..........>

2481  tacaaggcct aatgcatcaa ctaactccaa tcttaatcaa cttccacaga ctggtaatga gcattctaat actgcacttg
       s  t  r  p  n  a  s  t  n  s  n  l  n  q  l  p  q  t  g  n  e  h  s  n  t  a  l
      >.........................................................................cmbA..........>

2561  ctggtctagc attggctttc ttgactgcta tgcttggttt gggcaagaag cgtaaacatg attaa
       a  g  l  a  l  a  f  l  t  a  m  l  g  l  g  k  k  r  k  h  d  -
      >.........................................................................cmbA..........>>
```

FIG. 5D

MUCOADHESIVE MICROORGANISM

CROSS REFERENCE TO RELATED APPLICATIONS

This application is a continuation of U.S. patent application Ser. No. 17/026,379, filed Sep. 21, 2020, which is a division of U.S. patent application Ser. No. 16/331,660, filed Mar. 8, 2019, now U.S. Pat. No. 10,808,014, issued Oct. 20, 2020, which is the national phase entry of International Application No. PCT/IB2017/055470, filed Sep. 11, 2017, and claims benefit of the filing date of U.S. Provisional Application No. 62/394,024, filed Sep. 13, 2016, the disclosure of each of which is hereby incorporated herein by this reference in its entirety.

REFERENCE TO SEQUENCE LISTING

The instant application contains a Sequence Listing which has been submitted electronically in ASCII format via EFS-WEB and is hereby incorporated by reference in its entirety. Said ASCII copy, created on Apr. 18, 2022, is named 205350-0031-02-US-000040-SL.txt and is 75,358 bytes in size.

BACKGROUND

Genetically modified microorganisms (e.g., bacteria) have been used to deliver therapeutic molecules to mucosal tissues. See, e.g., Steidler, L., et al., *Nat. Biotechnol.* 2003, 21(7): 785-789; Robert S. and Steidler L., *Microb. Cell Fact.* 2014, 13 Suppl. 1: S11; Braat et al., *Clin. Gastroenterol. Hepatol.* 2006, 4(6):754-759; and Steidler et al., *Science* 2000, 289(5483):1352-1355.

There is a need in the art for microbial (e.g., bacterial) strains with improved pharmacokinetic and pharmacodynamics properties, and a need for efficacious, targeted, and controlled methods for the treatment of various diseases treatable with such genetically modified bacteria. The present disclosure addresses these needs.

BRIEF SUMMARY

The present disclosure provides microorganisms (e.g., bacteria or yeast) with enhanced cell-adhesion and/or mucin-binding properties. For example, the present disclosure provides bacteria exhibiting increased in vitro binding to Caco-2 cells, and increased in vitro binding to mucins. Such microorganisms (e.g., bacteria) can be used, e.g., to deliver bioactive polypeptides to the gastrointestinal tract of a mammalian subject, while the described genetic modifications allow for the modulation of gastrointestinal retention and transit times of the microorganism (e.g., bacterium). The described technology allows for the modulation of pharmacokinetic and pharmacodynamic properties of the bioactive polypeptides expressed by the microorganism (e.g., bacterium). For example, expression, secretion and anchoring of a fusion protein containing a trefoil factor (TFF) and a cell-adhesion polypeptide, such as CmbA (see, e.g., Jensen et al., *Microbiology* 2014, 160(4):671-681) (e.g., TFF3-CmbA) in the cell wall of a lactic acid bacterium (LAB), such as *Lactococcus lactis*, enables adherence of the bacterium to intestinal epithelial cells, and further enables binding of the bacterium to mucins.

Compositions

In some aspects, the present disclosure provides microorganisms (e.g., a bacteria or yeast) comprising an exogenous nucleic acid encoding a fusion protein comprising a cell-adherence polypeptide. In some examples, the current disclosure provides a microorganism (e.g., bacterium or yeast) comprising an exogenous nucleic acid encoding a fusion protein, wherein the exogenous nucleic acid encoding the fusion protein contains a sequence encoding a cell-adherence polypeptide. In some examples, the cell-adherence polypeptide is selected from the group consisting of cell and mucus-binding protein A (CmbA) (see, e.g., Jensen et al., *Microbiology* 2014, 160(4):671-681), mucus binding protein or mub domain proteins (Mub) (see, e.g., Boekhorst et al., *Microbiology* 2006, 152(1):273-280), mucus adhesion promoting protein (MapA) (see, e.g., Miyoshi et al., *Biosci. Biotechnol. Biochem.* 2006, 70(7):1622-8), lactococcal mucin binding protein (MbpL) (see, e.g., Lukić et al., *Appl. Environ. Microbiol.* 2012, 78(22):7993-8000). A cell-wall anchoring peptide, such as *Staphylococcus aureus* protein A anchor fragment (SpaX) may be added (see, e.g., Steidler et al., *Appl. Environ. Microbiol.* 1998, 64(1):342-5). In some examples, the current disclosure provides a microorganism (e.g., bacterium or yeast) comprising an exogenous nucleic acid encoding a fusion protein, wherein the fusion protein includes a CmbA polypeptide. In some examples, the CmbA polypeptide is CmbA from *Lactobacillus reuteri*. See, e.g., ATCC PTA6474, e.g., as disclosed in Jensen et al., supra. In some examples according to any of the above embodiments, the cell-adherence polypeptide is a CmbA polypeptide having an amino acid sequence that is at least 90%, at least 92%, at least 95%, at least 96%, at least 97%, at least 98%, or at least 99% identical to SEQ ID NO: 1. In other examples according to any of the above embodiments, the cell-adherence polypeptide is a CmbA polypeptide encoded by an exogenous nucleic acid sequence that is at least 90%, at least 92%, at least 95%, at least 96%, at least 97%, at least 98%, or at least 99% identical to SEQ ID NO: 2.

In other examples according to any of the above embodiments, the fusion protein comprises a mucin-binding polypeptide, such as a trefoil factor (TFF) polypeptide (e.g., TFF1, TFF2, or TFF3) or a MucBP polypeptide (see, e.g., Lukic et al, *Appl. Environ. Microbiol.* 2012, 78(22):7993-8000). Thus, in some examples, the current disclosure provides a microorganism (e.g., a bacterium or yeast) comprising an exogenous nucleic acid encoding a fusion protein, wherein the fusion protein contains a cell-adherence polypeptide (e.g., a CmbA polypeptide) and a mucin-binding polypeptide (e.g., a TFF polypeptide). In some examples, the TFF polypeptide is a human TFF polypeptide (e.g., hTFF1, hTFF2, or hTFF3). In some examples according to any of the above embodiments, the mucin-binding polypeptide is a human TFF3 polypeptide having an amino acid sequence that is at least 90%, at least 92%, at least 95%, at least 96%, at least 97%, at least 98%, or at least 99% identical to SEQ ID NO: 3. In other examples according to any of the above embodiments, the mucin-binding polypeptide is a human TFF3 polypeptide encoded by an exogenous nucleic acid sequence that is at least 90%, at least 92%, at least 95%, at least 96%, at least 97%, at least 98%, or at least 99% identical to SEQ ID NO: 4. In some examples, the TFF polypeptide is a mammalian TFF polypeptide, such as a cow, pig, sheep, dog, cat, or horse TFF. In further examples, the TFF is an amphibian TFF. Exemplary TFF polypeptides are disclosed, e.g., in Conlon et al., *Peptides* 2015, 72:44-49, and cited references therein, each of the disclosures are incorporated herein by reference in their entirety. In other examples, the TFF polypeptide is a trefoil-like domain. Exemplary polypeptides according to this embodiment are disclosed in Fujita et al., *Mol. Reprod. Dev.* 2006, 75(7): 1217-1228, the disclosure of which is incorporated herein by reference in its entirety.

In some examples according to any of the above embodiments, the current disclosure provides a bacterium (e.g., a lactic acid bacterium, such as *Lactococcus lactis*) comprising an exogenous nucleic acid encoding a fusion protein comprising (1) a mucin-binding polypeptide selected from a TFF polypeptide (e.g., human TFF1, human TFF2, or human TFF3) and a MucBP polypeptide; and (2) a cell-adherence polypeptide selected from a CmbA polypeptide, a Mub polypeptide, a MapA polypeptide, an MbpL polypeptide, and a SpaX polypeptide. In some examples according to this embodiment, the fusion protein contains a CmbA polypeptide (e.g., *Lactobacillus reuteri* CmbA) and a TFF polypeptide (e.g., human TFF1, human TFF2, or human TFF3).

In some examples according to any of the above embodiments, the exogenous nucleic acid encoding the fusion protein is integrated into the chromosome of the microorganism, e.g., the chromosome of a bacterium. In some examples, the exogenous nucleic acid encoding the fusion protein is constitutively expressed in the microorganism (e.g., bacterium). In other examples, the exogenous nucleic acid encoding the fusion protein is located on a plasmid.

In some examples according to any of the above embodiments, the fusion protein is expressed by the microorganism (e.g., bacterium). In other examples the fusion protein is anchored in the cell wall of the microorganism (e.g., bacterium). For example, the fusion protein is displayed on the surface (i.e., outer membrane) of the microorganism (e.g., bacterium).

In some examples according to any of the above embodiments, the exogenous nucleic acid encoding a fusion protein further includes a secretion leader sequence encoding a secretion signal peptide. In some examples, the secretion leader sequence contains a nucleotide sequence encoding a secretion leader of unidentified secreted 45-kDa protein (Usp45). Such secretion leader sequence or peptide is referred to herein as SSusp45. In some examples, SSusp45 has an amino acid sequence that is at least 90%, at least 92%, at least 95%, at least 96%, at least 97%, at least 98%, or at least 99% identical to SEQ ID NO: 5. In other examples, SSusp45 is encoded by a nucleic acid sequence that is at least 90%, at least 92%, at least 95%, at least 96%, at least 97%, at least 98%, or at least 99% identical to SEQ ID NO: 6 or SEQ ID NO: 7. Any secretion leader sequence derived from a gram-positive bacterium, e.g., any secretion leader sequence derived from *Lactococcus lactis* is useful in the context of the above embodiments. In further examples according to any of the above embodiments, the secretion signal peptide (e.g., SSusp45) is bound to the mucin-binding polypeptide, such as such as a TFF polypeptide. In some examples according to this embodiment, SSusp45 is bound to a human TFF polypeptide. For examples, the fusion protein may include an amino acid sequence that is at least 90%, at least 92%, at least 95%, at least 96%, at least 97%, at least 98%, or at least 99% identical to SEQ ID NO: 8. In other examples, the fusion protein may be encoded by an exogenous nucleic acid sequence containing a sequence that is at least 90%, at least 92%, at least 95%, at least 96%, at least 97%, at least 98%, or at least 99% identical to SEQ ID NO: 9.

In other examples, the microorganism (e.g., bacterium) comprises an exogenous nucleic acid encoding a fusion protein containing a TFF polypeptide and a CmbA polypeptide, wherein a secretion signal peptide is bound to the TFF polypeptide (e.g., SSusp45). For example, the fusion protein may include (or consist of) an amino acid sequence that is at least 90%, at least 92%, at least 95%, at least 96%, at least 97%, at least 98%, or at least 99% identical to SEQ ID NO: 10. In other examples, the fusion protein may be encoded by an exogenous nucleic acid sequence containing (or consisting of) a sequence that is at least 90%, at least 92%, at least 95%, at least 96%, at least 97%, at least 98%, or at least 99% identical to SEQ ID NO: 11.

In some examples, the secretion signal peptide includes a linker peptide. In some examples, the secretion signal peptide is cleaved from the fusion protein, e.g., when the fusion protein is anchored in a cell wall of the microorganism (e.g., bacterium).

In some examples, the exogenous nucleic acid encoding the fusion protein is transcriptionally regulated by (e.g., placed under the control of) a promoter that is endogenous to the microorganism (e.g., bacterium). In other examples, expression of the fusion protein is controlled by an exogenous promoter. In some examples, the promoter is selected from a thyA promoter (PthyA), an hila promoter (PhIIA), and a gapB promoter. In some examples, the nucleic acid encoding a fusion protein is transcriptionally regulated by a PthyA promoter. In other examples, the exogenous nucleic acid encoding the fusion protein is transcriptionally regulated by a PhIIA promoter. Other promoters include those preceding genes holA, soda, enoA, tufa, fbaA, acpA, ps431, malG, ptsH, dpsA, pgk, ahpC, pdhD, pts_II, pfk, trePP, ptnD, pgiA, usp45. Other suitable promoters are described, e.g., in U.S. Patent Application Publication 2014/0105863, the disclosure of which is incorporated herein by reference in its entirety.

The present disclosure further provides a microorganism (e.g., bacterium) comprising a fusion protein (e.g., anchored in a cell-wall of the microorganism, e.g., bacterium), wherein the fusion protein comprises a TFF polypeptide and a CmbA polypeptide. In some examples, the microorganism (e.g., bacterium) includes an exogenous nucleic acid comprising a secretion leader sequence, a sequence encoding the TFF polypeptide, and a sequence encoding the CmbA polypeptide. In some examples, the secretion leader sequence encodes a secretion signal peptide, which is cleaved from the fusion protein, e.g., when the fusion protein passes the cytoplasmic membrane (e.g., is anchored in the cell wall) of the microorganism (e.g., bacterium).

In some examples according to any of the above embodiments, the microorganism is a bacterium. In other examples according to any of the above embodiments, such bacterium is a Gram-positive bacterium, e.g., a non-pathogenic Gram-positive bacterium. In other examples according to any of the above embodiments, the bacterium is a lactic acid bacterium (LAB). Exemplary lactic acid bacteria are disclosed herein, each of which can be used in the context of these embodiments. In some embodiments, the LAB is selected from the group consisting of a *Lactococcus* species (sp.) bacterium, a *Lactobacillus* sp. bacterium, a *Bifidobacterium* sp. bacterium, a *Streptococcus* sp. bacterium, and an *Enterococcus* sp. bacterium. In some examples, the LAB is *Lactococcus lactis*. In other examples, the LAB is selected from *Lactococcus lactis* subsp. *cremoris*, *Lactococcus lactis* subsp. *hordniae*, and *Lactococcus lactis* subsp. *lactis*. In some examples, the *Lactococcus lactis* is *Lactococcus lactis* subsp. *cremoris*, such as *Lactococcus lactis* strain MG1363.

In some examples according to any of the above embodiments, the microorganism (e.g., bacterium) comprises an exogenous nucleic acid encoding a fusion protein comprising a TFF polypeptide and a cell-adherence polypeptide (e.g., CmbA). In some examples according to this embodiment, the TFF polypeptide is selected from TFF1, TFF2, and TFF3. In other examples according to this embodiment, the TFF polypeptide is selected from human TFF, mouse TFF, pig TFF, dog TFF, cat TFF, cow TFF, and sheep TFF. In some examples, the TFF polypeptide is human TFF. In other examples, the TFF polypeptide is selected from human TFF1, human TFF2, and human TFF3. In yet other example, the TFF polypeptide is human TFF3. In some example, the TFF polypeptide has an amino acid sequence at least 90%, at least 92%, at least 95%, at least 96%, at least 98%, or at least 99% identical to SEQ ID NO: 3. In other examples, the TFF polypeptide is a TFF variant polypeptide, e.g., a TFF variant polypeptide having enhanced mucin-binding capability when compared to a corresponding wild-type TFF polypeptide. In other examples, the TFF polypeptide is an amphibian or fish TFF polypeptide.

In some examples according to any of the above embodiments, the microorganism (e.g., bacterium) further contains an exogenous nucleic acid encoding at least one therapeutic polypeptide. In some examples, the therapeutic polypeptide is a cytokine, such as an interleukin (IL). The choice of cytokine is made on the basis of what host responses are sought to be activated or suppressed. In some examples, the cytokine is IL-2, IL-10, or IL-22. In other examples, the therapeutic polypeptide is an antigen. In other examples the therapeutic polypeptide is an antigen and an interleukin, such as IL-2, IL-10, or IL-22. In some examples according to any of these embodiments, the antigen is an autoantigen, e.g., a T1D-specific antigen. Exemplary T1D-specific antigens include proinsulin (PINS), glutamic acid decarboxylase (GAD65), insulinoma-associated protein 2 (IA-2), islet-specific glucose-6-phosphatase catalytic subunit-related protein (IGRP), zinc transporter 8 (ZnT8), chromogranin A, (prepro) islet amyloid polypeptide (ppIAPP), peripherin, citrullinated glucose-regulated protein (GRP), and a combinations thereof. Exemplary amino acid sequences and nucleic acid sequences for the above T1D-specific antigens are disclosed, e.g., in international patent application publication WO2017/122180, the disclosure of which is incorporated herein by reference in its entirety. In other examples, the antigen is an allergen, such as a tree pollen allergen, a weed pollen allergen, a grass pollen allergen, a food allergen, a dust-mite allergen, a mold allergen, an animal dander allergen, or a combination thereof. In some examples, the allergen is a weed pollen allergen, e.g., a ragweed pollen allergen. In other examples, the allergen is a tree pollen allergen, such as a birch pollen allergen or a Japanese cedar pollen allergen. In yet other examples, the allergen is a food allergen, such as a peanut allergen, a milk allergen, an egg allergen, a gluten allergen (gliadin epitope), or a combination thereof.

In further examples, the therapeutic polypeptide is an antibody or a fragment thereof. For example, the antibody is a single-domain antibody (e.g. camelid or shark antibody) or a nanobody. Exemplary antibodies include cytokine neutralizing antibodies such as antibodies to IL-4, antibodies to IL-5, antibodies to IL-7, antibodies to IL-13, antibodies to IL-15, as well as anti TNFα antibodies to immunoglobulin E (IgE), and any fragments thereof. In some examples, the therapeutic polypeptide is a fusion protein. For example, the therapeutic polypeptide comprises a soluble receptor, such as a TNF receptor (e.g., soluble TNF receptor 2) and an antibody or an antibody fragment, such as the Fc region of an antibody. In some examples according to these embodiments, the therapeutic polypeptide contains an Fc region of a human immunoglobulin (e.g., human IgG1 Fc). In some examples, the therapeutic polypeptide comprises soluble TNF receptor 2 fused to human IgG1 Fc). In some examples, the therapeutic polypeptide is etanercept.

In yet other examples, the therapeutic polypeptide is an enzyme or a fragment (e.g., functional fragment) thereof, e.g., a phenylalanine ammonia lyase (PAL), an amino acid decarboxylase, or a combination thereof. In one example, the therapeutic polypeptide is PAL, or a functional fragment thereof.

In further examples, the therapeutic polypeptide is a glucagon-like peptide 1 (GLP-1), glucagon-like peptide 2 (GLP-2), glucagon, exendin-4, or any combination thereof. In other examples, the therapeutic polypeptide is a growth factor, such as an epidermal growth factor (EGF), e.g., human EGF or porcine EGF. In yet other examples, the therapeutic polypeptide is a TFF, such as TFF1, TFF2, TFF3, or a combination thereof.

The therapeutic polypeptide may be a combination of any of the above recited therapeutic polypeptides.

In some examples according to any of the above embodiments, the exogenous nucleic acid encoding the at least one therapeutic polypeptide is transcriptionally regulated by a promoter selected from a gapB promoter (PgapB), a thyA promoter (PthyA), and an hlla promoter (PhllA). In some examples, the exogenous nucleic acid encoding the at least one therapeutic polypeptide is transcriptionally regulated by (e.g., under the control of) a gapB promoter. Other promoters include those preceding genes holA, soda, enoA, tufa, fbaA, acpA, ps431, malG, ptsH, dpsA, pgk, ahpC, pdhD, pts_II, pfk, trePP, ptnD, pgiA, usp45. Other suitable promoters are described, e.g., in U.S. Patent Application Publication 2014/0105863, the disclosure of which is incorporated herein by reference in its entirety.

In some examples according to any of the above embodiments, the microorganism (e.g., LAB) further comprises a combination of mutations and insertions to promote trehalose accumulation, which enhances LAB survivability against bile salts and drying. For example, these may be
 (i) chromosomally-integrated trehalose transporter(s), such as PhllA>>transporter 1>>intergenic region>>transporter 2, such as llmg_0453 and/or llmg_0454, for uptake of trehalose;
 (ii) chromosomally-integrated Trehalose-6-phosphate phosphatase gene (otsB; Gene ID: 1036914) positioned downstream of usp45 (Gene ID: 4797218) to facilitate conversion of trehalose-6-phosphate to trehalose;
 (iii) inactivated (e.g., through gene deletion) Trehalose-6-phosphate phosphorylase gene (trePP; Gene ID: 4797140); and
 (iv) inactivated cellobiose-specific PTS system IIC component (Gene ID: 4796893), ptcC, (e.g., tga at codon position 30 of 446; tga30).

For example, an exogenous nucleic acid encoding a trehalose-6-phosphate phosphatase, e.g., otsB, such as *Escherichia coli* otsB. In some examples according to these embodiments, the exogenous nucleic acid encoding the trehalose-6-phosphate phosphatase is chromosomally integrated. In some examples, the exogenous nucleic acid encoding the trehalose-6-phosphate phosphatase is chromosomally integrated 3' of unidentified secreted 45-kDa protein gene (usp45). In some examples according to this embodiment, the LAB comprises a second polycistronic expression cassette comprising a usp45 promoter, the usp45 gene (e.g., 3' of the promoter), and the exogenous nucleic acid encoding a trehalose-6-phosphate phosphatase (e.g., 3' of the usp45 gene). In some examples, the second polycistronic expression cassette further comprises an intergenic region between the usp45 gene and the exogenous nucleic acid encoding a trehalose-6-phosphate phosphatase. In some examples, the second polycistronic expression cassette is illustrated by: Pusp45>>usp45>>intergenic region>>otsB. In some examples according to these embodiments, the intergenic region is rpmD as described herein above (e.g., having SEQ ID NO: 8 or SEQ ID NO: 9). The second polycistronic expression cassette may then be illustrated by: Pusp45>>usp45>>rpmD>>otsB.

In some examples according to any of the above embodiments, a trehalose-6-phosphate phosphorylase gene (trePP) is disrupted or inactivated in the microorganism (e.g., LAB). For example, the trePP has been inactivated by removing the trePP gene or a fragment thereof, or the trePP has been disrupted by inserting a stop codon. Thus, in some examples according to these embodiments, the microorganism (e.g., LAB) lacks trePP activity.

In other examples according to any of the above embodiments, a cellobiose-specific PTS system IIC component gene (ptcC) has been disrupted or inactivated in the microorganism (e.g., LAB). For example, the ptcC has been disrupted by inserting a stop codon, or ptcC has been inactivated by removing the ptcC or a fragment thereof. Thus, in some examples according to these embodiments, the microorganism (e.g., LAB) lacks ptcC activity.

In other examples according to any of the above embodiments, the LAB further comprises one or more genes encoding one or more trehalose transporter(s). In some examples, the one or more genes encoding the one or more trehalose transporter(s) are endogenous to the LAB. In some examples, the LAB overexpresses the one or more genes encoding the one or more trehalose transporter(s). In some examples according to these embodiments, the one or more genes encoding the one or more trehalose transporter(s) is positioned 3' of an exogenous promoter, e.g., an hllA promoter (PhllA). For example, the one or more genes encoding the one or more trehalose transporter(s) are transcriptionally regulated by the PhllA. In some examples according to these embodiments, the one or more genes encoding the one or more trehalose transporter(s) is selected from llmg_0453, llmg_0454, and any combination thereof. In some examples, llmg_0453 and llmg_0454 are transcriptionally regulated by a PhllA.

In some examples, according to any of the above embodiments, the one or more genes encoding one or more trehalose transporter(s) comprises two genes encoding two or more trehalose transporters, wherein an intergenic region is located between the two genes. In some examples, the intergenic region is rpmD, e.g., having SEQ ID NO: 8 or SEQ ID NO: 9. In some examples, the microorganism (e.g., LAB) comprises a polycistronic expression cassette comprising two nucleic acid sequences (e.g., genes) encoding two different trehalose transporters (transporter 1 and transporter 2 sequences) and an intergenic region between the two nucleic acids encoding the two different trehalose transporters. Such expression cassette may be illustrated by: PhllA>>transporter 1>>intergenic region>>transporter 2. In some examples according to these embodiments, the intergenic region is rpmD as described herein above (e.g., having SEQ ID NO: 8 or SEQ ID NO: 9). The polycistronic expression cassette may then be illustrated by: PhllA>>transporter1>>rpmD>>transporter2.

Thus, in some embodiments, the LAB comprises, in a single strain, several useful features. In one embodiment, the LAB is *Lactococcus lactis*, comprising:
(A) a chromosomally integrated promoter>>secretion signal>>mucin and cell adherence fusion protein;
(B) one or more of a chromosomally-integrated promoter>>secretion signal>>therapeutic protein;
(C) a combination of mutations and insertions to promote trehalose accumulation, which enhances LAB survivability against bile salts and drying. The mutations are selected from
  (i) chromosomally-integrated trehalose transporter(s), such as PhllA>>transporter 1>>intergenic region>>transporter 2, such as llmg_0453 and/or llmg_0454, for uptake of trehalose;
  (ii) chromosomally-integrated Trehalose-6-phosphate phosphatase gene (otsB; Gene ID: 1036914) positioned downstream of usp45 (Gene ID: 4797218) to facilitate conversion of trehalose-6-phosphate to trehalose;
  (iii) inactivated (e.g. through gene deletion) Trehalose-6-phosphate phosphorylase gene (trePP; Gene ID: 4797140); and
  (iv) inactivated cellobiose-specific PTS system IIC component (Gene ID: 4796893), ptcC, (e.g. tga at codon position 30 of 446; tga30).

The LAB may also contain an auxotrophic mutation for biological containment, such as thyA. One or more of these functions (i.e. mucin and cell adherence, therapeutic protein, trehalose accumulation) may be in a polycistronic operon, wherein each gene may be separated by an intergenic region.

In one embodiment, the LAB is *Lactococcus lactis*, with
(A) thyA mutation, for biological containment
(B) a chromosomally integrated PthyA>>SSusp45-hTFF3-cmbA to export and link to the cell wall a mucus and cell binding fusion protein.
(C) a chromosomally-integrated PgapB>>gapB>>intergenic region (such as rpmD)>>SSusp45>>pal, to secrete mature PAL from LAB;
(D) chromosomally-integrated trehalose transporter(s), such as PhllA>>transporter 1>>intergenic region>>transporter 2, such as llmg_0453 and/or llmg_0454, for uptake of trehalose;
(E) inactivated (e.g. through gene deletion) Trehalose-6-phosphate phosphorylase gene (trePP; Gene ID: 4797140);
(F) chromosomally integrated Trehalose-6-phosphate phosphatase gene (otsB; Gene ID: 1036914) (positioned downstream of usp45 (Gene ID: 4797218) to facilitate conversion of trehalose-6-phosphate to trehalose; and
(G) inactivated cellobiose-specific PTS system IIC component (Gene ID: 4796893), ptcC, (e.g. tga at codon position 30 of 446; tga30).

In some examples according to any of the above embodiments, the microorganism (e.g., bacterium) has an increased gastro-intestinal (GI) transit time when compared to a corresponding microorganism (e.g., bacterium) not comprising the described genetic modification, i.e., not comprising said exogenous nucleic acid encoding the fusion protein or not comprising said fusion protein. In some examples, the GI transit time is increased by at least about 10%, at least about 30%, at least about 50%, at least about 80%, or at least about 100% (to about 2x). In other examples, the GI transit time is increased from at least about 10% to about 500%, from at least about 20% to about 400%, from at least about 20% to about 300%, from at least about 20% to about 300%, or from at least about 30% to about 300%.

In some examples according to any of the above embodiments, the microorganism (e.g., bacterium) exhibits increased in vitro mucin-binding capability when compared to a corresponding microorganism (e.g., bacterium) not genetically modified as described herein, i.e., not comprising an exogenous nucleic acid encoding a fusion protein or not comprising a fusion protein. In some examples, the in vitro mucin-binding capability is increased by at least about 20%, at least about 30%, at least about 40%, at least about 50%, at least about 60%, at least about 70%, at least about 80%, at least about 90% or at least about 100% (to about 2×). In other examples, the mucin-binding capability is increased from at least about 10% to about 500%, from at least about 10% to about 400%, from at least about 10% to about 300%, from at least about 10% to about 200%, from at least about 20% to about 200%, from at least about 20% to about 300%, or from at least about 20% to about 500%.

Mucin-binding capabilities can be measured in accordance with any art-recognized method, e.g., those described herein. In some examples, in vitro mucin-binding capability is measured by contacting and binding the microorganism (e.g., a bacterium) to immobilized mucins (e.g., mucins from porcine stomach), and measuring the number of microbial cells (e.g., bacterial cells) bound to the mucin, e.g., by detecting light absorbance at an appropriate wavelength, e.g., at 405 nm ($OD_{405}$); or by staining the bound microbial cells (e.g., bound bacterial cells) with a dye (e.g., crystal violet) and subsequently detecting light absorbance at a wavelength appropriate for the employed dye. For example, if crystal violet is used to stain bacterial cells bound to the mucin, light absorbance may be measured at 595 nm ($OD_{595}$).

In some examples according to any of the above embodiments, the microorganism (e.g., bacterium) exhibits increased in vitro Caco-2 cell-binding capability when compared to a corresponding microorganism (e.g., bacterium) without the described genetic modification, i.e., not comprising an exogenous nucleic acid encoding the fusion protein, or not comprising the fusion protein. In some examples, the in vitro Caco-2 binding capability is increased by at least about 10%, at least about 20%, at least about 30%, at least about 40%, at least about 50%, at least about 60%, at least about 80%, at least about 100% (to about 2×), at least about 200%, at least about 300%, or at least about 400% (about 5×). In other examples, the in vitro Caco-2 binding capability is increased from at least about 10% to about 200%, from at least about 10% to about 300%, from at least about 10% to about 400%, or from at least about 10% to about 500%. Caco-2 cell binding capability can be measured in accordance with any art-recognized method, such as those disclosed herein. For example, Caco-2 binding capability is measured by: (i) contacting the microorganism (e.g., bacterium), e.g., a culture of the microorganism (e.g., bacterium) with Caco-2 cells; (ii) washing the Caco-2 cells to remove unbound microbial (e.g., bacterial cells); (iii) detaching the microbial cells (e.g., bacterial cells) that are bound to the Caco-2 cells; and (iv) determining the number of detached bacterial cells (i.e., titering the detached cells), e.g., as described herein.

In some examples according to any of the above embodiments, the microorganism (e.g., bacterium) exhibits increased adherence to intestinal mucosa when compared to a corresponding microorganism (e.g., bacterium) without the described genetic modification, i.e., not comprising an exogenous nucleic acid encoding the fusion protein or not comprising the fusion protein. In some examples, adherence of the microorganism (e.g., bacterium) to intestinal mucosa is increased from at least about 10% to about 100% (to about 2×), from at least about 10% to about 200%, from at least about 10% to about 400%, or from at least about 10% to about 500%.

The present disclosure further provides a composition comprising a microorganism (e.g., a bacterium) of the present disclosure, e.g., a microorganism (e.g., bacterium) as described in any of the above embodiments. For example, the present disclosure provides a composition comprising a microorganism (e.g., a bacterium) comprising a fusion protein (e.g., anchored in a cell-wall of the microorganism, e.g., bacterium), wherein the fusion protein comprises a TFF polypeptide and a CmbA polypeptide. In some examples, the microorganism (e.g., bacterium) includes an exogenous nucleic acid comprising a secretion leader sequence (e.g., SSusp45), a sequence encoding the TFF polypeptide, and a sequence encoding the CmbA polypeptide. In some examples, the secretion leader sequence encodes a secretion signal peptide, which is cleaved from the fusion protein, e.g., when the fusion protein is passing the cytoplasmic membrane of the bacterium.

The present disclosure further provides a pharmaceutical composition comprising a microorganism (e.g., a bacterium) of the present disclosure and a pharmaceutically acceptable carrier. For example, the pharmaceutical composition contains a microorganism (e.g., a bacterium) as described in any of the above embodiments.

The present disclosure further provides a microorganism (e.g., bacterium) of the present disclosure, or a composition (e.g., a pharmaceutical composition) of the present disclosure for use in the treatment of a disease. The present disclosure further provides a microorganism (e.g., a bacterium) or a composition (e.g., a pharmaceutical composition) for use in the preparation of a medicament for the prevention or treatment of a disease. In some examples according to any of these embodiments, the disease is selected from an autoimmune disease, an allergy, a nutritional or metabolic disease, a gastro-intestinal disease, and a genetic disorder. Further diseases that can be treated using the microorganisms (e.g., bacteria) and compositions of the present disclosure are described herein.

The present disclosure further provides an isolated nucleic acid encoding a fusion protein, said nucleic acid comprising: (i) a sequence encoding a mucin-binding polypeptide, such as a TFF polypeptide (e.g., TFF1, TFF2, or TFF3) or a MucBP polypeptide; and (ii) a sequence encoding a cell-adherence polypeptide, such as a CmbA polypeptide, a Mub polypeptide, a MapA polypeptide, or a MbpL polypeptide. In some examples according to these embodiments, the cell-adherence polypeptide is a CmbA polypeptide. Accordingly, the present disclosure provides an isolated nucleic acid encoding a fusion protein, wherein the nucleic acid contains (i) a sequence encoding a TFF polypeptide, such as TFF1 (e.g., human TFF1), TFF2 (e.g., human TFF2), or TFF3 (e.g., human TFF3), and (ii) a sequence encoding a CmbA polypeptide.

The present disclosure further provides a plasmid comprising the isolated nucleic acid of the present disclosure, e.g., an isolated nucleic acid in accordance with any of the above embodiments.

The present disclosure further provides a microbial (e.g., bacterial) host cell comprising an isolated nucleic acid of the present disclosure or a plasmid of the present disclosure.

The present disclosure further provides a kit comprising (1) a microorganism (e.g., a bacterium), a composition, a pharmaceutical composition, or a unit dosage form of the present disclosure; and (2) instructions for administering the microorganism (e.g., bacterium), the composition, the pharmaceutical composition, or the unit dosage form to a mammal, such as an animal or human subject or patient.

Methods

The present disclosure further provides methods for the treatment of a disease in a subject in need thereof. Exemplary methods include: administering to the subject a therapeutically effective amount of a microorganism (e.g., a bacterium), a composition, or a pharmaceutical composition of the present disclosure. In some examples according to these embodiments, the microorganism (e.g., bacterium) comprises an exogenous nucleic acid encoding a therapeutic polypeptide as described herein. Exemplary diseases that can be treated using such microorganisms (e.g., bacteria) and compositions of the present disclosure are described herein. In some examples, the disease is an autoimmune disease, an allergy, a nutritional or a metabolic disease, a gastro-intestinal disease, a genetic disorder, or any combinations thereof. In some examples according to any of the above embodiments, the disease is an autoimmune disease, such as type-1 diabetes (T1D). In other examples, the disease is a metabolic disease, such as phenylketonuria (PKU). In other examples, the disease is a gastro-intestinal disease, such as celiac disease, or inflammatory bowel disease (IBD), e.g., Crohn's disease or ulcerative colitis. In further examples, the disease is growth retardation.

In some embodiments, the disease is phenylketonuria (PKU). In some examples according to this embodiment, the microorganism (e.g., bacterium) comprises an exogenous nucleic acid encoding a polypeptide, e.g., an enzyme that is capable of degrading phenylalanine (Phe), e.g., in the GI tract, e.g., prior to absorption of the Phe by the subject to which the microorganism is being administered. In some examples according to these embodiments, the microorganism (e.g., bacterium) comprises an exogenous nucleic acid encoding a phenylalanine ammonia lyase (PAL), an enzyme that converts Phe to cinnamic acid. Thus, the present disclosure provides methods for the treatment of PKU in a subject in need thereof. Exemplary methods include: administering to the subject a therapeutically effective amount of a microorganism (e.g., a bacterium), a composition, or a pharmaceutical composition of the present disclosure, wherein the microorganism (e.g., bacterium) comprises an exogenous nucleic acid encoding PAL. Inhibition of Phe absorption and treatment of PKU may be analyzed using a mouse PKU model, e.g., utilizing (enu2/2) mice (see, e.g., Sarkissian, C. N. et al., *Proc. Natl. Acad. Sci. USA* 1999, 96: 2339-2344), or using a rat model (see, e.g., Chang et al., *Artif Cells Blood Substit. Immobil. Biotechnol.* 1995, 23(1): 1-21).

The present disclosure further provides methods for preparing a genetically modified microorganism (e.g., bacterium). Exemplary methods include: contacting an exogenous nucleic acid encoding a fusion protein with a microorganism (e.g., bacterium), wherein the exogenous nucleic acid encoding the fusion protein comprises a sequence encoding a cell-adherence polypeptide, such as a CmbA polypeptide, a Mub polypeptide, a MapA polypeptide, or a MbpL polypeptide. In some examples, the cell-adherence polypeptide is CmbA, e.g., *Lactobacillus reuteri* CmbA. In some examples, carrying out the above method (i.e., contacting the microorganism with the exogenous nucleic acid) results in a microorganism (e.g., bacterium) containing the exogenous nucleic acid encoding the fusion protein. In other examples, contacting the microorganism (e.g., bacterium) with the exogenous nucleic acid results in a microorganism (e.g., bacterium) containing the exogenous nucleic acid encoding the fusion protein, and thereby expressing the fusion protein encoded by the exogenous nucleic acid. In some examples, the method further includes culturing the microorganism (e.g., bacterium) and expressing the fusion protein in the microorganism (e.g., bacterium). In some examples, the contacting occurs under conditions sufficient for said bacterium to internalize the exogenous nucleic acid. In some examples according to any of these embodiments, the exogenous nucleic acid is located on a plasmid. In some examples according to these embodiments, the exogenous nucleic acid is integrated into the chromosome of the bacterium.

In some examples according to any of the above embodiments, the exogenous nucleic acid encoding the fusion protein further comprises a sequence encoding a mucin-binding polypeptide, such as a trefoil factor (TFF) polypeptide or a MucBP polypeptide. In some examples, the exogenous nucleic acid encoding the fusion protein comprises a sequence encoding CmbA and a sequence encoding a TFF polypeptide. Accordingly, the present disclosure provides a method for preparing a genetically modified microorganism (e.g., bacterium) comprising: contacting an exogenous nucleic acid encoding a fusion protein with a microorganism (e.g., bacterium), wherein the exogenous nucleic acid encoding the fusion protein comprises (i) a sequence encoding a TFF polypeptide (e.g., TFF1, TFF2, or TFF3) and (ii) a sequence encoding CmbA. In some examples according to any of these embodiments, the exogenous nucleic acid encoding the fusion protein is chromosomally integrated (e.g., integrated into the chromosome of a bacterium), e.g., by using homologous recombination. In accordance with this embodiment, the method can further include forming a plasmid (i.e., an integration plasmid) comprising the exogenous nucleic acid encoding the fusion protein.

In one example according to any of the above embodiments, the method further includes contacting the microorganism (e.g., bacterium) with an exogenous nucleic acid encoding a therapeutic polypeptide, e.g., prior to or subsequent to contacting the microorganism (e.g., bacterium) with an exogenous nucleic acid encoding the fusion protein.

In some examples according to any of the above embodiments, the genetically modified microorganism (e.g., bacterium) prepared by the above methods exhibits increased muco- and/or cell-adhesive properties as described herein when compared to a corresponding microorganism (e.g., bacterium) not modified according to the instant method, i.e., not comprising an exogenous nucleic acid encoding the fusion protein.

In related embodiments, the adhesion to mucus and/or cells is specific to types of mucus and/or cells. As a result of preferential binding to specific receptors found in specific cells or mucus, the bacterium may be localized to specific sites. In such a way, it is possible to ensure localization of the bacterium to the site where delivery of specific molecules is most effective. In some embodiments that location may be the mucosae (intestine, oral cavity, eye, ear, urogenital). In some embodiments that location may be the small bowel, in some embodiments that location may be the upper small bowel.

In some examples, the method further includes combining a culture of the genetically modified bacterium with at least one cryopreserving agent to form a bacterial mixture. The method may further include drying (e.g., freeze-drying or spray drying) the bacterial mixture to form a dried (e.g., freeze-dried) composition. The method can further include combining the genetically modified bacterium, or the dried composition (e.g., freeze-dried composition) with a pharmaceutically acceptable carrier to form a pharmaceutical composition. The method may further include formulating the genetically modified bacterium, the dried (e.g., freeze-dried) composition, or the pharmaceutical composition into a pharmaceutical unit dosage form, such as a tablet, capsule, or granule.

The current disclosure further provides a unit dosage form comprising at least one microorganism (e.g., a bacterium), a composition, or a pharmaceutical composition of the present disclosure. In some examples, such unit dosage form is an oral dosage form. In other examples according to these embodiments, the unit dosage form is a capsule (e.g., a capsule containing a powder or containing micro-pellets or micro-granules), a tablet, a granule, a sachet, or a packaged liquid, e.g., suspension. In other embodiments, the unit dosage form is a metered aerosol dose, or a suppository.

In some embodiments, the microorganism (e.g., the non-pathogenic Gram-positive bacterium) contained in the dosage form is in a dry-powder form or a compacted version thereof.

The current disclosure further provides a unit dosage form comprising from about $1\times10^4$ to about $1\times10^{12}$ colony-forming units (cfu) of a microorganism of the present disclosure, e.g., a non-pathogenic microorganism (e.g., a non-pathogenic Gram-positive bacterium). In some embodiments, the unit dosage form comprises from about $1\times10^6$ to about $1\times10^{12}$ colony-forming units (cfu) of the microorganism (e.g., the non-pathogenic Gram-positive bacterium). In other embodiments, the unit dosage form comprises from about $1\times10^9$ to about $1\times10^{12}$ colony-forming units (cfu) of the microorganism (e.g., the non-pathogenic Gram-positive bacterium).

In some embodiments in any of the above methods, the microorganism (e.g., bacterium) is administered to a subject orally. For example, the microorganism (e.g., bacterium) is administered to the subject in the form of a pharmaceutical composition for oral administration (e.g., a capsule, tablet, granule, suspension or liquid) comprising the microorganism (e.g., bacterium) and a pharmaceutically acceptable carrier. In other examples, the microorganism (e.g., bacterium) is administered to the subject in the form of a food product, or is added to a food (e.g., a drink). In other examples, the microorganism (e.g., bacterium) is administered to the subject in the form of a dietary supplement. In yet other examples, the microorganism (e.g., bacterium) is administered to the subject in the form of a suppository product. In some examples, the compositions of the present disclosure are adapted for mucosal delivery of the polypeptides, which are expressed by the microorganism (e.g., bacterium). For example, compositions may be formulated for efficient release of a therapeutic polypeptide in the intestinal tract of the subject.

The current disclosure further provides a genetically modified bacterium, a composition, a pharmaceutical composition, or a unit dosage form prepared by a method in accordance with any of the above embodiments.

The present disclosure further provides methods for enhancing growth in a mammal. Exemplary methods include administering to the mammal an effective amount of a microorganism (e.g., bacterium), a composition, a pharmaceutical composition, or a unit dosage form of the present disclosure. In some examples, the mammal is a human, a farm animal (e.g., a pig, a cow, a goat, or a sheep), a dog, a cat, or other domestic animal. In some examples, the microorganism (e.g., bacterium), the composition, pharmaceutical composition, or the unit dosage form is formulated for administration to the mammal, e.g., is formulated for oral administration. In some examples, the microorganism (e.g., bacterium) employed in this method, contains an exogenous nucleic acid encoding a growth factor or growth hormone. In some examples according to this embodiment, the growth factor or growth hormone is constitutively expressed in the microorganism (e.g., bacterium). In some examples, the growth factor is EGF. In other examples, the mammal is a pig and the EGF is porcine EGF.

The present disclosure further provides a method for increasing binding of a microorganism (e.g., a bacterium) to intestinal mucosa (e.g., as measured by in vitro binding to a mucin preparation). Exemplary methods include contacting the microorganism (e.g., bacterium) with an exogenous nucleic acid encoding a fusion protein, wherein the exogenous nucleic acid encoding a fusion protein comprises a sequence encoding a CmbA polypeptide; and expressing the exogenous nucleic acid encoding a fusion protein in the microorganism (e.g., bacterium). In some examples, the exogenous nucleic acid encoding a fusion protein further comprises a sequence encoding a mucin-binding polypeptide, such as a TFF polypeptide. In some examples, expression of the exogenous nucleic acid encoding a fusion protein by the microorganism (e.g., bacterium) produces a fusion protein comprising the TFF polypeptide and the CmbA polypeptide.

In some examples according to any of the above described compositions and methods, the microorganism is a non-pathogenic microorganism, e.g., any microorganism safe for consumption by a mammalian subject. In some embodiments, the microorganism in the above compositions and methods is yeast. The yeast may be selected from *Saccharomyces* species, *Hansenula* species, *Kluyveromyces* species, *Schizzosaccharomyces* species, *Zygosaccharomyces* species, *Pichia* species, *Monascus* species, *Geothchum* species, and *Yarrowia* species. In some examples, the yeast is *Saccharomyces cerevisiae*.

In other embodiments in the above compositions and methods, the non-pathogenic microorganism is a non-pathogenic bacterium. In some examples according to this embodiment, the non-pathogenic bacterium is a Gram-positive bacterium. In other examples, the Gram-positive bacterium is a lactic acid fermenting bacterium (LAB), e.g., is selected from *Lactococcus* species (e.g., *Lactococcus lactis*), *Lactobacillus* species, and *Bifidobacterium* species. In other examples, the non-pathogenic bacterium is a *Streptococcus* species or an *Enterococcus* species. Additional bacterial species are disclosed herein.

CmbA on the bacterial surface. Mucin type II=mucin from porcine stomach, bound sialic acid, ~1%; Mucin type III=mucin from porcine stomach, bound sialic acid (0.5-1.5%).

Figure 3:
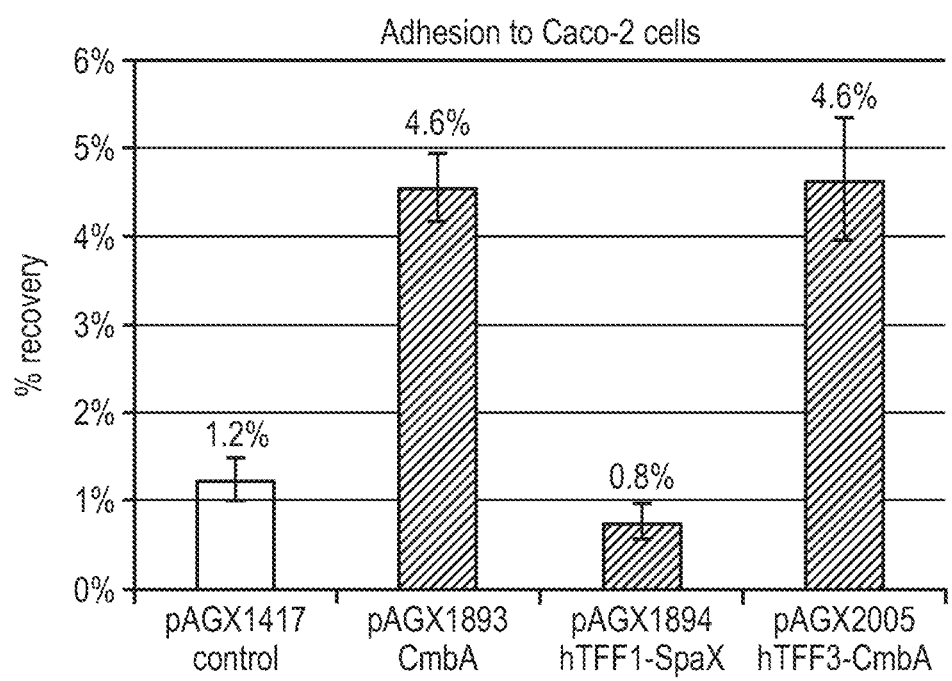

FIG. 3 demonstrates enhanced adherence of bacterial (*Lactococcus lactis*) cells to Caco-2 cells. pAGX1417: *L. lactis* strain LL108 that harbors an empty plasmid; pAGX1893: *L. lactis* strain LL108 that harbors a plasmid for expressing CmbA on the bacterial surface; pAGX1894: *L. lactis* strain LL108 that harbors a plasmid for expressing hTFF1-spaX on the bacterial surface; pAGX2005: *L. lactis* strain LL108 that harbors a plasmid for expressing hTFF3-CmbA on the bacterial surface.

FIG. 4 illustrates an exemplary SSusp45-htff3 construct (amino acid and nucleic acid sequences: SEQ ID NO: 8 and SEQ ID NO: 9, respectively).

Figure 5A:
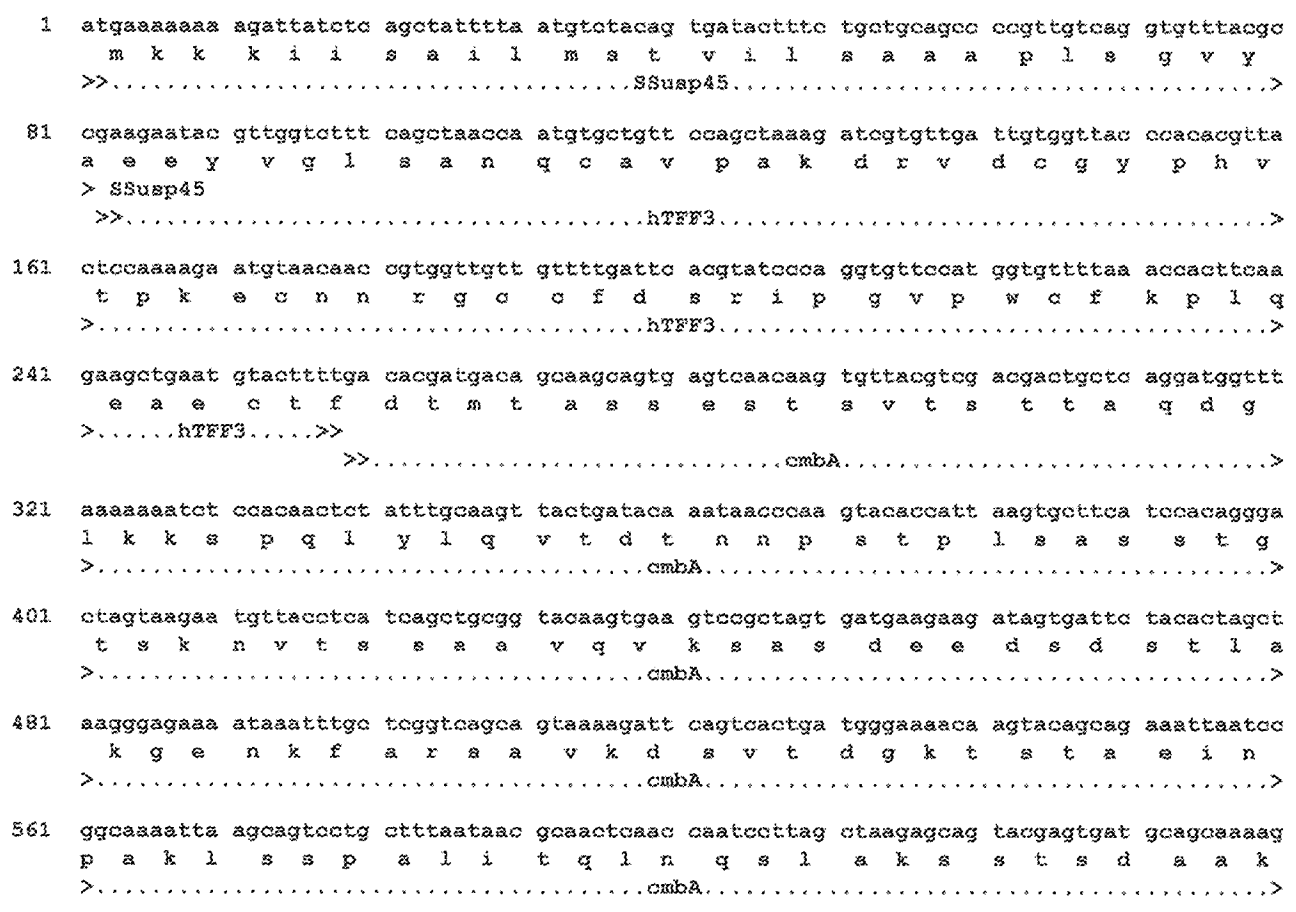

FIGS. 5A-D are collectively an illustration of an exemplary SSusp45-hTFF3-CmbA construct (amino acid and nucleic acid sequences: SEQ ID NO: 10 and SEQ ID NO: 11, respectively).

Figure 6:
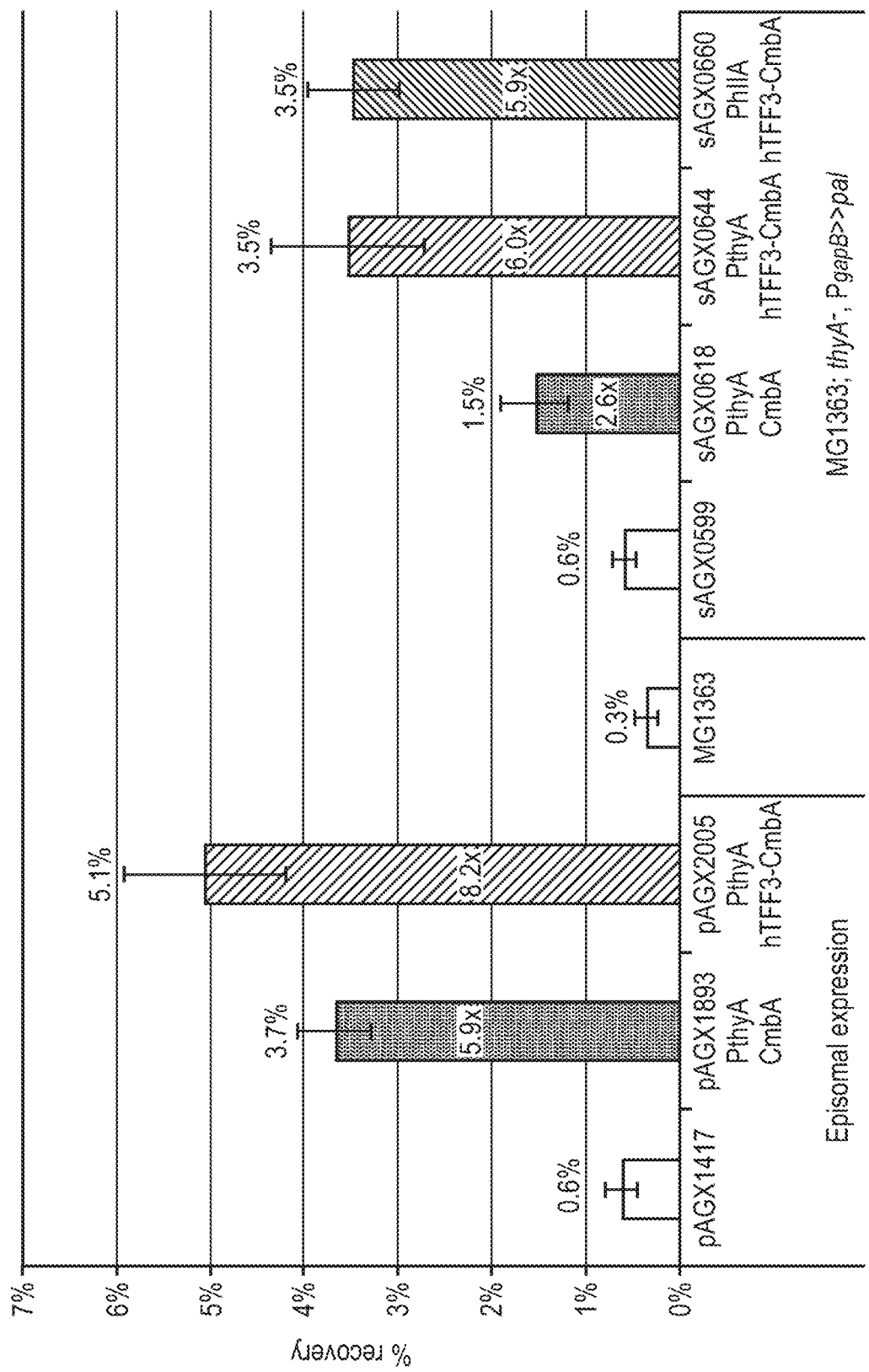

FIG. 6 is a graph illustrating enhanced adherence of bacterial (*Lactococcus lactis*) cells to Caco-2 cells, wherein the cells either episomally or constitutively express an exemplary cell adherence polypeptide (CmbA) or an exemplary fusion protein (hTFF3-CmbA). % recovery=% of *L. lactis* cells that were recovered from the mucin coated well after washing compared to the total applied *L. lactis* cells, as determined by colony forming units count. pAGX1893: *L. lactis* strain LL108 that harbors a plasmid for expressing CmbA on the bacterial surface; pAGX2005: *L. lactis* strain LL108 that harbors a plasmid for expressing hTFF3-CmbA on the bacterial surface; sAGX0618: *L. lactis* strain MG1363 constitutively expressing an exemplary therapeutic polypeptide PAL (PgapB>>pal) and constitutively expressing CmbA on the bacterial surface (thyA⁻; PthyA>>cmbA); sAGX644: *L. lactis* strain MG1363 constitutively expressing an exemplary therapeutic polypeptide PAL (PgapB>>pal) and constitutively expressing fusion protein hTFF3-CmbA on the bacterial surface, wherein an exogenous nucleic acid encoding the fusion protein is transcriptionally regulated by an endogenous thyA promoter at the thyA locus (thyA⁻; PthyA>>SSusp45-htff3-mbA); sAGX660: *L. lactis* strain MG1363 constitutively expressing an exemplary therapeutic polypeptide PAL (PgapB>>pal) and constitutively expressing the fusion protein hTFF3-CmbA on the bacterial surface, wherein an exogenous nucleic acid encoding the fusion protein is transcriptionally regulated by an hllA promoter at the thyA locus (thyA⁻; PhllA>>SSusp45-htff3-cmbA).

Figure 7A:
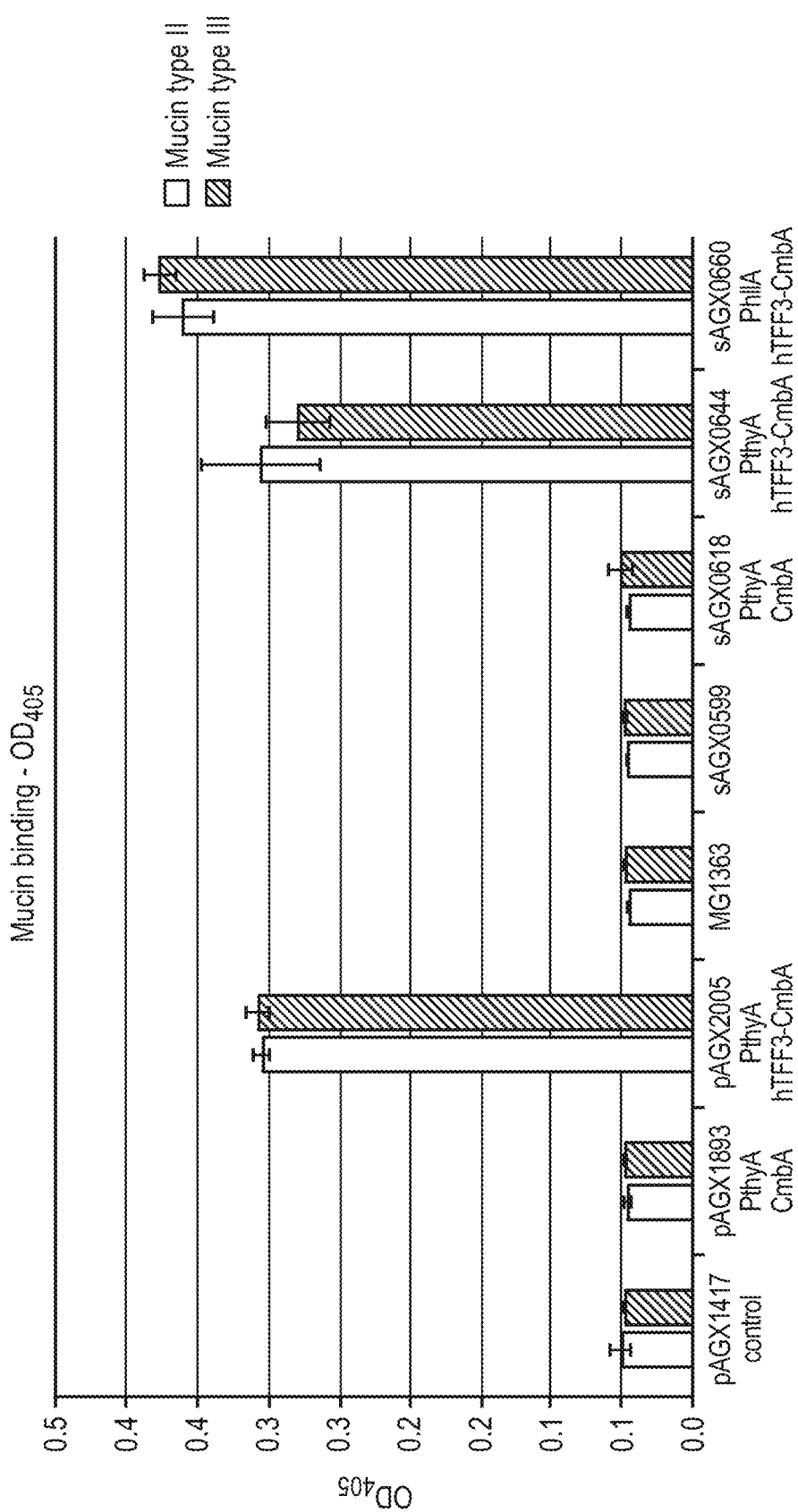
Figure 7B:
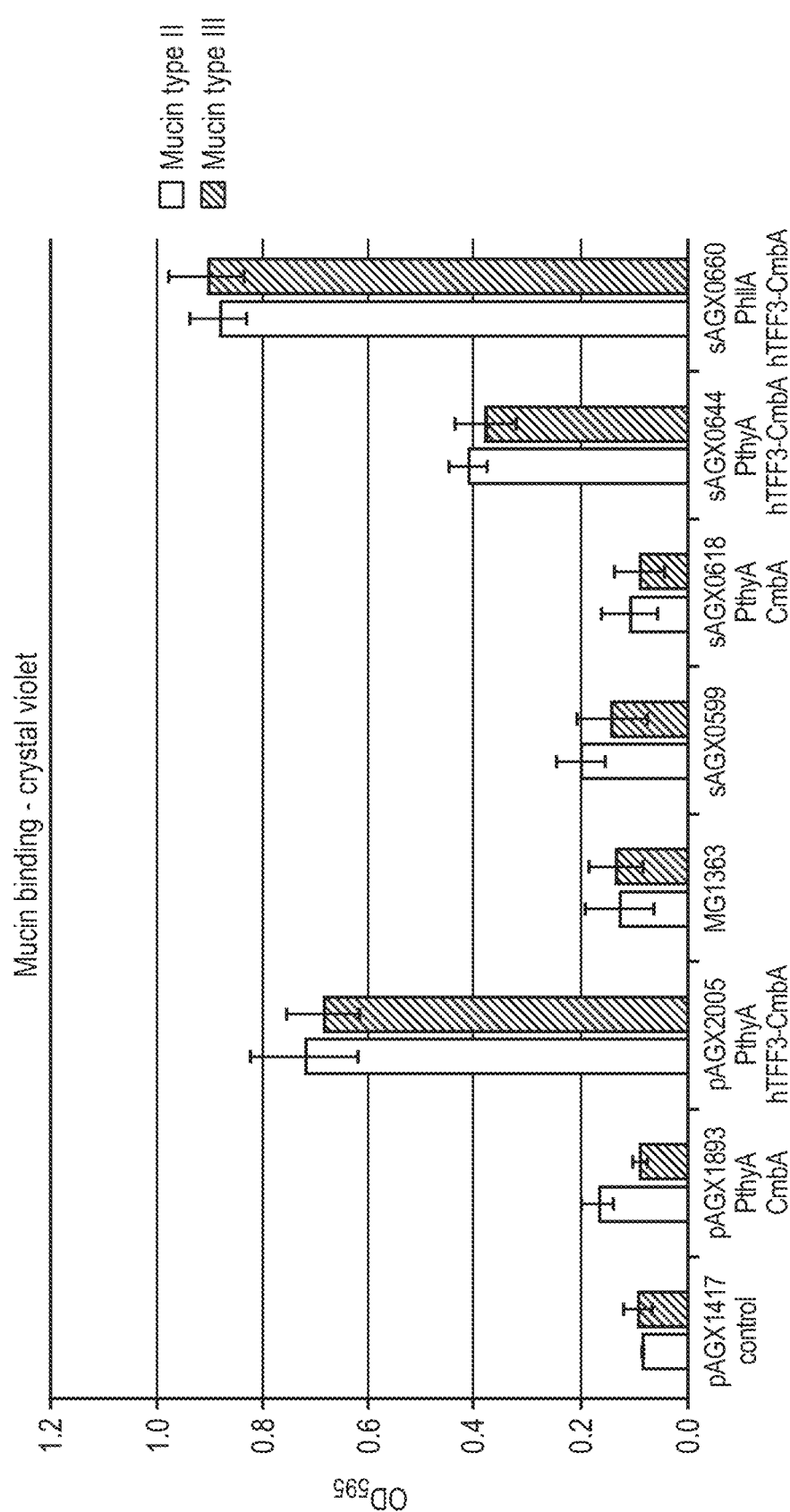

FIGS. 7A-B illustrate enhanced binding of bacterial (*Lactococcus lactis*) cells to mucins, wherein the cells either episomally or constitutively express an exemplary cell adherence polypeptide (CmbA) or an exemplary fusion protein (hTFF3-CmbA), and wherein mucin binding is measured using $OD_{405}$ (FIG. 7A) or crystal violet staining (FIG. 7B) as described herein, e.g., in Example 6. pAGX1893: *L. lactis* strain LL108 that harbors a plasmid for expressing CmbA on the bacterial surface; pAGX2005: *L. lactis* strain LL108 that harbors a plasmid for expressing hTFF3-CmbA on the bacterial surface; sAGX0618: *L. lactis* strain MG1363 constitutively expressing an exemplary therapeutic polypeptide PAL (PgapB>>pal) and constitutively expressing CmbA on the bacterial surface (thyA⁻; PthyA>>cmbA); sAGX644: *L. lactis* strain MG1363 constitutively expressing an exemplary therapeutic polypeptide PAL (PgapB>>pal) and constitutively expressing fusion protein hTFF3-CmbA on the bacterial surface, wherein an exogenous nucleic acid encoding the fusion protein is transcriptionally regulated by an endogenous thyA promoter at the thyA locus (thyA⁻; PthyA>>SSusp45-htff3-cmbA); sAGX660: *L. lactis* strain MG1363 constitutively expressing an exemplary therapeutic polypeptide PAL (PgapB>>pal) and constitutively expressing the fusion protein htff3-CmbA on the bacterial surface, wherein an exogenous nucleic acid encoding the fusion protein is transcriptionally regulated by an hllA promoter at the thyA locus (thyA⁻; PhllA>>SSusp45-htff3-cmbA).

Figure 8:
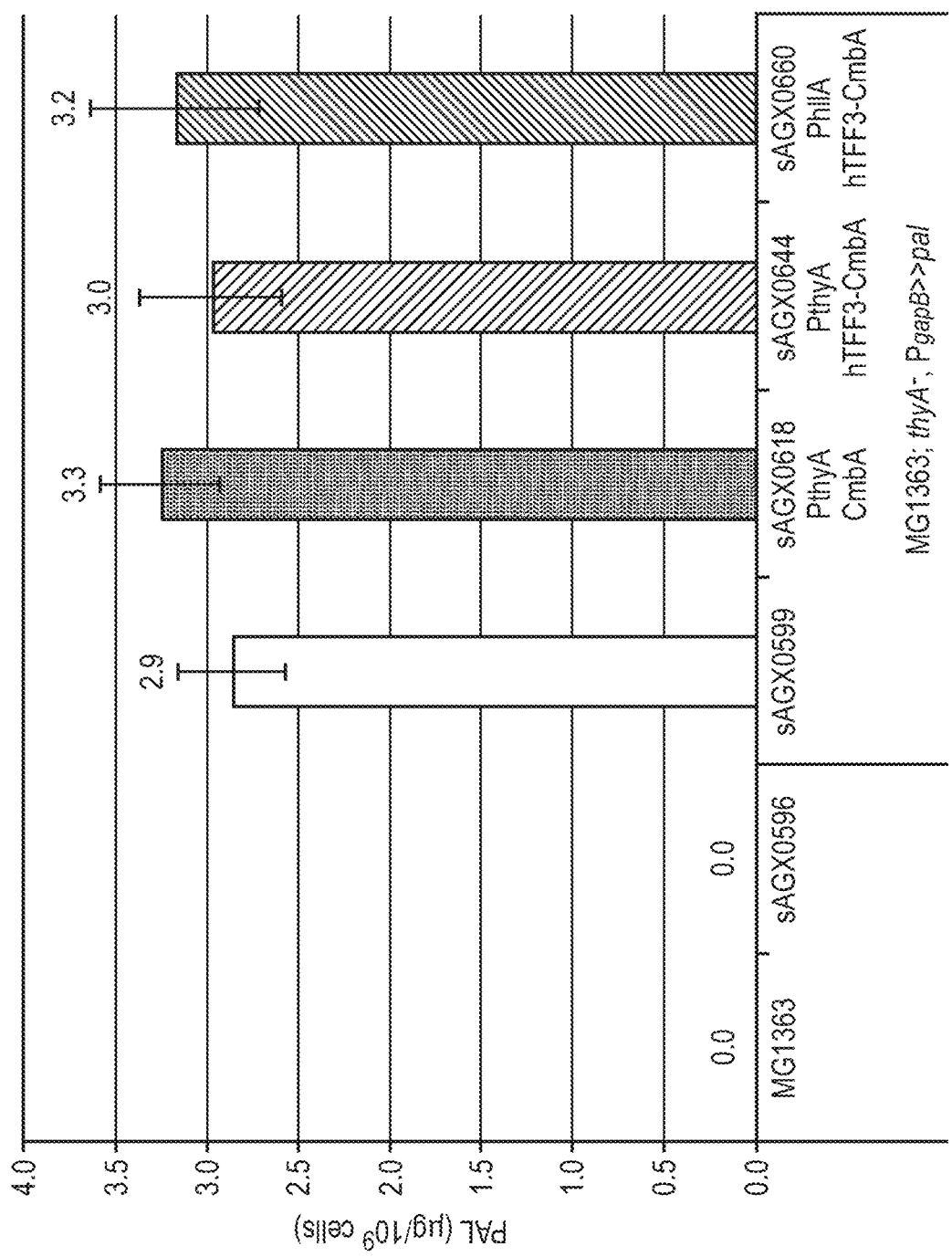

FIG. 8 is a graph illustrating production of an exemplary therapeutic polypeptide (PAL) by bacterial cells either not expressing a mucoadhesive polypeptide (sAGX0599), expressing the exemplary cell adherence polypeptide CmbA (sAGX0618) on the bacterial surface, or the exemplary fusion protein hTFF3-CmbA on the bacterial surface (sAGX0644 (thyA⁻; PthyA>>SSusp45-htff3-cmbA) and sAGX0660 (thyA⁻; PhllA>>SSusp45-htff3-cmbA)). PAL production in µg per $10^9$ cells was found comparable across PAL producing strains.

Figure 9A:
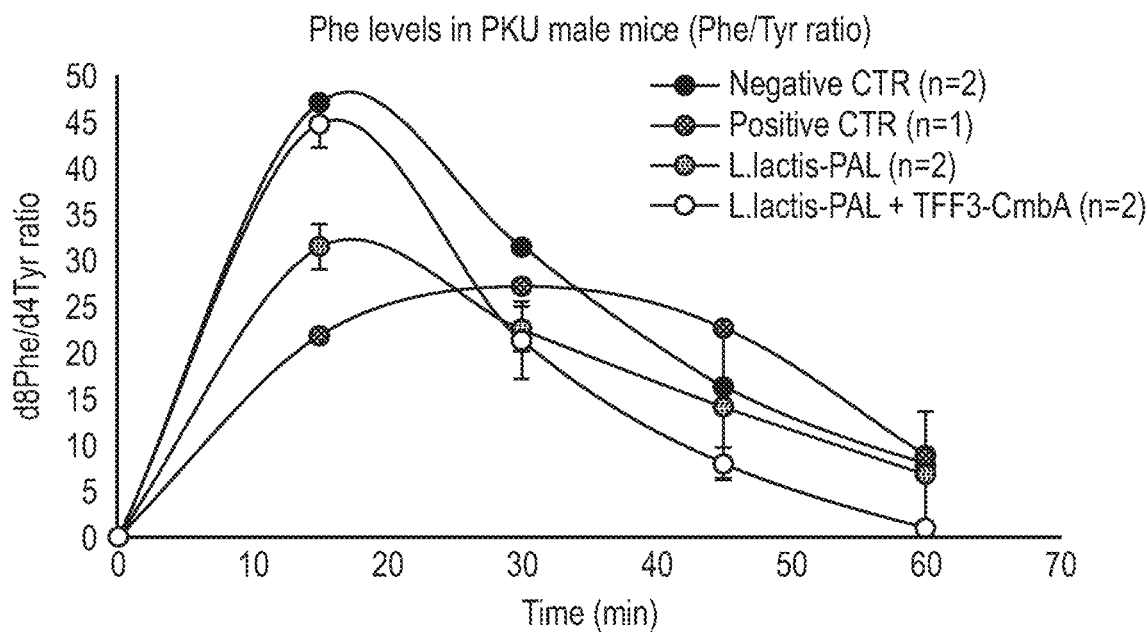
Figure 9B:
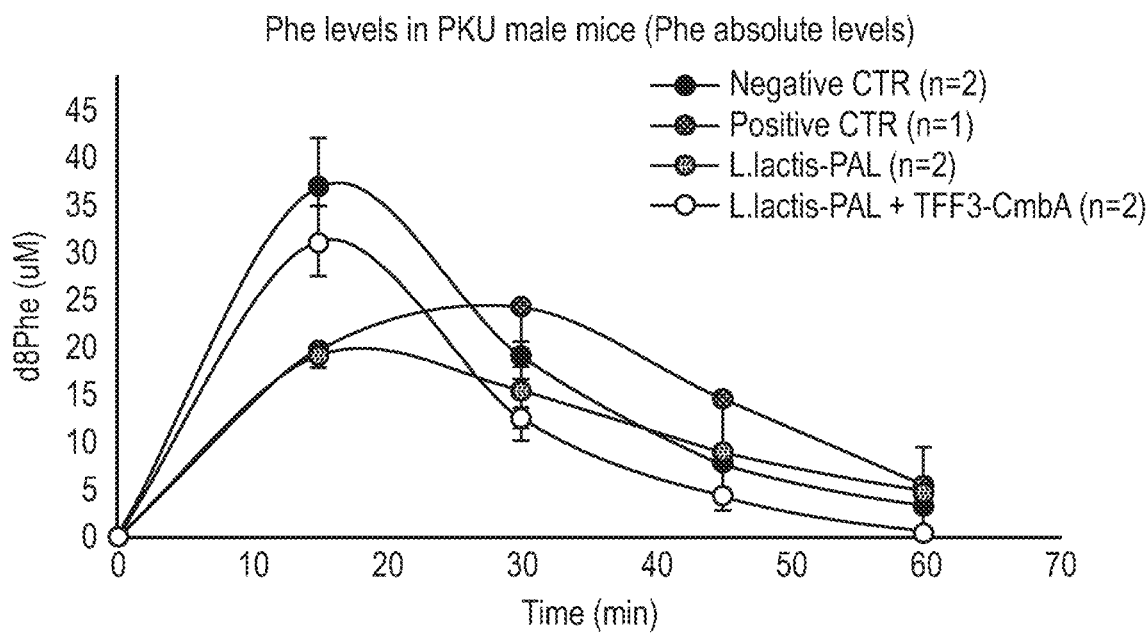
Figure 9C:
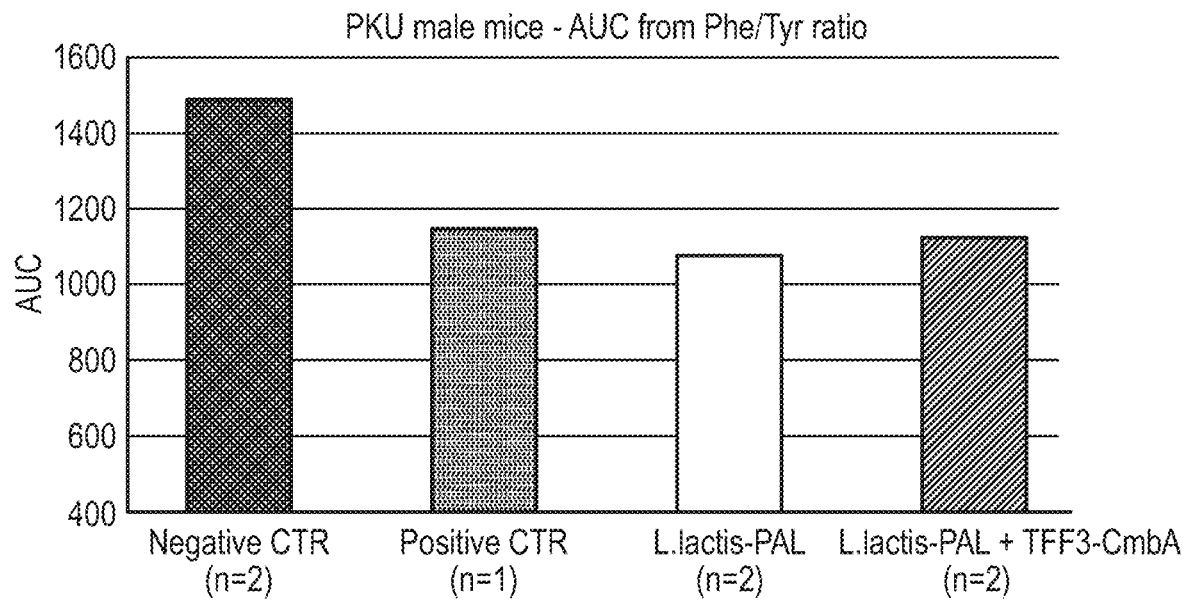
Figure 9D:
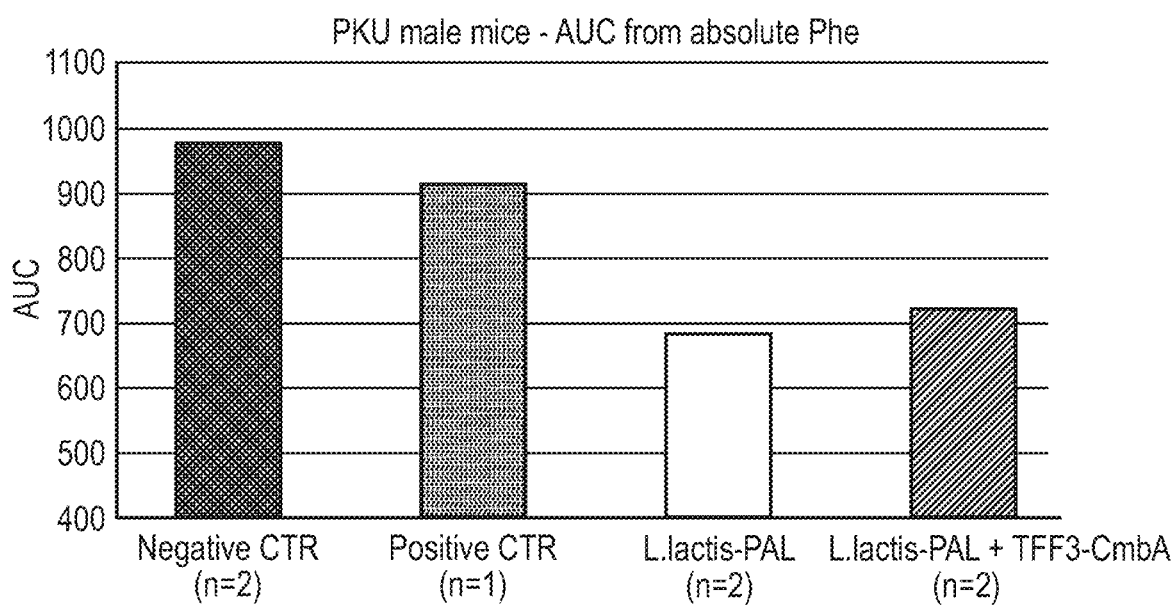

FIGS. 9A-D show that oral administration of *L. lactis* expressing PAL lowers blood concentrations of phenylalanine. Negative CTR=no *lactis*, bolus only; Positive CTR=*L. lactis* strain NZ9000[pAGX1886], nisin induced PAL (AGX No 3151); *L. lactis*-PAL=sAGX0599 (AGX No 2947), secreting PAL; *L. lactis*-PAL+TFF3-CmbA=sAGX0645 mucoadherent strain (AGX No 3290), secreting PAL and with surface TFF3-CmbA, which is cell and mucoadherent. FIGS. 9A-B show the blood levels of Phe and Tyr measured over time following the administration of a bolus of radiolabeled Phe and FIGS. 9C-D show the corresponding AUC. The new constructs are associated with lower levels of blood Phe. The final level of Phe was lowest in mice administered *L. lactis* expressing PAL and the TFF3-CmbA fusion protein.

DETAILED DESCRIPTION

The current disclosure provides microorganisms (e.g., lactic acid bacteria, such as *Lactococcus lactis*) exhibiting enhanced in vitro binding to mucins and enhanced in vitro binding to cells, e.g., adherence to Caco-2 cells. In some embodiments, such microorganisms have an increased GI transit time. For example, such microorganism may additionally express a therapeutic polypeptide. In some examples, upon oral administration of such bacteria to a mammalian subject, residence time of the bacteria in the different parts of the GI-tract is increased, and the subject is exposed to the therapeutic polypeptide in the GI tract for a longer period of time. For example, once the bacteria are released, e.g. from protective coated capsules in the duodenum, residence time of the bacteria in the jejunum and ileum is extended by surface display/expression of muco and cell-adhesive proteins that bind or interact with the intestinal mucosa. Consequently, bacterial doses may be reduced, microorganisms with lower expression profiles become acceptable for administering therapeutically effective doses, smaller unit dosage forms can be developed, and regimens with less frequent administration can be employed (e.g., increasing patient compliance).

For example, the present disclosure provides microorganisms containing an exogenous nucleic acid encoding a fusion protein of human trefoil factor 3 (hTFF3) with cell and mucus binding protein A (CmbA) of *Lactobacillus reuteri* at the surface of *Lactococcus lactis*. An exemplary fusion protein is composed of the secretion signal of *Lactococcus lactis* protein usp45 (see, e.g., Van Asseldonk et al., *Mol. Gen. Genet.* 1993, 240:428-434), fused to hTFF3 (see, e.g., Tomasetto et al., *Gastroenterology* 2000, 118(1):70-80) and *Lactobacillus reuteri* CmbA (e.g., without its secretion signal). The SSusp45-hTFF3-CmbA fusion protein is secreted by way of the usp45 secretion signal and the secretion signal peptide is cleaved when the hTFF3-CmbA fusion protein passes the *Lactococcus lactis* cytoplasmic membrane. The external part of CmbA can bind intestinal epithelial cells. By fusing hTFF3 to the CmbA protein, an additional mucus binding unit is added. Expression and surface display of hTFF3-CmbA enabled increased adherence to the intestinal mucosa and resulted in a slower GI-transit time of the modified *Lactococcus lactis* cells.

Definitions

As used in the specification and claims, the singular forms "a," "an," and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

The term "about" in relation to a reference numerical value, and its grammatical equivalents as used herein, can include the reference numerical value itself and a range of values plus or minus 10% from that reference numerical value. For example, the term "about 10" includes 10 and any amounts from and including 9 to 11. In some cases, the term "about" in relation to a reference numerical value can also include a range of values plus or minus 10%, 9%, 8%, 7%, 6%, 5%, 4%, 3%, 2%, or 1% from that reference numerical value. In some embodiments, "about" in connection with a number or range measured by a particular method indicates that the given numerical value includes values determined by the variability of that method.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The percentage identity of polypeptide sequences can be calculated using commercially available algorithms which compare a reference sequence with a query sequence. In some embodiments, polypeptides are 70%, at least 70%, 75%, at least 75%, 80%, at least 80%, 85%, at least 85%, 90%, at least 90%, 92%, at least 92%, 95%, at least 95%, 97%, at least 97%, 98%, at least 98%, 99%, or at least 99% or 100% identical to a reference polypeptide, or a fragment thereof (e.g., as measured by BLASTP or CLUSTAL, or other alignment software) using default parameters. Similarly, nucleic acids can also be described with reference to a starting nucleic acid, e.g., they can be 50%, at least 50%, 60%, at least 60%, 70%, at least 70%, 75%, at least 75%, 80%, at least 80%, 85%, at least 85%, 90%, at least 90%, 95%, at least 95%, 97%, at least 97%, 98%, at least 98%, 99%, at least 99%, or 100% identical to a reference nucleic acid or a fragment thereof (e.g., as measured by BLASTN or CLUSTAL, or other alignment software using default parameters). When one molecule is said to have a certain percentage of sequence identity with a larger molecule, it means that when the two molecules are optimally aligned, the percentage of residues in the smaller molecule finds a match residue in the larger molecule in accordance with the order by which the two molecules are optimally aligned, and the "%" (percent) identity is calculated in accord with the length of the smaller molecule.

It is to be understood that the expression of a foreign protein in a bacterium typically requires modifications. These include modification of the nucleic acid to remove of introns and other eukaryotic nucleic acid motifs that are not recognized by bacteria, and to optimize codon usage to the host.

Likewise, proteins are modified to remove motifs that are necessary for proper processing in the natural host but are not recognized by the bacterial host, such as secretion signals from eukaryotes or other species of bacteria. Thus, when reference is made to a foreign protein being expressed in bacteria, the person of ordinary skill would understand that to refer to the mature form. For example, human IL-10 is translated in a human cell with a secretion leader sequence that is not present in the mature IL-10 secreted from the cell. The eukaryotic secretion leader sequence is nonfunctional in bacteria. Accordingly, *L. lactis* further comprises nucleic acid expressing "IL-10", it contains the mature IL-10 protein.

As used herein, the term "expressing" a gene or polypeptide or "producing" a polypeptide (e.g., PAL, or an IL-2 polypeptide or T1D-specific antigen polypeptide) is meant to include "capable of expressing" and "capable of producing," respectively. For example, a microorganism, which contains an exogenous nucleic acid can, under sufficient conditions (e.g., sufficient hydration and/or in the presence of nutrients), produce a polypeptide encoded by the exogenous nucleic acid). However, the microorganism may not always actively produce the encoded polypeptide. The microorganism (e.g., bacterium) may be dried (e.g., freeze-dried), and in that state can be considered dormant (i.e., is not actively producing polypeptide). However, once the microorganism is subjected to sufficient conditions, e.g., is administered to a subject and is released (e.g., in the gastro-intestinal tract of the subject) it may begin producing polypeptide. Thus, a microorganism "expressing" a gene or polypeptide or "producing" a polypeptide of the current disclosure includes the microorganism in its "dormant" state.

As used herein, the term "constitutive" in the context of a promoter (or by extension relating to gene expression or secretion of a polypeptide) refers to a promoter that allows for continual transcription of its associated gene.

The term "chromosomally integrated" or "integrated into a chromosome" or any variation thereof means that a nucleic acid sequence (e.g., gene; open reading frame; exogenous nucleic acid encoding a polypeptide; promoter; expression cassette; and the like) is located on (integrated into) a microbial (e.g., bacterial) chromosome, i.e., is not located on an episomal vector, such as a plasmid. In some embodiments, in which the nucleic acid sequence is chromosomally integrated, the polypeptide encoded by such chromosomally integrated nucleic acid is constitutively expressed.

The terms "secretion leader sequence," "secretion leader," and "secretion signal sequence" are used interchangeably herein. The terms are used in accordance with their art recognized meaning, and generally refer to a nucleic acid sequence, which encodes a "signal peptide" or "secretion signal peptide" causes a polypeptide being expressed by a microorganism and comprising the signal peptide to be secreted by the microorganism, i.e., causes the polypeptide to leave the intracellular space, e.g., be secreted into the surrounding medium, or be anchored in the cell wall with at least a portion of the polypeptide be exposed to the surrounding medium, e.g. on the surface of the microorganism.

Therapeutic Polypeptide

The term "therapeutic polypeptide" includes any polypeptide that has a therapeutic, prophylactic, or other biological activity (e.g., in a mammalian subject), or has the potential for eliciting a biological activity. Examples include known biologics (approved and investigational), and any signal polypeptides, such as hormones and cytokines, and their receptors, agonists and antagonists. A "therapeutic polypeptide" may be modified from a corresponding wild-type polypeptide. In some examples, the therapeutic polypeptide is a cytokine, e.g., an interleukin (IL), such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21 or IL-22.

In other examples, the therapeutic polypeptide is an antigen. In some examples according to this embodiment, the antigen is an "auto-antigen" or self-antigen. The terms "self-antigen" or "auto-antigen" are used interchangeably herein. The terms are used herein in accordance with the art recognized meaning of self-antigen or auto-antigen, and generally refer to a polypeptide/protein originating from within a subjects own body (produced by the subject's own body), wherein the antigen is recognized by the subject's own immune system, and typically produces antibodies against such antigen. Autoimmune diseases are generally associated with certain disease-specific self-antigens. For example, in T1D a subject's immune system may produce antibodies against at least one antigen associated with the beta-cell destruction process. In some examples, the auto-antigen is a T1D-specific antigen. Exemplary T1D-specific antigens include proinsulin (PINS), glutamic acid decarboxylase (GAD65), insulinoma-associated protein 2 (IA-2), islet-specific glucose-6-phosphatase catalytic subunit-related protein (IGRP), zinc transporter 8 (ZnT8), and any combinations thereof. Clinical T1D may further be associated with additional candidate target molecules expressed by beta-cells such as chromogranin A, (prepro) islet amyloid polypeptide (ppIAPP), peripherin, and citrullinated glucose-regulated protein (GRP), and any combinations thereof. Exemplary amino acid sequences and nucleic acid sequences for the above T1D-specific antigens are disclosed, e.g., in provisional patent application 62/350,472 (filed Jun. 15, 2016), the disclosure of which is incorporated herein by reference in its entirety. In some examples, the T1D-specific antigen is PINS, such as wild-type human PINS. See, e.g., CDS contained in accession number NM_000207.2, or a sequence that is at least about 60%, at least about 70%, at least about 80%, at least about 90%, at least about 95%, at least about 96%, at least about 97%, at least about 98%, or at least about 99% sequence identity with such wild-type human PINS. Additional exemplary PINS nucleotide sequences are represented by the coding sequences of NCBI accession numbers AY899304 (complete CDS, alternatively spliced); NM_000207 (transcript variant 1); NM_001185097 (transcript variant 2); NM_001185098 (transcript variant 3); NM_001291897 (transcript variant 4), and partial sequences thereof. Exemplary PINS amino acid sequences include those encoded by any one of the above PINS nucleic acid sequences.

In other examples, the antigen is an allergen, such as a tree pollen allergen, a weed pollen allergen, a grass pollen allergen, a food allergen, a dust-mite allergen, a mold allergen, an animal dander allergen, or a combination thereof. In some examples, the allergen is a weed pollen allergen, e.g., a ragweed pollen allergen. In other examples, the allergen is a tree pollen allergen, such as a birch pollen allergen or a Japanese cedar pollen allergen. In yet other examples, the allergen is a food allergen, such as a peanut allergen, a milk allergen, an egg allergen, a gluten allergen (gliadin epitope), or a combination thereof. In other examples the therapeutic polypeptide is an antigen and an interleukin, such as IL-2, IL-10, or IL-22.

In further examples, the therapeutic polypeptide is an antibody or a fragment thereof. For example, the antibody is a single-domain antibody or a nanobody. Exemplary antibodies include cytokine neutralizing antibodies such as antibodies to IL-4, antibodies to IL-5, antibodies to IL-7, antibodies to IL-13, antibodies to IL-15, as well as anti TNFα antibodies, antibodies to immunoglobulin E (IgE), anti-P40, and any fragments thereof.

In yet other examples, the therapeutic polypeptide is an enzyme or a fragment (e.g., functional fragment) thereof, e.g., a phenylalanine ammonia lyase (PAL), an amino acid decarboxylase, or a combination thereof. In one example, the therapeutic polypeptide is PAL, or a functional fragment thereof. Exemplary PAL sequences useful for this embodiment are disclosed, e.g., in International Patent Application Publication WO 2014/066945, the disclosure of which is incorporated herein by reference in its entirety. PAL metabolizes phenylalanine and thereby can reduce the level of Phe absorbed from the gut into the blood, and therefore can be used to treat phenylketonuria. Other enzymes may also be used to degrade Phe, such as the aromatic amino acid decarboxylases, such as phenylalanine decarboxylases. In some embodiments, the subject is administered bacteria that expresses and secretes PAL and second phenylalanine degrading enzyme. In another embodiment the subject is administered a bacteria that expresses and secretes PAL, and another bacteria that expresses and secretes a second phenylalanine degrading enzyme.

In a further example, a bacteria is engineered to enhance Phe uptake and utilization within the cell. Administration of such bacteria can further reduce the amount of Phe absorbed by the patient.

In further examples, the therapeutic polypeptide is a glucagon-like peptide 1 (GLP-1), glucagon-like peptide 2 (GLP-2), glucagon, exendin-4, or any combination thereof. In other examples, the therapeutic polypeptide is a growth factor, such as an epidermal growth factor (EGF), e.g., human EGF or porcine EGF. In yet other examples, the therapeutic polypeptide is a TFF, such as TFF1, TFF2, TFF3, or a combination thereof.

In some examples, the therapeutic polypeptide is an immuno-modulating compound. The terms "immuno-modulating compound" or immuno-modulator" are used herein in accordance with their art-recognized meaning. The immuno-modulating compound can be any immuno-modulating compound known to a person skilled in the art. In some embodiments, the immuno-modulating compound is a tolerance inducing compound. Tolerance induction can be obtained, e.g., by inducing regulatory T-cells, or in an indirect way, e.g., by activation of immature dendritic cells to tolerizing dendritic cells and/or inhibiting Th2 immune response inducing expression of "co-stimulation" factors on mature dendritic cells. Immuno-modulating and immuno-suppressing compounds are known to the person skilled in the art and include, but are not limited to, bacterial metabolites such as spergualin, fungal and streptomycal metabolites such as tacrolimus or ciclosporin, immuno-suppressing cytokines such as IL-4, IL-10, IFNα, TGFβ (as selective adjuvant for regulatory T-cells) Flt3L, TSLP and Rank-L (as selective tolerogenic DC inducers), antibodies and/or antagonist (e.g., antibodies) such as anti-CD40L, anti-CD25, anti-CD20, anti-IgE, anti-CD3, and proteins, peptides or fusion proteins such as the CTL-41 g or CTLA-4 agonist fusion protein. In some embodiments, the immuno-modulating compound is an immuno-suppressing compound. In other embodiments, the immuno-suppressing compound is an immuno-suppressing cytokine or antibody. In other embodiments, the immuno-suppressing cytokine is a tolerance-enhancing cytokine or antibody. It will be appreciated by the person skilled in the art that the term "immuno-modulating compound" also includes functional homologues thereof. A functional homologue is a molecule having essentially the same or similar function for the intended purposes, but can differ structurally. In some examples, the immuno-modulating compound is an anti-CD3 antibody, or a functional homologue thereof.

A microorganism of the present disclosure may express more than one, or at least one therapeutic polypeptide. The therapeutic polypeptide may be a combination of any of the above recited therapeutic polypeptides.

Diseases

The microorganisms (e.g., bacteria), compositions and methods of the present disclosure can be used to treat or prevent any disease, e.g., those which can be treated by a bioactive polypeptide that is active at the site of the mucosa, e.g., gastro-intestinal mucosa. Exemplary diseases that can be treated or prevented using the methods of the present disclosure include autoimmune disease, allergies, nutritional or metabolic diseases, gastro-intestinal diseases, and genetic disorders, or any combinations thereof.

The term "nutritional disease" includes any disease that is associated with an insufficiency to process food or nutrients, and may result, e.g., in malnutrition, low weight, or other secondary conditions (such as bloating). A "nutritional disease" may be associated with insufficient production of certain enzymes that process food or food components, such as lipids and carbohydrates (such as lipases, proteases, or sugar degrading enzymes). The term "nutritional disease" includes any metabolic process in an organism that can be enhanced even if no defined condition or disease is present ("metabolic enhancement"), e.g., certain farm animals, such as pigs, cows, birds, or sheep can be treated to grow faster or accumulate higher weights. In some examples, the "nutritional disease" is an intolerance to certain foods or food components based on insufficient or abnormal metabolism of such food or food component, such as lactose intolerance. The term "nutritional disease" is related to "metabolic disease" or "metabolic disorder" used interchangeably herein. The term "metabolic disease" is used herein in accordance with its art-recognized meaning, and generally refers to any condition, in which abnormal chemical reactions in the body alter a normal metabolic process. In some examples, the metabolic disease is caused by a genetic defect, and may be inherited. Examples of metabolic disorder include acid-base imbalances, metabolic brain diseases, calcium metabolism disorders, DNA repair-deficiency disorders, glucose metabolism disorders, hyperlactatemia, iron metabolism disorders, and lipid metabolism disorders.

Other examples of nutritional or metabolic diseases include glucose and/or galactose malabsorption, Lesch-Nyhan syndrome, Menkes syndrome, obesity, pancreatic cancer, Prader-Willi syndrome, porphyria, Refsum disease, Tangier disease, Wilson's disease, Hurler syndrome (e.g., characterized by abnormal bone structure and developmental delay), Niemann-Pick disease (e.g., in which babies develop liver enlargement, difficulty feeding, and nerve damage), Tay-Sachs disease (e.g., characterized by progressive weakness in a young child, progressing to severe nerve damage), Gaucher disease (e.g., characterized by bone pain, enlarged liver, and low platelet counts); Fabry disease (e.g., characterized by pain in the extremities in childhood, with kidney and heart disease and strokes in adulthood), Krabbe disease (e.g., characterized by progressive nerve damage, developmental delay in young children); galactosemia (e.g., characterized by impaired breakdown of the sugar galactose, can lead to jaundice, vomiting, and liver enlargement after breast or formula feeding by a newborn); maple syrup urine disease (e.g., characterized by deficiency of the enzyme BCKD, causes buildup of amino acids in the body); phenylketonuria (PKU), glycogen storage diseases (e.g., characterized by low blood sugar levels, muscle pain, and weakness); mitochondrial disorders, Friedreich ataxia (e.g., characterized by problems related to the protein frataxin, which may cause nerve damage, heart problems, inability to walk), and peroxisomal disorders (e.g., characterized by poor enzyme function inside peroxisomes, which may lead to buildup of toxic metabolites). Exemplary peroxisomal disorders include, e.g., Zellweger syndrome (e.g., characterized by abnormal facial features, enlarged liver, and nerve damage in infants), and adrenoleukodystrophy (e.g., characterized by symptoms of nerve damage in childhood or early adulthood). Other nutritional or metabolic disorders include metal metabolism disorders (e.g., characterized by protein malfunction and toxic accumulation of metal in the body). Examples include, e.g., Wilson disease (e.g., characterized by accumulation of toxic copper levels in the liver, brain, and other organs), and hemochromatosis (e.g., hereditary hemochromatosis), e.g., in which the intestines absorb excessive iron, which builds up in the liver, pancreas, joints, and heart, causing damage. Further examples of nutritional or metabolic disorders include organic acidemias (such as methylmalonic acidemia and propionic academia), urea cycle disorders (such as ornithine transcarbamylase deficiency and citrullinemia). In some example, the nutritional or metabolic disease is phenylketonuria (PKU). In other examples, the nutritional or metabolic disease is a metabolic disorder related to energy dysregulation (e.g., nonalcoholic steatohepatitis).

In some examples, the disease is an autoimmune disease. Exemplary autoimmune diseases include myocarditis, postmyocardial infarction syndrome, postpericardiotomy syndrome, subacute bacterial endocarditis (SBE), anti-glomerular basement membrane nephritis, interstitial cystitis, lupus nephritis, autoimmune hepatitis, primary biliary cirrhosis (PBC), primary sclerosing cholangitis, antisynthetase syndrome, alopecia areata, autoimmune angioedema, autoimmune progesterone dermatitis, autoimmune urticarial, bullous pemphigoid, cicatricial pemphigoid, dermatitis herpetiformis, discoid lupus erythematosus, epidermolysis bullosa acquisita, erythema nodosum, gestational pemphigoid, hidradenitis suppurativa, lichen planus, lichen sclerosus, linear IgA disease (LAD), morphea, pemphigus vulgaris, pityriasis lichenoides et varioliformis acuta, Mucha-Habermann disease, psoriasis, systemic scleroderma, vitiligo, Addison's disease, autoimmune polyendocrine syndrome (APS) type 1, autoimmune polyendocrine syndrome (APS) type 2, autoimmune polyendocrine syndrome (APS) type 3, autoimmune pancreatitis (AIP), diabetes mellitus type 1, autoimmune thyroiditis, Ord's thyroiditis, Graves' disease, autoimmune oophoritis, endometriosis, autoimmune orchitis, Sjogren's syndrome, autoimmune enteropathy, Coeliac disease, Crohn's disease, microscopic colitis, ulcerative colitis, antiphospholipid syndrome (APS, APLS), aplastic anemia, autoimmune hemolytic anemia, autoimmune lymphoproliferative syndrome, autoimmune neutropenia, autoimmune thrombocytopenic purpura, cold agglutinin disease, essential mixed cryoglobulinemia, Evans syndrome, paroxysmal nocturnal, hemoglobinuria, pernicious anemia, pure red cell aplasia, thrombocytopenia, adiposis dolorosa, adult-onset Still's disease, ankylosing spondylitis, CREST syndrome, drug-induced lupus, enthesitis-related arthritis, eosinophilic fasciitis, Felty syndrome, IgG4-related disease, juvenile arthritis, Lyme disease (chronic), mixed connective tissue disease (MCTD), palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, Schnitzler syndrome, systemic lupus erythematosus (SLE), undifferentiated connective tissue disease (UCTD), dermatomyositis, fibromyalgia, inclusion body myositis, myositis, myasthenia gravis, neuromyotonia, paraneoplastic cerebellar degeneration, polymyositis, acute disseminated encephalomyelitis (ADEM), acute motor axonal neuropathy, anti-N-methyl-D-aspartate (anti-NMDA) receptor encephalitis, balo concentric sclerosis, Bickerstaff's encephalitis, chronic inflammatory demyelinating polyneuropathy, Guillain-Barré syndrome, Hashimoto's encephalopathy, idiopathic inflammatory demyelinating diseases, Lambert-Eaton myasthenic syndrome, multiple sclerosis (MS), pattern II, Oshtoran Syndrome, pediatric autoimmune neuropsychiatric disorder associated with *Streptococcus* (PANDAS), progressive inflammatory neuropathy, restless leg syndrome, stiff person syndrome, Sydenham chorea, transverse myelitis, autoimmune retinopathy, autoimmune uveitis, Cogan syndrome, Graves ophthalmopathy, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, autoimmune inner ear disease (AIED), Ménière's disease, Behçet's disease, eosinophilic granulomatosis with polyangiitis (EGPA), giant cell arteritis, granulomatosis with polyangiitis (GPA), IgA vasculitis (IgAV), Kawasaki's disease, leukocytoclastic vasculitis, lupus vasculitis, rheumatoid vasculitis, microscopic polyangiitis (MPA), polyarteritis nodosa (PAN), polymyalgia rheumatic, urticarial vasculitis, vasculitis, and primary immune deficiency. In some examples, the autoimmune disease is type-1 diabetes (T1D).

In other examples, the disease is a gastro-intestinal disease, such as short bowel syndrome, celiac disease, or inflammatory bowel disease (IBD), e.g., Crohn's disease or ulcerative colitis.

In some examples, the disease is an inflammatory disease (e.g., Th2 and/or IgE driven inflammation). Exemplary inflammatory diseases include acne vulgaris, asthma, autoinflammatory diseases, chronic prostatitis, glomerulonephritis, hypersensitivities, inflammatory bowel diseases (IBD), pelvic inflammatory disease, reperfusion injury, rheumatic fever, rheumatoid arthritis, sarcoidosis, transplant rejection, graft-versus-host disease, vasculitis, hydradenitis suppurativa, diverticulitis, interstitial cystitis. Examples of autoinflammatory diseases include familial Mediterranean fever (FMF), hyperimmunoglobulinemia D with recurrent fever (HIDS), mevalonic aciduria, mevalonate kinase deficiency, TNF receptor associated periodic syndrome (TRAPS), Muckle-Wells syndrome (urticaria deafness amyloidosis), familial cold urticarial, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum, acne (PAPA), deficiency of the interleukin-1-receptor antagonist (DIRA).

In further examples, the disease is growth retardation. In other examples, the disease is type-2 diabetes (T2D), obesity, or pain (e.g., neuropathic pain).

In other examples, the disease is an allergy, e.g., an allergy to an allergen selected from a tree pollen allergen, a weed pollen allergen, a grass pollen allergen, a food allergen, a dust-mite allergen, a mold allergen, an animal dander allergen, or a combination thereof. In some examples, the disease is an allergy to a weed pollen allergen, e.g., a ragweed pollen allergen. In other examples, the disease is an allergy to a tree pollen allergen, such as a birch pollen allergen or a Japanese cedar pollen allergen. In yet other examples, the disease is an allergy to a food allergen, such as a peanut allergen, a milk allergen, an egg allergen, a gluten allergen (gliadin epitope), or a combination thereof.

Phenylketonuria

In some examples, the present disclosure provides methods for the treatment of phenylketonuria (PKU). The term "phenylketonuria" is used herein in accordance with its art-recognized meaning. Phenylketonuria (PKU) is one of the most prevalent disorders of amino acid metabolism. Genetic defects (deficiency of the enzyme PAH) result in high levels of blood phenylalanine (Phe), which can lead to severe mental retardation if not recognized, and treated early in life. Even with dietary compliance, PKU patients risk cognitive impairment from adolescence onward.

Promoter

By "promoter" is meant generally a region on a nucleic acid molecule, for example DNA molecule, to which an RNA polymerase binds and initiates transcription. A promoter is for example, positioned upstream, i.e., 5', of the sequence the transcription of which it controls. The skilled person will appreciate that the promoter may be associated with additional native regulatory sequences or regions, e.g. operators. The precise nature of the regulatory regions needed for expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the Pribnow-box (cf. TATA-box), Shine-Dalgarno sequence, and the like.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences. For example, a promoter is said to be operably linked to a gene, open reading frame or coding sequence, if the linkage or connection allows or effects transcription of said gene. In a further example, a 5' and a 3' gene, cistron, open reading frame or coding sequence are said to be operably linked in a polycistronic expression unit, if the linkage or connection allows or effects translation of at least the 3' gene. For example, DNA sequences, such as, e.g., a promoter and an open reading frame, are said to be operably linked if the nature of the linkage between the sequences does not (1) result in the introduction of a frameshift mutation, (2) interfere with the ability of the promoter to direct the transcription of the open reading frame, or (3) interfere with the ability of the open reading frame to be transcribed by the promoter region sequence.

Expression Cassette

The term "expression cassette" or "expression unit" is used in accordance with its generally accepted meaning in the art, and refers to a nucleic acid containing one or more genes and sequences controlling the expression of the one or more genes. Exemplary expression cassettes contain at least one promoter sequence and at least one open reading frame.

Polycistronic Expression Cassette

The terms "polycistronic expression cassette," "polycistronic expression unit," or "polycistronic expression system" are used herein interchangeably and in accordance with their generally accepted meaning in the art. They refer to a nucleic acid sequence wherein the expression of two or more genes is regulated by common regulatory mechanisms, such as promoters, operators, and the like. The term polycistronic expression unit as used herein is synonymous with multicistronic expression unit. Examples of polycistronic expression units are without limitation bicistronic, tricistronic, tetracistronic expression units. Any mRNA comprising two or more, such as 3, 4, 5, 6, 7, 8, 9, 10, or more, open reading frames or coding regions encoding individual expression products such as proteins, polypeptides and/or peptides is encompassed within the term polycistronic. A polycistronic expression cassette includes at least one promoter, and at least two open reading frames controlled by the promoter, wherein an intergenic region is optionally placed between the two open reading frames.

In some example, the "polycistronic expression cassette" includes one or more endogenous genes and one or more exogenous genes that are transcriptionally controlled by a promoter which is endogenous to the microorganism (e.g., LAB). In another embodiment, the polycistronic expression unit or system as described herein is transcriptionally controlled by a promoter which is exogenous to the microorganism (e.g., LAB). In a further embodiment, the translationally or transcriptionally coupled one or more endogenous genes and one or more exogenous genes as described herein are transcriptionally controlled by the native promoter of (one of) said one or more endogenous genes. In another embodiment, the polycistronic expression unit is transcriptionally controlled by the native promoter of (one of) said one or more endogenous genes comprised in said polycistronic expression unit. In another embodiment, the polycistronic expression unit is operably linked to a Gram-positive endogenous promoter. In an exemplary embodiment, the promoter may be positioned upstream of, i.e., 5' of the open reading frame(s) to which it is operably linked. In a further embodiment, the promoter is the native promoter of the 5' most, i.e., most upstream, endogenous gene in the polycistronic expression unit. Accordingly, in some examples, the polycistronic expression unit contains an endogenous gene and one or more exogenous genes transcriptionally coupled to the 3' end of said one or more endogenous gene, for example wherein said one or more exogenous gene(s) is (are) the most 3' gene(s) of the polycistronic expression unit.

As used herein, the term "translationally coupled" is synonymous with "translationally linked" or "translationally connected". These terms in essence relate to polycistronic expression cassettes or units. Two or more genes, open reading frames or coding sequences are said to be translationally coupled when common regulatory element(s) such as in particular a common promoter effects the transcription of said two or more genes as one mRNA encoding said two or more genes, open reading frames or coding sequences, which can be subsequently translated into two or more individual polypeptide sequences. The skilled person will appreciate that bacterial operons are naturally occurring polycistronic expression systems or units in which two or more genes are translationally or transcriptionally coupled.

Intergenic Region

As used herein, the term "intergenic region" is synonymous with "intergenic linker" or "intergenic spacer". An intergenic region is defined as a polynucleic acid sequence between adjacent (i.e., located on the same polynucleic acid sequence) genes, open reading frames, cistrons or coding sequences. By extension, the intergenic region can include the stop codon of the 5' gene and/or the start codon of the 3' gene which are linked by said intergenic region. As defined herein, the term intergenic region specifically relates to intergenic regions between adjacent genes in a polycistronic expression unit. For example, an intergenic region as defined herein can be found between adjacent genes in an operon. Accordingly, in an embodiment, the intergenic region as defined herein is an operon intergenic region.

In some examples, the intergenic region, linker or spacer is selected from intergenic regions preceding, i.e., 5' to, more particularly immediately 5' to, rplW, rpl P, rpmD, rplB, rpsG, rpsE or rplN of a Gram-positive bacterium. In some embodiments, the Gram-positive bacterium is a lactic acid bacterium, for example a *Lactococcus* species, e.g., *Lactococcus lactis*, and any subspecies or strain thereof. In an embodiment, said intergenic region encompasses the start codon of rplW, rpl P, rpmD, rplB, rpsG, rpsE or rplN and/or the stop codon of the preceding, i.e. 5', gene. In some embodiments, the invention relates to a Gram-positive bacterium or a recombinant nucleic acid as described herein, wherein the endogenous gene and the one or more exogenous genes are transcriptionally coupled by intergenic region or regions active in the Gram-positive bacterium, for example wherein the intergenic region or regions is endogenous to said Gram-positive bacterium, for example, wherein the endogenous intergenic region is selected from intergenic regions preceding rplW, rpl P, rpmD, rplB, rpsG, rpsE or rplN rplM, rplE, and rplF.

The skilled person will appreciate that if the intergenic region encompasses a 5' stop codon and/or a 3' start codon, these respective codons in some cases are not present in the genes which are linked by said intergenic regions, in order to avoid double start and/or stop codons, which may affect correct translation initiation and/or termination. Methods for identifying intergenic regions are known in the art. By means of further guidance, intergenic regions can for instance be identified based on prediction of operons, and associated promoters and open reading frames, for which software is known and available in the art. Exemplary intergenic regions are described in international patent application publication WO2012/164083, the disclosure of which is incorporated herein by reference in its entirety.

Subject

A "subject" is an organism, which may benefit from being administered a composition of the present disclosure, e.g., according to methods of the present disclosure. The subject may be a mammal ("mammalian subject"). Exemplary mammalian subjects include humans, farm animals (such as cows, pigs, horses, sheep, goats), pets (such as a dogs, cats, and rabbits), and other animals, such as mice, rats, and primates. In some examples, the mammalian subject is a human patient.

Mucosa

The term "mucosa" or "mucous membrane" is used herein in accordance with its art recognized meaning. The "mucosa" can be any mucosa found in the body, such as oral mucosa, rectal mucosa, gastric mucosa, intestinal mucosa, urethral mucosa, vaginal mucosa, ocular mucosa, buccal mucosa, bronchial or pulmonary mucosa, and nasal or olfactory mucosa. Mucosa may also refer to surface mucosa, e.g., those found in fish and amphibia.

The term "mucosal delivery" as used herein is used in accordance with its art recognized meaning, i.e., delivery to the mucosa, e.g., via contacting a composition of the present disclosure with a mucosa. Oral mucosal delivery includes buccal, sublingual and gingival routes of delivery. Accordingly, in some embodiments, "mucosal delivery" includes gastric delivery, intestinal delivery, rectal delivery, buccal delivery, pulmonary delivery, ocular delivery, nasal delivery, vaginal delivery and oral delivery. The person of ordinary skill will understand that oral delivery can affect delivery to distal portions of the gastrointestinal tract.

The term "mucosal tolerance" refers to the inhibition of specific immune responsiveness to an antigen in a mammalian subject (e.g., a human patient), after the subject has been exposed to the antigen via the mucosal route. In some cases the mucosal tolerance is systemic tolerance. Low dose oral tolerance is oral tolerance induced by low doses of antigens, and is characterized by active immune suppression, mediated by cyclophosphamide sensitive regulatory T-cells that can transfer tolerance to naive hosts. High dose oral tolerance is oral tolerance induced by high doses of antigens, is insensitive to cyclophosphamide treatment, and proceeds to induction of T cell hyporesponsiveness via anergy and/or deletion of antigen specific T-cells. The difference in sensitivity to cyclophosphamide can be used to make a distinction between low dose and high dose tolerance (Strobel et al., 1983). In some cases, the oral tolerance is low dose oral tolerance as described by Mayer and Shao (2004).

Mucin

The term "mucin" is used herein in accordance with its art-recognized meaning. Mucins are a family of high molecular weight, glycosylated proteins (glycoconjugates) produced by epithelial tissues in humans and animals. Mucins have the ability to form gels, and are a key component of gel-like secretions. Some mucins are membrane-bound due to the presence of a hydrophobic membrane-spanning domain. Most mucins are secreted as principal components of mucus by mucous membranes or are secreted to become a component of saliva. Mucin genes include MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, and MUC21. MUC2 is secreted mostly in the intestine but also in the airway. Mature mucins are composed of two distinct regions: amino- and carboxy-terminal regions are lightly glycosylated, but rich in cysteines. The cysteine residues participate in establishing disulfide linkages within and among mucin monomers. A large central region formed of multiple tandem repeats of 10 to 80 residue sequences in which up to half of the amino acids are serine or threonine. This area becomes saturated with mostly O-linked oligosaccharides. Overexpression of mucin proteins (e.g., MUC1) is associated with many types of cancer. In the context of this disclosure "mucin" may also mean "mucin preparation" or "mucous or other preparation containing mucins."

Treating

The terms "treatment", "treating", and the like, as used herein means ameliorating or alleviating characteristic symptoms or manifestations of a disease or condition, e.g., PKU or T1D. For example, treatment of T1D can result in the restoration or induction of antigen-specific immune tolerance in the subject. In other examples, treatment means arresting autoimmune diabetes, or reversing autoimmune diabetes. As used herein these terms also encompass, preventing or delaying the onset of a disease or condition or of symptoms associated with a disease or condition, including reducing the severity of a disease or condition or symptoms associated therewith prior to affliction with said disease or condition. Such prevention or reduction prior to affliction refers to administration of the microorganism (e.g., bacterium) or composition of the present disclosure to a patient that is not at the time of administration afflicted with the disease or condition. "Preventing" also encompasses preventing the recurrence or relapse-prevention of a disease or condition or of symptoms associated therewith, for instance after a period of improvement.

Treatment of a subject "in need thereof" conveys that the subject has a diseases or condition, and the therapeutic method of the invention is performed with the intentional purpose of treating the specific disease or condition.

Therapeutically Effective Amount

As used herein, the term "therapeutically effective amount" refers to an amount of a non-pathogenic microorganism or a composition of the present disclosure that will elicit a desired therapeutic effect or response when administered according to the desired treatment regimen. In some examples, the compounds or compositions are provided in a unit dosage form, for example a tablet or capsule, which contains an amount of the active component equivalent with the therapeutically effective amount when administered once, or multiple times per day.

A person of ordinary skill in the art will appreciate that a therapeutically effective amount of a recombinant microorganism, which is required to achieve a desired therapeutic effect (e.g., for the effective treatment of T1D), will vary, e.g., depending on the nature of the polypeptide expressed by the microorganism, the route of administration, and the age, weight, and other characteristics of the recipient.

The amount of secreted polypeptide can be determined based on cfu, determined by state of the art methods such as Q-PCR, or by using ELISA. For example, a particular microorganism may secrete at least about 1 ng to about 1 µg of active polypeptide per $10^9$ cfu. Based thereon, the skilled person can calculate the range of antigen polypeptide secreted at other cfu doses.

Therapeutically effective amounts may be administered in connection with any dosing regimen as described herein. The daily dose of active polypeptide may be administered in 1, 2, 3, 4, 5, or 6 portions throughout the day. Further the daily doses may be administered for any number of days, with any number of rest periods between administration periods. For example, a dose of the active agent (e.g. interleukin) of from about 0.01 to about 3.0 M IU/day/subject may be administered every other day for a total of 6 weeks. In other examples, PAL is administered at doses ranging from 0.1 to 1000 mg per day, such as doses of 1-100 mg at each meal.

T1D-Specific Antigen

In some embodiments, in any of the above compositions and methods, the T1D-specific antigen is selected from known auto-antigens implemented in T1D, and include proinsulin (PINS); insulin (INS); glutamic acid decarboxylase (GAD) (e.g., GAD65, GAD67, or GAD2); insulinoma-associated protein 2 (islet antigen-2; IA-2) (also referred to as protein tyrosine phosphatase, receptor type, N (PTPRN), tyrosine phosphatase-like protein, or ICA512), (see, e.g., Long et al., *Diabetes* 2013, 62 (6), 2067-2071); islet-specific glucose-6-phosphatase catalytic subunit-related protein (IGRP), zinc transporter 8 (ZnT8), chromogranin A, (prepro) islet amyloid polypeptide (ppIAPP), peripherin, citrullinated glucose-regulated protein (e.g., GRP78); see, e.g., Rondas et al., *Diabetes* 2015; 64(2):573-586; and Ye et al., *Diabetes* 2010, 59(1):6-16), and combinations of two or more of these antigens. In other embodiments, in the above compositions and methods, the T1D-specific antigen is PINS, GAD65, or IA-2. In other embodiments, in the above compositions and methods, the T1D-specific antigen is PINS. In various embodiments, the T1D-specific antigen is encoded by a variant nucleic acid sequence shorter than a full length (e.g., wild-type) gene, as such "trimmed" versions are often more efficiently expressed and/or secreted by the microorganisms used (e.g., *Lactococcus lactis*). While secretion is more efficient, many "trimmed" versions retain all (or a substantial portion) of their biological activity, e.g., retain sufficient Treg stimulating and/or tolerance-inducing capacities.

Microorganism

In some examples according to any of the embodiments presented herein, the microorganism is a non-pathogenic microorganism, e.g., a non-pathogenic and non-invasive bacterium. In other embodiments, the microorganism is a non-pathogenic and non-invasive yeast.

In some embodiments, the microorganism is a yeast strain selected from the group consisting of *Saccharomyces* sp., *Hansenula* sp., *Kluyveromyces* sp., *Schizzosaccharomyces* sp. *Zygosaccharomyces* sp., *Pichia* sp., *Monascus* sp., *Geothchum* sp. and *Yarrowia* sp. In some embodiments, the yeast is *Saccharomyces cerevisiae*. In other embodiments, the *S. cerevisiae* is of the subspecies *boulardii*. In one embodiment of the present invention, the recombinant yeast host-vector system is a biologically contained system. Biological containment is known to the person skilled in the art and can be realized by the introduction of an auxotrophic mutation, e.g., a suicidal auxotrophic mutation such as the thyA mutation, or its equivalents. Alternatively, the biological containment can be realized at the level of the plasmid carrying the gene encoding the polypeptide, such as, for example, by using an unstable episomal construct, which is lost after a few generations. Several levels of containment, such as plasmid instability and auxotrophy, can be combined to ensure a high level of containment, if desired.

In other embodiments of the present invention, the microorganism is a bacterium, such as a non-pathogenic bacterium, e.g., a food grade bacterial strain. In some examples, the non-pathogenic bacterium is a Gram-positive bacterium, e.g., a Gram-positive food-grade bacterial strain. In some embodiments, the Gram-positive food-grade bacterial strain is a lactic acid fermenting bacterial strain (i.e., a lactic acid bacterium (LAB)) or a *Bifidobacterium*.

In some embodiments, the lactic acid fermenting bacterial strain is a *Lactococcus*, *Lactobacillus* or *Bifidobacterium* species. As used herein, *Lactococcus* or *Lactobacillus* is not limited to a particular species or subspecies, but meant to include any of the *Lactococcus* or *Lactobacillus* species or subspecies. Exemplary *Lactococcus* species include *Lactococcus garvieae*, *Lactococcus lactis*, *Lactococcus piscium*, *Lactococcus plantarum*, and *Lactococcus raffinolactis*. In some examples, the *Lactococcus lactis* is *Lactococcus lactis* subsp. *cremoris*, *Lactococcus lactis* subsp. *hordniae*, or *Lactococcus lactis* subsp. *lactis*.

Exemplary *Lactobacillus* species include *Lactobacillus acetotolerans*, *Lactobacillus acidophilus*, *Lactobacillus agilis*, *Lactobacillus algidus*, *Lactobacillus alimentarius*, *Lactobacillus amylolyticus*, *Lactobacillus amylophilus*, *Lactobacillus amylovorus*, *Lactobacillus animalis*, *Lactobacillus aviarius*, *Lactobacillus aviarius* subsp. *araffinosus*, *Lactobacillus aviarius* subsp. *aviarius*, *Lactobacillus bavaricus*, *Lactobacillus bifermentans*, *Lactobacillus brevis*, *Lactobacillus buchneri*, *Lactobacillus bulgaricus*, *Lactobacillus carnis*, *Lactobacillus casei*, *Lactobacillus casei* subsp. *alactosus*, *Lactobacillus casei* subsp. *casei*, *Lactobacillus casei* subsp. *pseudoplantarum*, *Lactobacillus casei* subsp. *rhamnosus*, *Lactobacillus casei* subsp. *tolerans*, *Lactobacillus catenaformis*, *Lactobacillus cellobiosus*, *Lactobacillus collinoides*, *Lactobacillus confusus*, *Lactobacillus coryniformis*, *Lactobacillus coryniformis* subsp. *coryniformis*, *Lactobacillus coryniformis* subsp. *torquens*, *Lactobacillus crispatus*, *Lactobacillus curvatus*, *Lactobacillus curvatus* subsp. *curvatus*, *Lactobacillus curvatus* subsp. *melibiosus*, *Lactobacillus delbrueckii*, *Lactobacillus delbrueckii* subsp. *bulgaricus*, *Lactobacillus delbrueckii* subsp. *delbrueckii*, *Lactobacillus delbrueckii* subsp. *lactis*, *Lactobacillus divergens*, *Lactobacillus farciminis*, *Lactobacillus fermentum*, *Lactobacillus fornicalis*, *Lactobacillus fructivorans*, *Lactobacillus fructosus*, *Lactobacillus gallinarum*, *Lactobacillus gasseri*, *Lactobacillus graminis*, *Lactobacillus halotolerans*, *Lactobacillus hamsteri*, *Lactobacillus helveticus*, *Lactobacillus heterohiochii*, *Lactobacillus hilgardii*, *Lactobacillus homohiochii*, *Lactobacillus iners*, *Lactobacillus intestinalis*, *Lactobacillus jensenii*, *Lactobacillus johnsonii*, *Lactobacillus kandleri*, *Lactobacillus kefiri*, *Lactobacillus kefiranofaciens*, *Lactobacillus kefirgranum*, *Lactobacillus kunkeei*, *Lactobacillus lactis*, *Lactobacillus leichmannii*, *Lactobacillus lindneri*, *Lactobacillus malefermentans*, *Lactobacillus mali*, *Lactobacillus maltaromicus*, *Lactobacillus manihotivorans*, *Lactobacillus minor*, *Lactobacillus minutus*, *Lactobacillus mucosae*, *Lactobacillus murinus*, *Lactobacillus nagelii*, *Lactobacillus oris*, *Lactobacillus panis*, *Lactobacillus parabuchneri*, *Lactobacillus paracasei*, *Lactobacillus paracasei* subsp. *paracasei*, *Lactobacillus paracasei* subsp. *tolerans*, *Lactobacillus parakefiri*, *Lactobacillus paralimentarius*, *Lactobacillus paraplantarum*, *Lactobacillus pentosus*, *Lactobacillus perolens*, *Lactobacillus piscicola*, *Lactobacillus plantarum*, *Lactobacillus pontis*, *Lactobacillus reuteri*, *Lactobacillus rhamnosus*, *Lactobacillus rimae*, *Lactobacillus rogosae*, *Lactobacillus ruminis*, *Lactobacillus sakei*, *Lactobacillus sakei* subsp. *camosus*, *Lactobacillus sakei* subsp. *sakei*, *Lactobacillus salivarius*, *Lactobacillus salivarius* subsp. *salicinius*, *Lactobacillus salivarius* subsp. *salivarius*, *Lactobacillus sanfranciscensis*, *Lactobacillus sharpeae*, *Lactobacillus suebicus*, *Lactobacillus trichodes*, *Lactobacillus uli*, *Lactobacillus vaccinostercus*, *Lactobacillus vaginalis*, *Lactobacillus viridescens*, *Lactobacillus vitulinus*, *Lactobacillus xylosus*, *Lactobacillus yamanashiensis*, *Lactobacillus yamanashiensis* subsp. *mali*, *Lactobacillus yamanashiensis* subsp. *yamanashiensis*, *Lactobacillus zeae*, *Bifidobacterium adolescentis*, *Bifidobacterium angulatum*, *Bifidobacterium bifidum*, *Bifidobacterium breve*, *Bifidobacterium catenulatum*, *Bifidobacterium longum*, and *Bifidobacterium infantis*. In some examples, the LAB is *Lactococcus lactis* (LL).

In further examples, the bacterium is selected from the group consisting of *Enterococcus alcedinis*, *Enterococcus aquimarinus*, *Enterococcus asini*, *Enterococcus avium*, *Enterococcus caccae*, *Enterococcus camelliae*, *Enterococcus canintestini*, *Enterococcus canis*, *Enterococcus casseliflavus*, *Enterococcus cecorum*, *Enterococcus columbae*, *Enterococcus devriesei*, *Enterococcus diestrammenae*, *Enterococcus dispar*, *Enterococcus durans*, *Enterococcus*

*eurekensis, Enterococcus faecalis, Enterococcus faecium, Enterococcus gallinarum, Enterococcus gilvus, Enterococcus haemoperoxidus, Enterococcus hermanniensis, Enterococcus hirae, Enterococcus italicus, Enterococcus lactis, Enterococcus lemanii, Enterococcus malodoratus, Enterococcus moraviensis, Enterococcus mundtii, Enterococcus olivae, Enterococcus pallens, Enterococcus phoeniculicola, Enterococcus plantarum, Enterococcus pseudoavium, Enterococcus quebecensis, Enterococcus raffinosus, Enterococcus ratti, Enterococcus rivorum, Enterococcus rotai, Enterococcus saccharolyticus, Enterococcus silesiacus, Enterococcus solitarius, Enterococcus sulfureus, Enterococcus termitis, Enterococcus thailandicus, Enterococcus ureasiticus, Enterococcus ureilyticus, Enterococcus viikkiensis, Enterococcus villorum*, and *Enterococcus xiangfangensis*, In further examples, the bacterium is selected from the group consisting of *Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus milleri, Streptococcus mitis, Streptococcus mutans, Streptococcus oralis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus viridans,* and *Streptococcus zooepidemicus*.

In a particular aspect of the present invention, the Gram-positive food grade bacterial strain is *Lactococcus lactis* or any of its subspecies, including *Lactococcus lactis* subsp. *cremoris, Lactococcus lactis* subsp. *hordniae*, and *Lactococcus lactis* subsp. *lactis*. In another aspect of the present invention, the recombinant Gram-positive bacterial strains is a biologically contained system, such as the plasmid free *Lactococcus lactis* strain MG1363, that lost the ability of normal growth and acid production in milk (Gasson, M. J. (1983) *J. Bacteriol.* 154:1-9); or the threonine- and pyrimidine-auxotroph derivative *L. lactis* strains (Sorensen et al. (2000) *Appl. Environ. Microbiol.* 66:1253-1258; Glenting et al. (2002) 68:5051-5056).

In some examples according to any of the above embodiments, the bacterium is not *E. coli*.

In one embodiment of the present invention, the recombinant bacterial host-vector system is a biologically contained system. Biological containment is known to the person skilled in the art and can be realized by the introduction of an auxotrophic mutation, e.g., a suicidal auxotrophic mutation such as the thyA mutation, or its equivalents. Alternatively, the biological containment can be realized at the level of the plasmid carrying the gene encoding a polypeptide, such as, for example, by using an unstable episomal construct, which is lost after a few generations. Several levels of containment, such as plasmid instability and auxotrophy, can be combined to ensure a high level of containment, if desired.

Binding and Adherence Molecules

The terms "binding" and "adherence" are largely synonymous herein. Binding/adherence may be assessed through in vitro models with mammalian cells and/or biological surfaces such as mucus, fibronectin, collagen or other inanimate surfaces; and in vivo through, e.g., measurements of colonization, persistence, or as implied by biological effect.

Such binding/adherence is typically specific to a target molecule, cell, or site. Organisms may produce a wide variety of molecules (often polypeptides, glycoproteins and carbohydrates) that facilitate binding and adherence to other cells, inanimate objects, and cellular products such as mucus. Such molecules that facilitate binding and adherence have various degrees of specificity to a target molecule, typically another protein, glycoprotein or carbohydrate. The expression of different binding molecules leads to preferential binding to different biological surfaces. For example, the different cells of the GI tract express different surface molecules, and the frequency of specific surface molecules can differ along the GI tract. Thus, a bacterial cell can preferentially bind to a specific host cell, or a specific region of the GI tract. Binding may be associated with increased colonization, delivery of target proteins at the target site, increased GI transit time and more. Conversely, binding to one site in the GI tract may be associated with reduced binding to another GI site.

The natural variation of bacterial binding proteins can be supplemented by mutation, and by recombination to express motifs from other binding molecules, including from other organisms. Such recombinant binding proteins may be expressed alone, or as a fusion proteins to provide multiple binding specificities in a single molecule.

For a protein to bind the bacterium to a biological surface, the binding polypeptide is typically exported from the cytoplasm and anchored to the surface of the bacterium. In gram positive bacteria, such as *Lactococcus*, adhesion molecules are typically expressed with (a) an N-terminal secretion signal to direct secretion through the cytoplasmic membrane and (b) a C-terminal anchoring domain that anchors the polypeptide to the cell wall (i.e., a "cell wall anchoring domain"). Without an anchoring domain, the polypeptide is released in the extracellular milieu.

For example, the trefoil factors (TFF) are secreted by animal cells, bind to mucus, and have a number of biological effects, including healing the mucus membrane. A bacterium can be engineered to secrete TFF into the extracellular milieu to promote healing of the mucus membrane, by recombinantly adding a bacterial secretion signal to TFF. A bacterium can also be engineered to have mucus binding properties, by adding both a secretion and anchor signal to TFF.

Cell-Adherence Polypeptide

In some embodiments of the present disclosure, the microorganism (e.g., bacterium) contains an exogenous nucleic acid encoding a fusion protein containing a cell-adherence polypeptide. Any polypeptide exhibiting cell-adherence properties, e.g., binding to intestinal cells or cell-lines thereof (e.g., Caco-2, IEC-18, or HT29-MTX cells) are useful in the context of the present disclosure. Cell-adherence capabilities may be measured using art-recognized methods, such as those disclosed herein. In some examples, the cell-adherence polypeptide is selected from cell and mucus-binding protein A (CmbA) (see, e.g., Jensen et al., *Microbiology* 2014, 160(4):671-681), mucus binding protein or mub domain proteins (Mub) (see, e.g., Boekhorst et al., *Microbiology* 2006, 152(1):273-280), mucus adhesion promoting protein (MapA) (see, e.g., Miyoshi et al., *Biosci. Biotechnol. Biochem.* 2006, 70(7):1622-8), lactococcal mucin binding protein (MpbL) (see, e.g., Lukić et al., *Appl. Environ. Microbiol.* 2012, 78(22):7993-8000). In some examples, the fusion protein may include a cell-wall anchor peptide, such as *Staphylococcus aureus* protein A anchor fragment (SpaX) (see, e.g., Steidler et al., *Appl. Environ. Microbiol.* 1998, 64(1):342-5). All of the above disclosures are incorporated herein by reference in their entirety. In some examples, the cell-adherence polypeptide is a CmbA polypeptide, such as CmbA from *Lactobacillus reuteri*. See, e.g., ATCC PTA6474, e.g., as disclosed in Jensen et al., supra.

In some examples according to any of the above embodiments, the cell-adherence polypeptide is a CmbA polypeptide having an amino acid sequence that is at least 90%, at least 92%, at least 95%, at least 96%, at least 97%, at least 98%, or at least 99% identical to SEQ ID NO: 1. In other examples according to any of the above embodiments, the cell-adherence polypeptide is a CmbA polypeptide encoded by an exogenous nucleic acid sequence that is at least 90%, at least 92%, at least 95%, at least 96%, at least 97%, at least 98%, or at least 99% identical to SEQ ID NO: 2.

Mucin-Binding Polypeptide

In some embodiments of the present disclosure the microorganism (e.g., bacterium) contains an exogenous nucleic acid encoding a fusion protein containing a mucin-binding polypeptide. Any polypeptide exhibiting mucin-binding properties, e.g., binding to mucin preparations in vitro, are useful in the context of the present disclosure. Mucin-binding capabilities may be measured using art-recognized methods, such as those disclosed herein. Exemplary mucin-binding polypeptides include trefoil factor (TFF) polypeptides (e.g., TFF1, TFF2, or TFF3) (see, e.g., Caluwaerts, S. et al., *Oral. Oncol.* 2010, 46:564-570) and MucBP polypeptides (see, e.g., Lukic et al, *Appl. Environ. Microbiol.* 2012, 78(22):7993-8000). In some examples, the current disclosure provides a microorganism (e.g., a bacterium) comprising an exogenous nucleic acid encoding a fusion protein, wherein the fusion protein contains a cell-adherence polypeptide (e.g., a CmbA polypeptide) and a mucin-binding polypeptide (e.g., a TFF polypeptide). In some examples, the TFF polypeptide is a human TFF polypeptide (e.g., hTFF1, hTFF2, or hTFF3). In other examples according to any of the above embodiments, the mucin-binding polypeptide is a human TFF3 polypeptide having an amino acid sequence that is at least 90%, at least 92%, at least 95%, at least 96%, at least 97%, at least 98%, or at least 99% identical to SEQ ID NO: 3. In other examples according to any of the above embodiments, the mucin-binding polypeptide is a human TFF3 polypeptide encoded by an exogenous nucleic acid sequence that is at least 90%, at least 92%, at least 95%, at least 96%, at least 97%, at least 98%, or at least 99% identical to SEQ ID NO: 4. In some examples, the mucin-binding polypeptide is a fish TFF polypeptide, or an amphibian TFF polypeptide. In yet other examples, the mucin-binding polypeptide includes (or consists of) a trefoil-like domain, such as those disclosed in Fujita et al., *Mol. Reprod. Dev.* 2006, 75(7):1217-1228.

Constructs

In some embodiments the microorganism (e.g., bacterium, such as *Lactococcus lactis*) comprises an expression vector capable of expressing the fusion protein and optionally a therapeutic polypeptide. For example, the fusion protein is exposed on the cell surface under conditions present at the mucosa, e.g., in the gastrointestinal tract. The microorganism (e.g., bacterium) can comprise expression vectors capable of expressing the fusion protein, such that the fusion protein is exposed on the cell surface to a degree sufficient to provide the desired GI retention. One of skill in the art may adjust the amount of microorganisms (e.g., bacterium) provided to the subject to deliver the desired amount of therapeutic polypeptide.

Usually, the expression system will comprise a genetic construct comprising at least one nucleotide sequence encoding at least one fusion protein, e.g., operably linked to a promoter capable of directing expression of the sequence(s) in the hosting microorganism. Suitably the fusion protein to be expressed can be encoded by a nucleic acid sequence that is adapted to the preferred codon usage of the host. The construct may further contain (all) other suitable element(s), including enhancers, transcription initiation sequences, signal sequences, reporter genes, transcription termination sequences, etc., operable in the selected host, as is known to the person skilled in the art.

In some examples, the construct is in a form suitable for transformation of the host and/or in a form that can be stably maintained in the host, such as a vector, plasmid or mini-chromosome. Suitable vectors comprising nucleic acid for introduction into microorganisms (e.g., bacteria) can be chosen or constructed, containing appropriate regulatory sequences, including promoter sequences, terminator fragments, enhancer sequences, marker genes and other sequences as appropriate. Vectors may be plasmids, viral (e.g., phage or phagemid), as appropriate. For further details see, for example, Molecular Cloning: a Laboratory Manual: 2nd edition, Sambrook et al., 1989, Cold Spring Harbor Laboratory Press, the relevant disclosure of which is incorporated herein by reference.

Many known techniques and protocols for the manipulation of nucleic acids, for example in preparation of nucleic acid constructs, mutagenesis, sequencing, introduction of DNA into cells and gene expression, and analysis of proteins, are described in detail in Short Protocols in Molecular Biology, Second Edition, Ausubel et al., eds., John Wiley & Sons, 1992, the relevant disclosure of which is incorporated herein by reference. In one embodiment, the coding sequence for the fusion protein is contained in an operon, i.e., a nucleic acid construct for poly-cistronic expression. In an operon, transcription from the promoter results in a mRNA which comprises more than one coding sequence, each with its own suitably positioned ribosome binding site upstream. Thus, more than one polypeptide can be translated from a single mRNA. Use of an operon enables expression of the fusion protein and a therapeutic polypeptide to be coordinated. Polycistronic expression systems in bacterial host cells are described, e.g., in U.S. Patent Application No. 2014/0105863 to Vanden-Broucke et al., which is incorporated herein by reference in its entirety.

In an embodiment the present invention relates to stably transfected microorganisms (e.g., bacteria). In some examples, the present disclosure provides microorganisms (e.g., bacteria), in which the exogenous nucleic acid encoding the fusion protein has been integrated into the host cell's chromosome. Techniques for establishing stably transfected microorganisms are known in the art. For instance, the nucleic acid encoding the fusion protein may be cloned into the host's chromosome via homologous recombination. In some examples, an essential gene of the host is disrupted by the homologous recombination event, such as deletion of the gene, one or more amino acid substitutions leading to an inactive form of the protein encoded by the essential gene, or to a frameshift mutation resulting in a truncated form of the protein encoded by the essential gene. In an embodiment, the essential gene is the thyA gene. An exemplary technique is described, e.g., in WO 02/090551, which is incorporated herein by reference in its entirety. The transforming plasmid can be any plasmid, as long as it cannot complement the disrupted essential gene, e.g., thyA gene. The plasmid may be self-replicating, may carry one or more genes of interest, and may carry one or more resistance markers. In some examples, the plasmid is an integrative plasmid (i.e., integration plasmid). Such integrative plasmid may be used to disrupt the essential gene, by causing integration at the locus of the essential gene, e.g., thyA site, because of which the function of the essential gene, e.g., the thyA gene, is disrupted. In some examples, the essential gene, such as the thyA gene, is replaced by double homologous recombination by a cassette comprising the gene or genes of interest, flanked by targeting sequences that target the insertion to the essential gene, such as the thyA target site. It will be appreciated that that these targeting sequences are sufficiently long and sufficiently homologous to enable integration of the gene of interest into the target site.

The genetic construct encoding the fusion protein may be present in the host cell extra-chromosomally, e.g., autonomously replicating using an own origin of replication, or may be integrated into the microbial genomic DNA, e.g., bacterial or yeast chromosome, e.g., *Lactococcus* chromosome. In the latter case, a single copy or multiple copies of the nucleic acid may be integrated; the integration may occur at a random site of the chromosome or, as described above, at a predetermined site thereof, such as in the thyA locus of *Lactococcus*, e.g., *Lactococcus lactis*.

Hence, in some embodiments, the genetic construct encoding the fusion protein may further comprises sequences configured to effect insertion of the genetic construct into the chromosome of a host cell. In some examples, insertion of the genetic construct into particular sites within a microbial genome, e.g., chromosome of a host cell may be facilitated by homologous recombination. For instance, a genetic construct of the present disclosure may comprise one or more regions of homology to the site of integration within the chromosome, of the host cell. The sequence at the chromosome site may be natural, i.e., as occurring in nature, or may be an exogenous sequence introduced by previous genetic engineering.

In some examples, the region(s) of homology may be at least 50 base pairs (bp), 100 bp, 200 bp, 300 bp, 400 bp, 500 bp, 600 bp 700 bp, 800 bp, 900 bp, 1000 bp, or more.

In one example, two regions of homology may be included, one flanking each side of the relevant expression units present in the genetic construct. Such configuration may advantageously insert the relevant sequences into host cells. Methods for homologous recombination, especially in bacterial hosts, and selecting for recombinants, are generally known in the art.

Transformation methods of microorganisms are known to the person skilled in the art, such as for instance protoplast transformation and electroporation.

High degrees of expression can be achieved by using homologous expression and/or secretion signals on the expression vectors present in the microorganism, e.g., *Lactococcus lactis*. Expression signals will be apparent to the person skilled in the art. The expression vector can be optimized for expression depending on the microorganism it is incorporated into. For instance, specific expression vectors that gave sufficient levels of expression in *Lactococcus, Lactobacillus lactis, casei* and *plantarum* are known. Moreover, systems are known which have been developed for the expression of heterologous antigens in the non-pathogenic, non-colonizing, non-invasive food-grade bacterium *Lactococcus lactis* (see UK patent GB2278358B, which is incorporated herein by reference). In some examples, construct of the present disclosure comprises the multi-copy expression vector described in PCT/NL95/00135 (WO-A-96/32487), in which the nucleotide sequence encoding the fusion protein has been incorporated. Such a construct is particularly suitable for expression of a desired polypeptide in a lactic acid bacterium, in particular in a *Lactobacillus*, at a high level of expression, and also can be used to direct the expressed product to the surface of the bacterial cell. The constructs (e.g., of PCT/NL95/00135) may be characterized in that the nucleic acid sequence encoding the fusion protein is preceded by a 5' non-translated nucleic acid sequence comprising at least the minimal sequence required for ribosome recognition and RNA stabilization. This can be followed by a translation initiation codon which may be (immediately) followed by a fragment of at least 5 codons of the 5' terminal part of the translated nucleic acid sequence of a gene of a lactic acid bacterium or a structural or functional equivalent of the fragment. The fragment may also be controlled by the promoter. The contents of PCT/NL95/00135, including the differing embodiments disclosed therein, and all other documents mentioned in this specification, are incorporated herein by reference. One aspect of the present invention provides a method which permits the high level regulated expression of heterologous genes in the host and the coupling of expression to secretion. In another embodiment, the T7 bacteriophage RNA polymerase and its cognate promoter are used to develop a powerful expression system according to WO 93/17117, which is incorporated herein by reference. In one embodiment, the expression plasmid is derived from pT1 NX.

In some embodiments, a promoter employed in accordance with the present disclosure is expressed constitutively in the bacterium. The use of a constitutive promoter avoids the need to supply an inducer or other regulatory signal for expression to take place. For example, the promoter directs expression at a level at which the bacterial host cell remains viable, i.e., retains some metabolic activity, even if growth is not maintained. Advantageously, such expression may be at a low level. For example, where the expression product accumulates intracellularly, the level of expression may lead to accumulation of the expression product at less than about 10% of cellular protein, or about or less than about 5%, for example about 1-3%. The promoter may be homologous to the bacterium employed, i.e., one found in that bacterium in nature. For example, a Lactococcal promoter may be used in a *Lactococcus*. An exemplary promoter for use in *Lactococcus lactis* (or other Lactococci) is "P1" derived from the chromosome of *Lactococcus lactis* (Waterfield, N R, Lepage, R W F, Wilson, P W, et al. (1995). "The isolation of lactococcal promoters and their use in investigating bacterial luciferase synthesis in *Lactococcus lactis*" Gene 165(1):9-15). Another example of a promoter is the usp45 promoter. Other useful promoters are described in U.S. Pat. No. 8,759,088 to Steidler et al., and in U.S. Patent Application No. 2014/0105863 to Vandenbroucke et al., the disclosures of which are incorporated herein by reference in their entirety.

The nucleic acid construct or constructs may comprise a secretory signal sequence. Thus, in some embodiments the nucleic acid encoding the fusion protein may provide for secretion of the polypeptides, e.g., by appropriately coupling a nucleic acid sequence encoding a signal sequence to the nucleic acid sequence encoding the polypeptide). Ability of a bacterium harboring the nucleic acid to secrete the antigen may be tested in vitro in culture conditions which maintain viability of the organism. Exemplary secretory signal sequences include any of those with activity in Gram-positive organisms such as *Bacillus, Clostridium* and *Lactobacillus*. Such sequences may include the α-amylase secretion leader of *Bacillus amyloliquefaciens* or the secretion leader of the Staphylokinase enzyme secreted by some strains of *Staphylococcus*, which is known to function in both Gram-positive and Gram-negative hosts (see "Gene Expression Using *Bacillus*," Rapoport (1990) Current Opinion in Biotechnology 1:21-27), or leader sequences from numerous other *Bacillus* enzymes or S-layer proteins (see pp 341-344 of Harwood and Cutting, "Molecular Biological Methods for *Bacillus*," John Wiley & Co. 1990). In one embodiment, said secretion signal is derived from usp45 (Van Asseldonk et al., *Mol. Gen. Genet.* 1993, 240:428-434). In some embodiments, the fusion protein is constitutively secreted.

Formulations and Regimens

In the methods of the present disclosure, multiple therapeutic polypeptides may be expressed by the same or different microorganisms. For example, (a) PAL and amino acid decarboxylase; (b) a T1D specific antigen such as PINS and a Treg activating cytokine such as IL-2 or IL-10 (c) a gluten antigen and IL-2 or IL-10, and the like. If expressed in separate organisms, one or preferably both bacteria will express mucin and/or cell-binding factors. When the two polypeptides are expressed by different microorganisms, those may be administered to the subject in the same (e.g., combined) formulation or may be administered in separate (e.g., different) formulations. Separate formulations may be administered at the same time or at different time points. For example, the use of first and second therapeutic polypeptide producing microorganisms in their respective formulations can be administered to the subject simultaneously or may be administered sequentially, e.g., with a rest period between administrations.

In some embodiments, the first and second therapeutic polypeptide producing microorganisms are administered simultaneously. In some examples, according to these embodiments, the first therapeutic polypeptide microorganism, and the second therapeutic polypeptide microorganism are comprised in the same pharmaceutical formulation, or in more than one pharmaceutical formulation taken at the same time. In some embodiments, the two bioactive polypeptides are delivered to the subject using a microorganism producing both the IL-2 and the T1D-specific antigen.

In some embodiments, the microorganism will be administered, once, twice, three, four, five, or six times daily, e.g., using an oral formulation. In some embodiments, the microorganisms are administered every day, every other day, once per week, twice per week, three times per week, or four times per week. In other embodiments, treatment occurs once every two weeks. In other embodiments, treatment occurs once every three weeks. In other embodiments, treatment occurs once per month.

The duration of a treatment cycle for the method is, for example, 7 days to the subject's lifetime, as needed to treat or reverse disease, or prevent relapse. In some embodiments, a treatment cycle lasts for about 30 days to about 2 years. In other embodiments, the subject will have a treatment cycle that lasts from 30 days to 1.5 years. In other embodiments, the subject will have a treatment cycle that lasts from 30 days to 1 year. In other embodiments, the subject will have a treatment cycle that lasts from 30 days to 11 months. In other embodiments, the subject will have a treatment cycle that lasts from 30 days to 10 months. In other embodiments, the subject will have a treatment cycle that lasts from 30 days to 9 months. In other embodiments, the subject will have a treatment cycle that lasts from 30 days to 8 months. In other embodiments, the subject will have a treatment cycle that lasts from 30 days to 7 months. In other embodiments, the subject will have a treatment cycle that lasts from 30 days to 6 months. In other embodiments, the subject will have a treatment cycle that lasts from 30 days to 5 months. In other embodiments, the subject will have a treatment cycle that lasts from 30 days to 4 months. In other embodiments, the subject will have a treatment cycle that lasts from 30 days to 3 months. In other embodiments, the subject will have a treatment cycle that lasts from 30 days to 2 months.

Daily maintenance doses can be given for a period clinically desirable in the subject, for example from 1 day up to several years (e.g. for the subject's entire remaining life); for example from about (2, 3 or 5 days, 1 or 2 weeks, or 1 month) upwards and/or for example up to about (5 years, 1 year, 6 months, 1 month, 1 week, or 3 or 5 days). Administration of the daily maintenance dose for about 3 to about 5 days or for about 1 week to about 1 year is typical. Unit doses can be administered from twice daily to once every two weeks until a therapeutic effect is observed.

The microorganisms producing the first and second therapeutic polypeptide may be delivered in mono- or combination therapy for the treatment of the disease. In some embodiments, the compositions of the present disclosure include additional therapeutically active agents. In some embodiments, the compositions of the present disclosure, and treatment of the subject, does not involve other active components, e.g., does not involve additional immune-modulating substances, such as antibodies (e.g., anti-CD3 for treatment of T1D). Thus, in some examples, the pharmaceutical compositions of the present disclosure consist essentially of the microorganism as described herein (expressing the therapeutic IL-2 and antigen polypeptides), and a pharmaceutically acceptable carrier.

Pharmaceutical Compositions and Carriers

Microorganisms (e.g., bacteria or yeast as described herein) may be administered in pure form, combined with other active ingredients, and/or combined with pharmaceutically acceptable (i.e., nontoxic) excipients or carriers. The term "pharmaceutically acceptable" is used herein in accordance with its art-recognized meaning and refers to carriers that are compatible with the other ingredients of a pharmaceutical composition, and are not deleterious to the recipient thereof.

The compositions of the present invention can be prepared in any known or otherwise effective dosage or product form suitable for use in providing systemic delivery of the microorganism (e.g., bacteria) to the mucosa, which would include pharmaceutical compositions and dosage forms as well as nutritional product forms.

In some embodiments, the formulation is an oral formulation or pharmaceutical composition. In some examples according to this embodiment, the formulation or pharmaceutical composition comprises the non-pathogenic microorganism in a dry-powder form (e.g., freeze-dried form) or in compacted form thereof, optionally in combination with other dry carriers. Oral formulations will generally include an inert diluent carrier or an edible carrier.

In some examples, the oral formulation comprises a coating or utilizes an encapsulation strategy, which facilitates the delivery of the formulation into the intestinal tract, and/or allows the microorganism be released and hydrated in the intestinal tract (e.g., the ileum, small intestine, or the colon). Once the microorganism is released from the formulation and sufficiently hydrated, it begins expressing the bioactive polypeptide, which is subsequently released into the surroundings, or expressed on the surface of the microorganism. Such coating and encapsulation strategies (i.e., delayed-release strategies) are known to those of skill in the art. See, e.g., U.S. Pat. No. 5,972,685; WO 2000/18377; and WO 2000/22909, the disclosures of which are incorporated herein by reference in their entirety.

In some embodiments, the disclosure provides a pharmaceutical composition comprising the microorganism (e.g., the non-pathogenic bacteria) in a lyophilized or freeze dried form, optionally in conjunction with other components, such as dextrans, sodium glutamate, and polyols. Exemplary freeze dried compositions are described, e.g., in U.S. Patent Application No. 2012/0039853 to Corveleyn et al., the disclosure of which is incorporated herein by reference in its entirety. Exemplary formulations comprise freeze-dried bacteria (e.g., a therapeutically effective amount of the bacteria) and a pharmaceutically acceptable carrier. Freeze-dried bacteria may be prepared in the form of capsules, tablets, granulates and powders, each of which may be administered orally. Alternatively, freeze-dried bacteria may be prepared as aqueous or oily suspensions in suitable media, or lyophilized bacteria may be suspended in a suitable medium, such as a drink, just prior to use.

For oral administration, the formulation may be a gastroresistant oral dosage form. For example, the oral dosage form (e.g., capsules, tablets, pellets, micro-pellets, granulates, and the like) may be coated with a thin layer of excipient (usually polymers, cellulosic derivatives and/or lipophilic materials) that resists dissolution or disruption in the stomach, but not in the intestine, thereby allowing transit through the stomach in favor of disintegration, dissolution and absorption in the intestine (e.g., the small intestine, or the colon). In some examples, oral formulations may include compounds providing controlled release, sustained release, or prolonged release of the microorganism, and thereby provide controlled release of the desired protein encoded therein. These dosage forms (e.g., tablets or capsules) typically contain conventional and well known excipients, such as lipophilic, polymeric, cellulosic, insoluble, swellable excipients. Controlled release formulations may also be used for any other delivery sites including intestinal, colon, bioadhesion or sublingual delivery (i.e., dental mucosal delivery) and bronchial delivery. When the compositions of the invention are to be administered rectally or vaginally, pharmaceutical formulations may include suppositories and creams. In this instance, the host cells are suspended in a mixture of common excipients also including lipids. Each of the aforementioned formulations are well known in the art and are described, for example, in the following references: Hansel et al. (1990, Pharmaceutical dosage forms and drug delivery systems, 5th edition, William and Wilkins); Chien 1992, (Novel drug delivery system, 2nd edition, M. Dekker); Prescott et al. (1989, Novel drug delivery, J. Wiley & Sons); Gazzaniga et al., (1994, Oral delayed release system for colonic specific delivery, *Int. J. Pharm.* 108:77-83).

In some embodiments, the oral formulation includes compounds that can enhance mucosal delivery and/or mucosal uptake of the bioactive polypeptides expressed by the microorganism. In other examples, the formulation includes compounds, which enhance the viability of the microorganism within the formulation, and/or once released.

The bacteria of the invention can be suspended in a pharmaceutical formulation for administration to the human or animal having the disease to be treated. Such pharmaceutical formulations include but are not limited to live Gram-positive bacteria and a medium suitable for administration. The bacteria may be lyophilized in the presence of common excipients such as lactose, other sugars, alkaline and/or alkali earth stearate, carbonate and/or sulphate (e.g., magnesium stearate, sodium carbonate and sodium sulphate), kaolin, silica, flavorants and aromas. Bacteria so-lyophilized may be prepared in the form of capsules, tablets, granulates and powders (e.g., a mouth rinse powder), each of which may be administered by the oral route. Alternatively, some Gram-positive bacteria may be prepared as aqueous suspensions in suitable media, or lyophilized bacteria may be suspended in a suitable medium just prior to use, such medium including the excipients referred to herein and other excipients such as glucose, glycine and sodium saccharinate.

In some examples, the microorganism is locally delivered to the gastrointestinal tract of the subject using any suitable method. For example, microsphere delivery systems could be employed to enhance delivery to the gut. Microsphere delivery systems include microparticles having a coating that provides localized release into the gastrointestinal tract of the subject (e.g., controlled release formulations such as enteric-coated formulations and colonic formulations).

For oral administration, gastroresistant oral dosage forms may be formulated, which dosage forms may also include compounds providing controlled release of the Gram-positive bacteria and thereby provide controlled release of the desired protein encoded therein (e.g., IL-2). For example, the oral dosage form (including capsules, tablets, pellets, granulates, powders) may be coated with a thin layer of excipient (e.g., polymers, cellulosic derivatives and/or lipophilic materials) that resists dissolution or disruption in the stomach, but not in the intestine, thereby allowing transit through the stomach in favor of disintegration, dissolution and absorption in the intestine.

The oral dosage form may be designed to allow slow release of the Gram-positive bacteria and of the produced exogenous proteins, for instance as controlled release, sustained release, prolonged release, sustained action tablets or capsules. These dosage forms usually contain conventional and well-known excipients, such as lipophilic, polymeric, cellulosic, insoluble, swellable excipients. Such formulations are well-known in the art and are described, for example, in the following references: Hansel et al., Pharmaceutical dosage forms and drug delivery systems, 5th edition, William and Wilkins, 1990; Chien 1992, Novel drug delivery system, 2nd edition, M. Dekker; Prescott et al., Novel drug delivery, J. Wiley & Sons, 1989; and Gazzaniga et al., *Int. J. Pharm.* 108:77-83 (1994).

The pharmaceutical dosage form (e.g. capsule) is coated with pH-dependent Eudragit polymers to obtain gastric juice resistance and for the intended delivery at the terminal ileum and colon, where the polymers dissolve at pH 6.5. By using other Eudragit polymers or a different ratio between the polymers, the delayed release profile could be adjusted, to release the bacteria for example in the duodenum or jejunum.

Pharmaceutical compositions contain at least one pharmaceutically acceptable carrier. Non-limiting examples of suitable excipients, diluents, and carriers include preservatives, inorganic salts, acids, bases, buffers, nutrients, vitamins, fillers and extenders such as starch, sugars, mannitol, and silicic derivatives; binding agents such as carboxymethyl cellulose and other cellulose derivatives, alginates, gelatin, and polyvinyl pyrolidone; moisturizing agents such as glycerol/disintegrating agents such as calcium carbonate and sodium bicarbonate; agents for retarding dissolution such as paraffin; resorption accelerators such as quaternary ammonium compounds; surface active agents such as acetyl alcohol, glycerol monostearate; adsorptive carriers such as kaolin and bentonite; carriers such as propylene glycol and ethyl alcohol, and lubricants such as talc, calcium and magnesium stearate, and solid polyethyl glycols.

Pharmaceutically compatible binding agents, and/or adjuvant materials can be included as part of the composition. Tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or enteric agents. Further, a syrup may contain, in addition to the active compounds, sucrose as a sweetening agent and certain preservatives, dyes, colorings, and flavorings. It will be appreciated that the form and character of the pharmaceutically acceptable carrier is dictated by the amount of active ingredient with which it is to be combined, the route of administration and other well-known variables. The carrier(s) must be "acceptable" in the sense of being compatible with the other ingredients of the formulation and not deleterious to the recipient thereof.

Alternative preparations for administration include sterile aqueous or nonaqueous solutions, suspensions, and emulsions. Examples of non-aqueous solvents are dimethylsulfoxide, alcohols, propylene glycol, polyethylene glycol, vegetable oils such as olive oil and injectable organic esters such as ethyl oleate. Aqueous carriers include mixtures of alcohols and water, buffered media, and saline. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like. Various liquid formulations are possible for these delivery methods, including saline, alcohol, DMSO, and water based solutions.

Oral aqueous formulations include excipients, such as pharmaceutical grades of mannitol, lactose, starch, magnesium stearate, sodium saccharine, cellulose, magnesium carbonate and/or the like. These compositions take the form of solutions such as mouthwashes and mouth rinses, further comprising an aqueous carrier such as for example water, alcoholic/aqueous solutions, saline solutions, parenteral vehicles such as sodium chloride, Ringer's dextrose, and the like.

Aqueous mouthwash formulations are well-known to those skilled in the art. Formulations pertaining to mouthwashes and oral rinses are discussed in detail, for example, in U.S. Pat. Nos. 6,387,352, 6,348,187, 6,171,611, 6,165, 494, 6,117,417, 5,993,785, 5,695,746, 5,470,561, 4,919,918, U.S. Patent Appl. No. 2004/0076590, U.S. Patent Appl. No. 2003/0152530, and U.S. Patent Appl. No. 2002/0044910, each of which is herein specifically incorporated by reference into this section of the specification and all other sections of the specification.

Other additives may be present in the formulations of the present disclosure, such as flavoring, sweetening or coloring agents, or preservatives. Mint, such as from peppermint or spearmint, cinnamon, eucalyptus, citrus, cassia, anise and menthol are examples of suitable flavoring agents. Flavoring agents can be present in the oral compositions in an amount in the range of from 0 to 3%, e.g., up to 2%, such as up to 0.5%, e.g., around 0.2%, in the case of liquid compositions.

Sweeteners include artificial or natural sweetening agents, such as sodium saccharin, sucrose, glucose, saccharin, dextrose, levulose, lactose, mannitol, sorbitol, fructose, maltose, xylitol, thaumatin, aspartame, D-tryptophan, dihydrochalcones, acesulfame, and any combinations thereof, which may be present in an amount in the range of from about 0 to 2%, e.g., up to 1% w/w, such as 0.05 to 0.3% w/w of the oral composition.

Coloring agents are suitable natural or synthetic colors, such as titanium dioxide or CI 42090, or mixtures thereof. Coloring agents can be present in the compositions in an amount in the range of from 0 to 3%; e.g., up to 0.1%, such as up to 0.05%, e.g., about 0.005-0.0005%, in the case of liquid compositions. In some examples, sodium benzoate is added as a preservative, e.g., in concentrations insufficient substantially to alter the pH of the composition, otherwise the amount of buffering agent may need to be adjusted to arrive at the desired pH.

Other optional ingredients include humectants, surfactants (non-ionic, cationic or amphoteric), thickeners, gums and binding agents. A humectant adds body to the formulation and retains moisture in a dentifrice composition. In addition, a humectant helps to prevent microbial deterioration during storage of the formulation. It also assists in maintaining phase stability and provides a way to formulate a transparent or translucent dentifrice.

Suitable humectants include glycerin, xylitol, glycerol and glycols such as propylene glycol, which may be present in an amount of up to 50% w/w each, but total humectant is e.g., not more than about 60-80% w/w of the composition. For example, liquid compositions may comprise up to about 30% glycerin plus up to about 5%, or about 2% w/w xylitol. In some examples, surfactants are not anionic and may include polysorbate 20 or cocoamidobetaine or the like in an amount up to about 6%, or about 1.5 to 3%, w/w of the composition.

In some examples, when the oral compositions of the invention is in a liquid form, it a film-forming agent that may be added up to about 3% w/w of the oral composition, such as in the range of from 0 to 0.1%, or about 0.001 to 0.01%, such as about 0.005% w/w of the oral composition. Suitable film-formers include (in addition to sodium hyaluronate) those sold under the tradename Gantrez.

Liquid nutritional formulations for oral or enteral administration may comprise one or more nutrients such as fats, carbohydrates, proteins, vitamins, and minerals. Many different sources and types of carbohydrates, lipids, proteins, minerals and vitamins are known and can be used in the nutritional liquid embodiments of the present invention, provided that such nutrients are compatible with the added ingredients in the selected formulation, are safe and effective for their intended use, and do not otherwise unduly impair product performance.

These nutritional liquids can be formulated with sufficient viscosity, flow, or other physical or chemical characteristics to provide a more effective and soothing coating of the mucosa while drinking or administering the nutritional liquid. These nutritional embodiments may also represent a balanced nutritional source suitable for meeting the sole, primary, or supplemental nutrition needs of the individual.

Non-limiting examples of suitable nutritional liquids are described in U.S. Pat. No. 5,700,782 (Hwang et al.); U.S. Pat. No. 5,869,118 (Morris et al.); and U.S. Pat. No. 5,223,285 (DeMichele et al.), which descriptions are incorporated herein by reference.

Nutritional proteins suitable for use herein can be hydrolyzed, partially hydrolyzed or non-hydrolyzed, and can be derived from any known or otherwise suitable source such as milk (e.g., casein, whey), animal (e.g., meat, fish), cereal (e.g., rice, corn), vegetable (e.g., soy), or combinations thereof.

Fats or lipids suitable for use in the nutritional liquids include, but are not limited to, coconut oil, soy oil, corn oil, olive oil, safflower oil, high oleic safflower oil, MCT oil (medium chain triglycerides), sunflower oil, high oleic sunflower oil, structured triglycerides, palm and palm kernel oils, palm olein, canola oil, marine oils, cottonseed oils, and combinations thereof. Carbohydrates suitable for use in the nutritional liquids may be simple or complex, lactose-containing or lactose-free, or combinations thereof. Non-limiting examples of suitable carbohydrates include hydrolyzed corn starch, maltodextrin, glucose polymers, sucrose, corn syrup, corn syrup solids, rice-derived carbohydrate, glucose, fructose, lactose, high fructose corn syrup and indigestible oligosaccharides such as fructo-oligosaccharides (FOS), and combinations thereof.

The nutritional liquids may further comprise any of a variety of vitamins, non-limiting examples of which include vitamin A, vitamin D, vitamin E, vitamin K, thiamine, riboflavin, pyridoxine, vitamin B12, niacin, folic acid, pantothenic acid, biotin, vitamin C, choline, inositol, salts and derivatives thereof, and combinations thereof.

The nutritional liquids may further comprise any of a variety of minerals known or otherwise suitable for us in patients at risk of or suffering from T1D, non-limiting examples of which include calcium, phosphorus, magnesium iron, selenium, manganese, copper, iodine, sodium, potassium, chloride, and combinations thereof.

The microorganisms and in particular the yeast and bacteria of the present invention can also be formulated as elixirs or solutions for convenient oral or rectal administration or as solutions appropriate for parenteral administration, for instance by intramuscular, subcutaneous or intravenous routes. Additionally, the nucleoside derivatives are also well suited for formulation as a sustained or prolonged release dosage forms, including dosage forms that release active ingredient only or in a particular part of the intestinal tract, e.g., over an extended or prolonged period of time to further enhance effectiveness. The coatings, envelopes, and protective matrices in such dosage forms may be made, for example, from polymeric substances or waxes well known in the pharmaceutical arts.

The compositions of the present invention include pharmaceutical dosage forms such as lozenges, troches or pastilles. These are typically discoid-shaped solids containing the active ingredient in a suitably flavored base. The base may be a hard sugar candy, glycerinated gelatin, or the combination of sugar with sufficient mucilage to give it form. Troches are placed in the mouth where they slowly dissolve, liberating the active ingredient for direct contact with the mucosa.

The troche embodiments of the present invention can be prepared, for example, by adding water slowly to a mixture of the powdered active, powdered sugar, and a gum until a pliable mass is formed. A 7% acacia powder can be used to provide sufficient adhesiveness to the mass. The mass is rolled out and the troche pieces cut from the flattened mass, or the mass can be rolled into a cylinder and divided. Each cut or divided piece is shaped and allowed to dry, to thus form the troche dosage form.

If the active ingredient is heat labile, it may be made into a lozenge preparation by compression. For example, the granulation step in the preparation is performed in a manner similar to that used for any compressed tablet. The lozenge is made using heavy compression equipment to give a tablet that is harder than usual as it is desirable for the dosage form to dissolve or disintegrate slowly in the mouth. In some examples, ingredients are selected to promote slow-dissolving characteristics.

In a particular formulation of the present invention, the microorganisms will be incorporated in a bioadhesive carrier containing pregelatinized starch and cross-linked poly (acrylic acid) to form a bioadhesive tablet and a bioadhesive gel suitable for buccal application (i.e., having prolonged bioadhesion and sustained drug delivery). For example, a powder mixture of non-pathogenic and non-invasive bacterium according to the invention), bioadhesive polymers (pregelatinized starch and cross-linked poly (acrylic acid) coprocessed via spray drying), sodium stearyl fumarate (lubricant) and silicon dioxide (glidant) is processed into tablets (weight: 100 mg; diameter: 7 mm). The methods for the production of these tablets are well known to the person skilled in the art and has been described before for the successful development of bioadhesive tablets containing various drugs (miconazol, testosterone, fluoride, ciprofloxacin) (Bruschi M. L. and de Freitas O., *Drug Development and Industrial Pharmacy,* 2005 31:293-310). All excipient materials are commercially available in pharmaceutical grades.

To optimize the formulation, the drug load in the tablets and the ratio between starch and poly (acrylic acid) will be varied. Based on previous research, the maximum drug load in the coprocessed bioadhesive carrier is about 60% (w/w) and the starch/poly (acrylic acid) ratio can be varied between 75/25 and 95/5 (w/w). During the optimization study the bioadhesive properties of the tablets and the drug release from the tablets are the main evaluation parameters, with the standard tablet properties (hardness, friability) as secondary evaluation criteria.

The bacteria are incorporated into an aqueous dispersion of pregelatinized starch and cross-linked poly (acrylic acid). This polymer dispersion is prepared via a standard procedure using a high shear mixer.

Similar to the tablet, the drug load of the gel and the starch/poly (acrylic acid) ratio need to be optimized in order to obtain a gel having optimal adherence to the esophageal mucosa. For a gel, the concentration of the polymers in the dispersion is an additional variable as it determines the viscosity of the gel, hence its muco-adhesive properties.

A model to screen the bioadhesive properties of polymer dispersions to the mucosa of esophagus has been described in detail by Batchelor et al. (*Int. J. Pharm.,* 238:123-132, 2002).

Other routes and forms of administration include food preparations containing the live microorganisms. In some examples, the bioactive polypeptide-expressing microorganism can be included into a dairy product.

The pharmaceutical compositions of the present invention can be prepared by any known or otherwise effective method for formulating or manufacturing the selected dosage form. For example, the microorganisms can be formulated along with common, e.g., pharmaceutically acceptable carriers, such as excipients and diluents, formed into oral tablets, capsules, sprays, lozenges, treated substrates (e.g., oral or topical swabs, pads, or disposable, non-digestible substrate treated with the compositions of the present invention); oral liquids (e.g., suspensions, solutions, emulsions), powders, suppositories, or any other suitable dosage form. In some embodiments, the present disclosure provides a method for the manufacture of a pharmaceutical composition. Exemplary methods include: contacting the microorganism (e.g., the non-pathogenic bacterium) with a pharmaceutically acceptable carrier, thereby forming the pharmaceutical composition. In some examples, the method further includes: growing the microorganism in a medium. The method may further include drying (e.g., freeze-drying) a liquid containing the microorganism, wherein the liquid optionally includes the pharmaceutically acceptable carrier.

Unit Dosage Forms

The current disclosure further provides unit dosage forms comprising a certain amount of a microorganism (e.g., bacterium) of the present disclosure optionally in combination with a food-grade or pharmaceutically acceptable carrier. Exemplary unit dosage forms contain from about $1\times10^3$ to about $1\times10^{14}$ colony-forming units (cfu) of a non-pathogenic microorganism (e.g., a non-pathogenic Gram-positive bacterium). Other exemplary unit dosage forms contain from about $1\times10^4$ to about $1\times10^{13}$ colony-forming units (cfu) of a non-pathogenic microorganism (e.g., a non-pathogenic Gram-positive bacterium), or from about $1\times10^4$ to about $1\times10^{12}$ colony-forming units (cfu) of a non-pathogenic microorganism (e.g., a non-pathogenic Gram-positive bacterium). In other embodiments, the unit dosage form comprises from about $1\times10^5$ to about $1\times10^{12}$ colony-forming units (cfu), or from about $1\times10^6$ to about $1\times10^{12}$ colony-forming units (cfu) of the non-pathogenic microorganism (e.g., the non-pathogenic Gram-positive bacterium). In other embodiments, the unit dosage form comprises from about $1\times10^8$ to about $1\times10^{12}$ colony-forming units (cfu), or from about $1\times10^9$ to about $1\times10^{12}$ colony-forming units (cfu) of the non-pathogenic microorganism (e.g., the non-pathogenic Gram-positive bacterium). In yet other embodiments, the unit dosage form comprises from about $1\times10^9$ to about $1\times10^{11}$ colony-forming units (cfu), or from about $1\times10^9$ to about $1\times10^{10}$ colony-forming units (cfu) of the non-pathogenic microorganism (e.g., the non-pathogenic Gram-positive bacterium). In yet other embodiments, the unit dosage form comprises from about $1\times10^7$ to about $1\times10^{11}$ colony-forming units (cfu), or from about $1\times10^8$ to about $1\times10^{10}$ colony-forming units (cfu) of the non-pathogenic microorganism (e.g., the non-pathogenic Gram-positive bacterium).

In yet other embodiments, the unit dosage form comprises from about $1\times10^9$ to about $1\times10^{10}$ colony-forming units (cfu), or from about $1\times10^9$ to about $100\times10^9$ colony-forming units (cfu) of the non-pathogenic microorganism (e.g., the non-pathogenic Gram-positive bacterium).

The unit dosage form can have any physical form or shape. In some embodiments, the unit dosage form is adapted for oral administration. In some examples according to these embodiments, the unit dosage form is in the form of a capsule, a tablet, or a granule. Exemplary capsules include capsules filled with micro-granules. In some embodiments, the non-pathogenic microorganism (e.g., the non-pathogenic Gram-positive bacterium) contained in the dosage form is in a dry-powder form. For example, the microorganism is in a freeze-dried powder form, which is optionally compacted and coated.

This invention will be better understood by reference to the Examples that follow, but those skilled in the art will readily appreciate that these are only illustrative of the invention as described more fully in the claims that follow thereafter. Additionally, throughout this application, various publications are cited. The disclosures of these publications are hereby incorporated by reference into this application in their entirety to describe more fully the state of the art to which this invention pertains.

EXAMPLES

Example 1

Generation of *Lactococcus lactis* Strains Expressing CmbA on the Bacterial Surface (a) Episomal Expression of CmbA The codon usage of the CmbA encoding gene (see, SEQ ID NO: 2 and coding region for CmbA in SEQ ID NO: 11, FIGS. 5A-D) was optimized to *L. lactis* MG1363. The resulting DNA sequence was made synthetically. Using overlay PCR assembly, PthyA>>SSusp45 (usp45 secretion signal) and cmbA were fused to form one PCR fragment. The PthyA>>SSusp45-cmbA expression unit was positioned between the 5'thyA and 3'thyA regions of *L. lactis* strain MG1363 by PCR. The resulting PCR fragment: 5'thyA>>PthyA>>SSusp45-cmbA>>3'thyA was subcloned into plasmid pORI19 (see, e.g., Law et al., *J. Bacteriol.* 1995, 177(24):7011-7018) to generate plasmid pAGX1893. Plasmid pAGX1893 was transformed into *Lactococcus lactis* strain LL108 resulting in strain LL108[pAGX1893].

(b) Chromosomal Integration (Constitutive Expression of CmbA)

Integration vector pAGX1893 was electroporated into two different *L. lactis* strains containing a bicistronic expression cassette containing a heterologous nucleic acid sequence encoding the therapeutic polypeptide PAL (gapB>>rpmD>>pal) (SEQ ID NOs: 24 and 25). These two strains were sAGX0599 and sAGX0585 (a trehalose accumulating strain). Insertion of SSusp45-cmbA by homologous recombination (double-crossover) in the thyA locus was confirmed by PCR and Sanger DNA sequencing. The resulting strains were termed sAGX0618 and sAGX0619, respectively.

Example 2

Generation of *Lactococcus lactis* Strains Expressing MbpL on the Bacterial Surface (a) Episomal Expression of MbpL (Using Native Signal Peptide)

Construction of a [PthyA>>mbpL] thyA integration/expression vector pAGX1903: The codon usage of the MbpL encoding gene (with signal peptide; SSmbpL) was optimized to *L. lactis* MG1363. The resulting DNA sequence was made synthetically. Using overlay PCR assembly, PthyA and mbpL were fused to form one PCR fragment. The PthyA>>SSmbpL>>mbpL expression unit (SEQ ID NO: 17) was positioned between the 5'thyA and 3'thyA regions of *L. lactis* strain MG1363 by PCR. The resulting PCR fragment: 5'thyA>>PthyA>>SSmbpL>>mbpL>>3'thyA was subcloned into plasmid pORI19 to generate plasmid pAGX1903, which was transformed into *L. lactis* strain LL108 resulting in strain LL108[pAGX1903].

(b) Episomal Expression of MbpL (Using SSusp45)

Another construct, which incorporates mbpL may include secretion leader sequence SSusp45 instead of MbpL's own signal peptide. A [PthyA>>SSusp45-mbpL] thyA integration/expression vector can be prepared in accordance with the procedure outlined in Example 1, wherein the nucleic acid sequence encoding cmbA can be replaced with a nucleic acid sequence encoding MbpL polypeptide without its own signal peptide. The MbpL encoding gene (without signal peptide) can be optimized to *L. lactis* MG1363. The resulting DNA sequence can be made synthetically. Using overlay PCR assembly, PthyA>>SSusp45 and mbpL can be fused to form one PCR fragment. The PthyA>>SSusp45-mbpL expression unit (SEQ ID NO: 15) can be positioned between the 5'thyA and 3'thyA regions of *L. lactis* strain MG1363 by PCR. The resulting PCR fragment: 5'thyA>>PthyA>>SSusp45-mbpL>>3'thyA can be subcloned, e.g., into plasmid pORI19 to generate another plasmid, which can be transformed into a L. lactis, e.g., strain LL108.

Example 3

Generation of Lactococcus lactis Strains Expressing MapA on the Bacterial Surface
(a) Episomal Expression of MapA (Using Native Signal Peptide)
Construction of a [PthyA>>mapA] thyA integration/expression vector pAGX1946: The mapA encoding gene (with signal peptide) was optimized to L. lactis MG1363. The resulting DNA sequence was made synthetically. Using overlay PCR assembly, PthyA and mapA were fused to form one PCR fragment. The PthyA>>SSmapA>>mapA expression unit (SEQ ID NO: 21) was positioned between the 5'thyA and 3'thyA regions of L. lactis strain MG1363 by PCR. The resulting PCR fragment: 5'thyA>>PthyA>>SSmapA>>mapA>>3'thyA was subcloned in plasmid pORI19 to generate plasmid pAGX1946, which was transformed into L. lactis strain LL108 resulting in strain LL108[pAGX1946].
(b) Episomal Expression of MapA (Using SSusp45)
Another construct, which incorporates mapA may include a secretion leader sequence SSusp45 instead of MapA's own signal peptide. A [PthyA>>SSusp45>>mapA] thyA integration/expression vector can be prepared, e.g., in accordance with the procedure in Example 1, wherein the nucleic acid sequence encoding cmbA can be replaced with a nucleic acid sequence encoding MapA polypeptide without its signal peptide. The mapA encoding gene can be optimized to L. lactis MG1363. The resulting DNA sequence can be made synthetically. Using overlay PCR assembly, PthyA>>SSusp45 and mapA (without signal peptide) can be fused to form one PCR fragment. The PthyA>>SSusp45-mapA expression unit (SEQ ID NO: 19) can be positioned between the 5'thyA and 3'thyA regions of L. lactis strain MG1363 by PCR. The resulting PCR fragment: 5'thyA>>PthyA>>SSusp45-mapA>>3'thyA can be subcloned, e.g., into plasmid pORI19 to generate another plasmid, which can be transformed into a L. lactis strain, e.g., LL108.

Example 4

Figure 1:
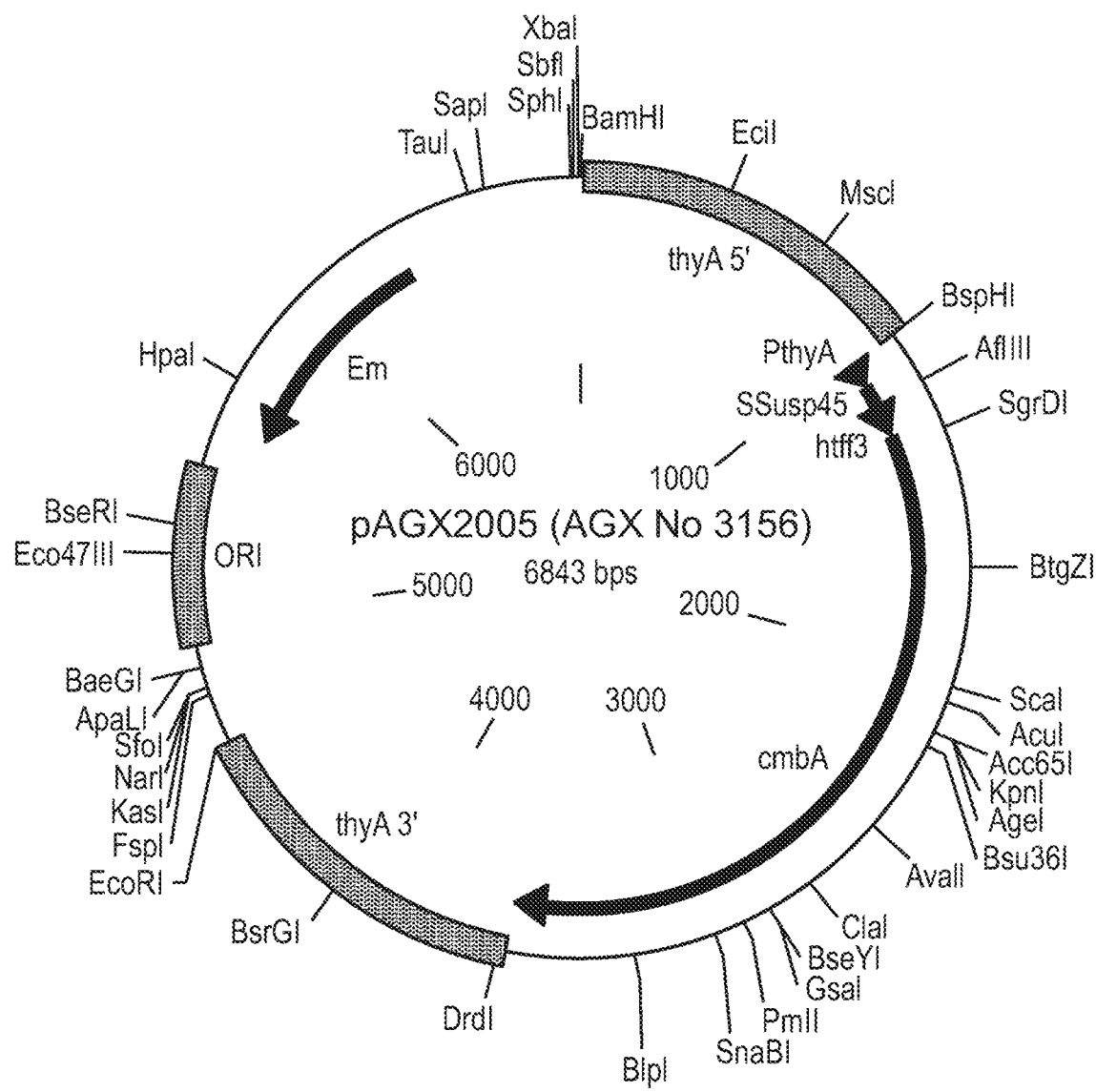
FIG. 1 is a plasmid map of PthyA>>SSusp45-htff3-CmbA expression/thyA integration vector pAGX2005. Abbreviations: thyA5', 5' flanking region of the thymidine synthase A (thyA) gene of MG1363; PthyA, thyA promoter of MG1363; SSups45, gene that encodes for the secretion signal of MG1363 protein usp45; hTFF3, gene that encodes for human trefoil factor 3 with optimized codon usage for *L. lactis*; CmbA, gene that encodes for *Lactobacillus reuteri* ATCC PTA6474 cell and mucus-binding protein A; thyA3', 3' flanking region of the thyA gene of MG1363; ORI, origin of replication of plasmid pORI19; Em, erythromycin resistance marker.

Lactococcus lactis Strains Expressing an hTFF3-CmbA Fusion Protein on the Bacterial Surface
(a) Expression of hTFF3
FIG. 4 illustrates an exemplary SSusp45-htff3 construct (amino acid and nucleic acid sequences) which can be used as the N-terminal portion of a fusion protein, with a C-terminal adherence polypeptide. The C-terminal adherence polypeptide can be added through PCR fusion or more traditional ligation.
(b) Episomal Expression of hTFF3-CmbA
A [PthyA>>SSusp45-hTFF3-cmbA] thyA integration/expression vector was constructed. The codon usage of the hTFF3 and CmbA (without signal peptide) encoding genes were optimized to L. lactis MG1363. The resulting htff3 and cmbA DNA sequences were made synthetically. Using overlay PCR assembly, PthyA>>SSusp45, hTFF3 and cmbA were fused to form one PCR fragment. The PthyA>>SSusp45-hTFF3-cmbA expression unit (see SEQ ID NO: 11 and FIGS. 5A-D) was positioned between the 5'thyA and 3'thyA regions of L. lactis strain MG1363 by PCR. The resulting PCR fragment: 5'thyA>>PthyA>>SSusp45-hTFF3-cmbA>>3'thyA was subcloned in plasmid pORI19 (Law et al., 1995 supra) to generate plasmid pAGX2005 (see FIG. 1), which was transformed into L. lactis strain LL108 resulting in strain LL108 [pAGX2005].

(b) Chromosomal Integration (Constitutive Expression of hTFF3-cmbA; thyA Promoter)
Integration vector pAGX2005 (see above and FIG. 1) was electroporated into two different thyA-wild type Lactococcus lactis strains, L. lactis sAGX0599 and sAGX0585 (trehalose accumulating strain) containing a bicistronic expression cassette encoding the therapeutic polypeptide PAL (gapB>>rpmD>>pal). Insertion of SSusp45-hTFF3-CmbA (see, e.g., SEQ ID NO: 11 and FIGS. 5A-D) by homologous recombination (double crossover) in the thyA locus was confirmed by PCR and Sanger DNA sequencing. The resulting strains were termed sAGX0644 and sAGX0645.
(c) Chromosomal Integration (Constitutive Expression of hTFF3-CmbA; PhllA Promoter)
Promoter replacement vector pAGX2041 (PthyA->PhllA) was electroporated into L. lactis strain sAGX0644 (see above) containing a bicistronic expression cassette encoding the therapeutic polypeptide PAL (gapB>>rpmD>>pal) and PthyA>>SSusp45-hTFF3-cmbA. Replacement of PthyA by PhllA by homologous recombination (double crossover) was confirmed by PCR and Sanger DNA sequencing. The resulting strain was termed: sAGX0660.

Example 5

Lactococcus lactis Strains Expressing hTFF1-SpaX on the Bacterial Surface
(a) Episomal Expression of hTFF1-spaX
Construction of a [PthyA>>SSusp45-hTFF1-spaX] (SEQ ID NOs: 22 and 23) thyA integration/expression vector pAGX1894: The codon usage of the hTFF1 encoding gene was optimized to L. lactis MG1363. The resulting DNA sequence was made synthetic. Using overlay PCR assembly, PthyA>>SSusp45, hTFF1 and the gene encoding for the cell wall anchor of protein A of Staphylococcus aureus (SpaX, Steidler et al., 1998) were fused to form one PCR fragment. The PthyA>>SSusp45-hTFF1-spaX expression unit was positioned between the 5'thyA and 3'thyA regions of L. lactis strain MG1363 by PCR. The resulting PCR fragment: 5'thyA>>PthyA>>SSusp45-hTFF1-spaX>>3'thyA was subcloned into plasmid pORI19 to generate plasmid pAGX1894, which was transformed into L. lactis strain LL108 resulting in strain LL108[pAGX1894].

Example 6

Lactococcus lactis Strains Episomally Expressing Mucin-Binding and Cell-Binding Polypeptides
The following plasmids and Lactococcus lactis strains were prepared as described herein and were tested for their mucin- and cell-binding (Caco-2, IEC-18, and HT29-MTX cells) capabilities. The plasmids listed in Table 1 below were electroporated into L. lactis strain LL108.

TABLE 1

Lactococcus lactis Strains Episomally Expressing Mucin-Binding and Cell-Binding Polypeptides

| Plasmid | Strain | BioAdhesion Construct | Mucin binding | Cell binding |
|---|---|---|---|---|
| pAGX1417 | LL108[pAGX1417] | none (control) | − | − |
| pAGX1893 | LL108[pAGX1893] | PthyA >> cmbA | − | +++ |
| pAGX1903 | LL108[pAGX1903] | PthyA >> mbpL | − | +++ |
| pAGX1946 | LL108[pAGX1946] | PthyA >> mapA | − | + |
| pAGX1894 | LL108[pAGX1894] | PthyA >> SSusp45-hTFF1-spaX | +++ | − |
| pAGX1986 | LL108[pAGX1986] | PthyA >> SSusp45-hTFF3-spaX | N/A | N/A |
| pAGX2005 | LL108[pAGX2005] | PthyA >> SSusp45-hTFF3-cmbA | +++ | +++ |

(+);, (++);, (+++): cell recovery between 0 and 12% (indicates relative overall performance based on various experiments, using various kinds of cells (Caco-2, IEC-18, HT29-MTX) and substrates (mucins type II & III).

(a) Binding of *Lactococcus Lactis* LL108[pAGX2005] to Mucins

Experimental procedure: mucins (Sigma type II, cat #M2378-100G, mucins form porcine stomach and Sigma type III, cat #M1778-10G, mucin from porcine stomach, bound sialic acid (0.5-1.5%), partially purified) were coated at 500 µg/ml in 50 mM carbonate buffer on Nunc MaxiSorp® plates. Plates were washed 3 times with PBS, blocked with PBS+Tween20 and washed 3 times with PBS. Overnight saturated *L. lactis* cultures were diluted in PBS to $OD_{600}=1$. Cultures were washed with PBS+0.05% Tween20 and resuspended in 1 volume PBS+0.05% Tween20. 100 µl bacterial suspension was applied on each well. Plates were incubated for 16 hours at 4° C. Plates were washed 3 times with PBS+0.05% Tween20. Plates were dried for 1 hour at 55° C. (A) OD was measured at 405 nm. (B) 100 µl per well crystal violet (1 mg/ml) was added and incubated for 45 minutes at room temperature. OD was subsequently measured at 595 nm.

Figure 2A:
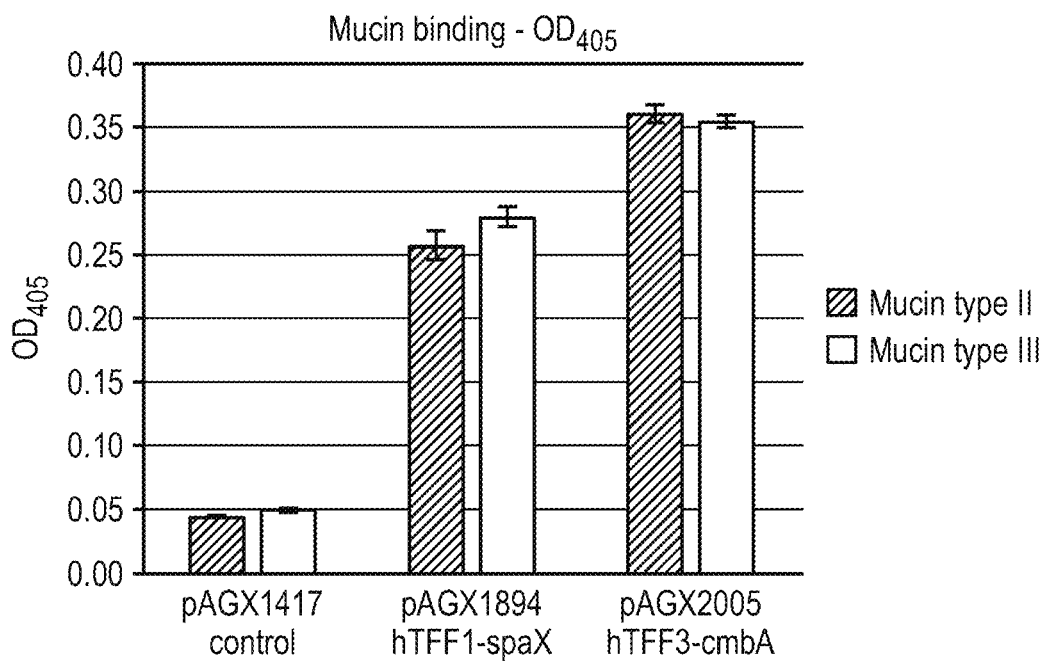
FIGS. 2A-B are graphs demonstrating enhanced binding of bacterial (*Lactococcus lactis*) cells to mucins and wherein mucin binding is measured using $OD_{405}$ (FIG. 2A) or crystal violet staining (FIG. 2B). pAGX1417: *L. lactis* strain LL108 that harbors an empty plasmid; pAGX1894: *L. lactis* strain LL108 that harbors a plasmid for the expression of hTFF1-SpaX on the bacterial surface; pAGX2005: *L. lactis* strain LL108 that harbors a plasmid for the expression of hTFF3-
Figure 2B:
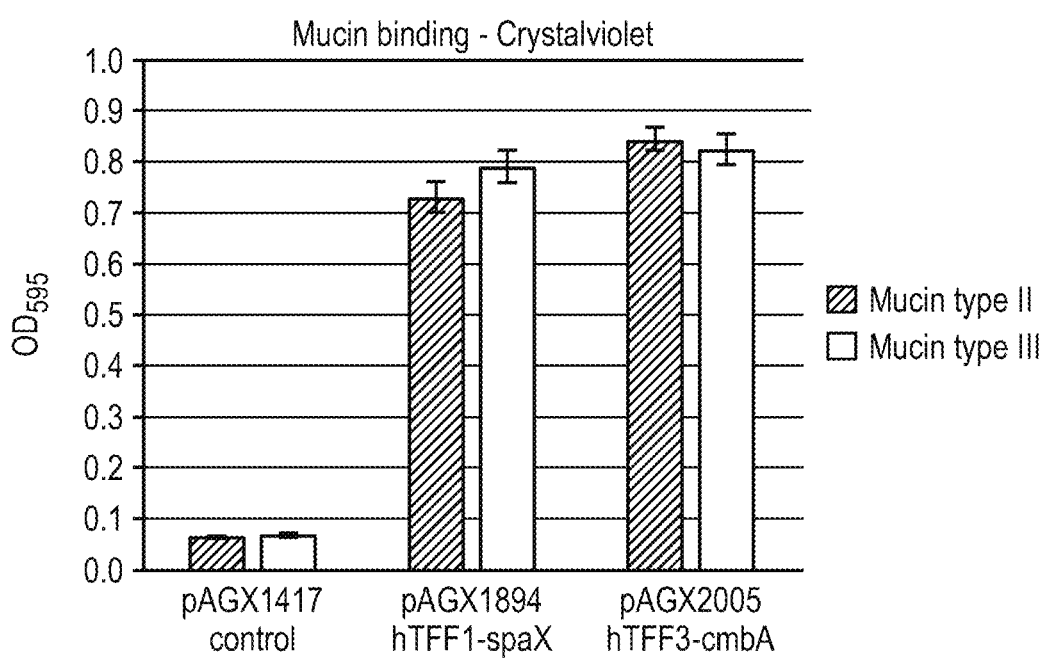

Result:

FIG. 2 shows that strain LL108[pAGX1894], expressing human trefoil factor 1 (hTFF1) on its surface by use of the *Staphylococcus aureus* protein A anchor fragment SpaX (Steidler et al., 1998, supra) and strain LL108[pAGX2005], expressing hTFF3-CmbA on its surface bind to mucins with comparable strength (Sigma type II & type III) when measured using two different readout methods. In contrast, a control strain containing an empty control vector, LL108 [pAGX1417] did not show any binding to mucins for the two readout methods.

(b) Adherence of *Lactococcus Lactis* LL108[pAGX2005] to Caco-2 Cells

Experimental procedure: Caco-2 cells were seeded in a 12-well plate at $5\times10^4$ cells/cm$^2$. Cells were grown for 17 days to differentiate. Overnight saturated *L. lactis* cultures were diluted 1/1000 in DMEM and washed 3 times with DMEM. *L. lactis* cells were finally resuspended in DMEM. 1 ml of the bacterial suspensions was applied on the cells in the 12-well plate and incubated for 1 hour at 37° C. Cells were washed 3 times with DMEM. Cells were harvested by lysis with Triton-X100 (1 ml 0.1% Triton-X100 in PBS was applied on the cells, incubation for 5 to 10 minutes until total detachment of the cells). Harvested cell suspensions were appropriately diluted and plated out on GM17E plates. Bacterial counts on the plates were measured after 24 hours of incubation at 30° C. Percent recovery was determined as *L. lactis* cells that were recovered from the plating of the harvested cell suspensions divided with the number of cells that were applied initially to the Caco-2 cells.

FIG. 3 shows that strain LL108[pAGX1893] expressing CmbA on its surface and strain LL108[pAGX2005] expressing hTFF3-CmbA on its surface exhibit comparable adhesion to Caco-2 cells. In contrast, control strain LL108 [pAGX1417] (control) and strain LL108[pAGX1894] expressing hTFF1-SpaX on its surface did not exhibit enhanced adherence to Caco-2 cells.

Conclusion:

*L. lactis* strains expressing an hTFF3-CmbA fusion polypeptide on their surface exhibit enhanced in vitro binding to mucins and enhanced adherence to Caco-2 cells when compared to corresponding strains not expressing an hTFF3-CmbA fusion polypeptide.

Example 7

Construction of Integration Plasmids Containing Bicistronic Expression Units

The integration plasmids listed in Table 2 below were prepared as described herein using a construct incorporating an intergenic region (e.g., the intergenic region preceding rplN) and can be tested for their mucin- and cell-binding capabilities as described herein. The plasmids listed in Table 2 can be electroporated into a host cell, such as *L. lactis* strain LL108 to generate bacteria expressing (e.g., constitutively expressing) polypeptides encoded by these constructs.

TABLE 2

Integration Plasmids Containing Bicistronic Expression Units

| Plasmid | BioAdhesion Construct (in indicated operon) |
|---|---|
| pAGX1935 | PhllA >> hllA >> rplN >> cmbA |
| pAGX1938 | Pusp45 >> usp45 >> rplN >> cmbA |
| pAGX1997 | PhllA >> hllA >> rplN >> SSusp45-hTFF1-spaX |
| pAGX1998 | PhllA >> hllA >> rplN >> SSusp45-hTFF3-spaX |
| pAGX2016 | PhllA >> hllA >> rplN >> SSusp45-hTFF3-cmbA |

Example 8

*Lactococcus lactis* Strains Containing Chromosomally Integrated Expression Units The following plasmids and *Lactococcus lactis* strains were prepared as described herein and were tested for their mucin- and cell-binding capabilities as described in Example 6. Results are illustrated in FIGS. 6 and 7A-B. The plasmids listed in Table 3 below were integrated into a *L. lactis* host strain containing a chromosomally integrated PAL expression unit (PgapB>>gapB>>rpmD>>pal). Some of the host strains further included genetic modifications leading to intracellular trehalose accumulation (*). Exemplary trehalose accumulating strains (i) lack functional trehalose-6-phosphate phosphorylase (ΔtrePP) and lack functional cellobiose-specific PTS system IIc component (ΔptcC) genes; (ii) express an *E. coli* trehalose-6-phosphate phosphatase (*E. coli* otsB), and (iii) express trehalose transporter genes (PTS genes). See, e.g., U.S. Pat. No. 9,200,249 and U.S. Patent Application Publication 2014/0234371, the disclosures of which are incorporated herein in their entireties.

Selected strains were also tested for PAL expression. Results (summarized in FIG. 8) indicate that expression of the cell adherence and mucoadhesive polypeptides did not have a significant influence on the amount of PAL expressed per cell ($\mu g/10^9$ cells).

TABLE 3

*Lactococcus lactis* Strains Constitutively Expressing Mucin-Binding and Cell-Binding Polypeptides

| Strain | Trehalose | BioAdhesion Construct (thyA locus) | Mucin binding | Cell binding |
|---|---|---|---|---|
| sAGX0585 | (*) | none (control) | − | − |
| sAGX0599 | wt | none (control) | − | − |
| sAGX0618 | wt | PthyA >> cmbA | − | ++ |
| sAGX0619 | (*) | PthyA >> cmbA | − | ++ |
| sAGX0644 | wt | PthyA >> SSusp45-hTFF3-cmbA | ++ | ++ |
| sAGX0645 | (*) | PthyA >> SSusp45-hTFF3-cmbA | ++ | ++ |
| sAGX0660 | wt | PhllA >> SSusp45-hTFF3-cmbA | +++ | ++ |

(*) PhllA >> PTS; Δ trePP; Δ ptcC; usp45 >> otsB.
wt: wild-type (no trehalose accumulation)
(+); (++); (+++): cell recovery between 0 and 12% (indicates relative overall performance based on various experiments, using various kinds of cells (Caco-2, IEC-18, HT29-MTX) and substrates (mucins type II & III).

Example 9

Construction of *Lactococcus lactis* Strains Containing Chromosomally Integrated Expression Units The *Lactococcus lactis* strains listed in Table 4 below can be prepared as described herein using appropriate constructs and can be tested for their mucin- and cell-binding capabilities as described herein Each of these bacterial strains expressing mucin-binding and cell-adherence polypeptides on their surface (e.g., *Lactococcus lactis* strains expressing hTFF3-CmbA fusion proteins on their surface) can be evaluated for their gastrointestinal (GI)-transit time, and can be compared with corresponding strains not expressing the mucin-binding and cell-adherence polypeptides (e.g., corresponding strains not expressing a hTFF3-CmbA fusion polypeptide).

For example, an equal number of bacterial cells (e.g., based on cfu) of the bacterial strains, which either express hTFF3-CmbA, or do not express the fusion protein, can be administered to an individual (human or animal). Non-episomal strains+/−hTFF3-CmbA can be equipped with an antibiotic selection marker (e.g., pT1NX, conveying erythromycin resistance). Episomal strains can be further selected based on their Em resistance. GI transit times may be measured by one of the following methods:

TABLE 4

*Lactococcus lactis* Strains Constitutively Expressing Mucin-Binding and Cell-Binding Polypeptides

| Strain | Trehalose | BioAdhesion Construct (thyA locus) |
|---|---|---|
| sAGX0620 | wt | PthyA >> SSmbpL >> mbpL |
| sAGX0621 | (a) | PthyA >> SSmbpL >> mbpL |
| sAGX0624 | wt | PthyA >> SSmapA >> mapA |

TABLE 4-continued

*Lactococcus lactis* Strains Constitutively Expressing Mucin-Binding and Cell-Binding Polypeptides

| Strain | Trehalose | BioAdhesion Construct (thyA locus) |
|---|---|---|
| sAGX0625 | (a) | PthyA >> SSmapA >> mapA |
| sAGX0661 | (a) | PhllA >> SSusp45-hTFF3-cmbA |

(*) PhllA >> PTS; Δ trePP; ΔptcC; usp45 >> otsB.
wt: wild-type (no trehalose accumulation)

(1) At regular, (e.g., 1 h) intervals, total feces can be collected and the number of cfu recovered of can be determined for each strain, e.g., by Q-PCR or dilutive plating on solid agar containing erythromycin. This will yield for every strain a kinetic of recovery, which can show a time point of collection where the number of cfu recovered is maximal. It is observed that at time points beyond this maximum, more cfus are recovered for hTFF3-CmbA+ strains.

(2) At regular (e.g., 1 h) intervals, test animals (e.g., mice) can be sacrificed, and the number of bacterial cfu recovered from those animals can be determined by dilutive plating on solid agar containing erythromycin. This shows that at progressing time, more cfus are recovered for hTFF3-CmbA+ strains.

Example 10

Treatment of PKU—Gastrointestinal Degradation of Phenylalanine Using PAL Expressed by Genetically Modified Bacteria of the Current Disclosure The enzyme phenylalanine ammonia lyase (PAL), which converts Phe into the cinnamic acid and does not require a co-factor, has been used to treat phenylketonuria (PKU). See, e.g., Sarkissian, C. N. et al., *Proc. Natl. Acad. Sci. USA* 2008, 105: 20894-20899. Because PAL is rapidly degraded in the gastrointestinal (GI) tract, oral delivery is difficult to accomplish. A proof-of-concept study showed that oral administration of PAL expressed by genetically engineered *E. coli* in PKU (enu2/2) mice resulted in a significant reduction in plasma Phe levels. See, e.g., Sarkissian, C. N. et al., *Proc. Natl. Acad. Sci. USA* 1999, 96:2339-2344. However, safety concerns associated with the administration of *E. coli* prevents the use of this strategy in humans. A *Lactococcus lactis* strain expressing PAL has been generated and evaluated in a PKU mouse model. Oral administration of the recombinant bacteria resulted in a reduction of deuterated Phe absorption. See, e.g., International Patent Application Publication WO 2014066945.

To allow for the administration of genetically modified bacteria expressing PAL to human PKU patients, the inventors have prepared "clinical grade" strains, which constitutively express the PAL enzyme, and are further modified to exhibit increased GI transit times, greater stability under GI conditions, and self-containment. Chromosomal integration of the bioactive polypeptide is important because episomal expression is associated with safety concerns. For example, episomes can be readily transmitted to other bacteria in the gastro-intestinal system. Further, episomal maintenance can provide hurdles for manufacturing. Additionally, known PAL producing strains are rapidly destroyed in the proximal GI tract. Further, there is a concern that the known PAL producing bacteria could survive and propagate outside of the body.

Multiple *L. lactis* strains with one or more of the following improved features were generated, e.g., as described herein above in Example 8: 1) a PAL expression cassette that is integrated into the bacterial chromosome and driven by a constitutive promoter for improved safety and ease of manufacture; 2) modifications that promote trehalose accumulation, which improves *L. lactis* survival in the GI tract (see, e.g., Termont, S. et al., *Appl. Environ. Microbiol.* 2006, 72: 7694-7700); 3) incorporation of an auxotrophic dependency on thymidine to prevent survival outside the human body (see, e.g., Steidler, L. et al., *Nat. Biotechnol.* 2003, 21: 785-789); and 4) genetic modifications to express mucoadhesive surface proteins to improve retention in the proximal GI tract and prolong Phe degradation (see, e.g., Caluwaerts, S. et al., *Oral. Oncol.* 2010, 46:564-570). The strains were evaluated for PAL expression and their respective cell adherence and mucoadhesive properties as described in Examples 6 and 8. Surface expression of the adhesion protein improved bacterial retention on Caco-2 monolayers by approximately 8-fold. Adhesion to both Type II and Type III mucins was similarly enhanced. Importantly, the trehalose modification for improved survival in the GI tract and the expression of the adhesion molecule did not alter PAL levels expressed by the bacteria.

Selected bacterial strains, e.g., *Lactococcus lactis* strains (e.g., strains constitutively expressing PAL; e.g., sAGX0599, sAGX0644, aAGX0585, and sAGX0645) can be tested for their efficacy in the enu2/2 "PKU" mouse model to identify strains suitable for human clinical trials.

In the first study, sAGX0599, and sAGX0645 were tested in the PKU mice that received a dose of deuterated Phe concurrently with 109 cfu of *L. lactis* via gavage. Blood was sampled at 15 minute intervals for one hour and assayed for deuterated Phe. Positive control animals received a known episomal recombinant strain, e.g., as described in International Patent Application Publication WO 2014066945). Negative control animals received no bacteria. As shown in FIG. 9, the total Phe absorbed by mice was lowest in mice fed sAGX0599 (secreting PAL) and sAGX0645 (PAL and TFF3-CmbA), and was superior to the positive control. Interestingly, the final level of Phe was lowest in the mice fed sAGX0645 (PAL and TFF3-CmbA), but the Cmax of Phe was higher. This may reflect that sAGX0645 is moving slower down the small bowel towards the particular site of Phe uptake compared to *L. lactis* without the adhesion fusion protein. A lower Cmax and AUC may be obtained by administration of the Phe-degrading bacteria can prior to feeding. A lower Cmax and AUC may also be obtained by regular administration of the bacteria with a meal such that distal Phe-degrading bacteria to reduce Phe from one meal are already present from a previous meal.

It should be noted that feeding Phe is an artificial model of PKU. Single amino acids are very efficiently absorbed. In typical situations, proteins are broken down as they pass through the intestine such that free amino acids available for absorption occur primarily in more distal portions than the upper small intestine. Thus, a PAL-secreting bacterium located in the more distal portion of the intestine may be able to better block Phe uptake from food than as suggested by experiments administering Phe directly.

Moreover, *L. lactis* may be modified with different cell and mucus adhesion molecules to localize the delivery of PAL to the optimal section(s) of the intestine.

A second study may assess the pharmacodynamics of the selected bacterial strains, e.g., *Lactococcus lactis* strains. Bacteria can be administered up to six hours before the deuterated Phe. Blood can be assayed as described above. The resulting data can inform the scheduling for subsequent studies and provide information relevant to clinical application. For example, humans may take one unit dosage form (e.g., capsule) containing the bacteria with each meal.

A third study may assess the long-term effectiveness of the bacteria in lowering Phe blood levels. Animals can be gavaged with a selected bacterial strain (e.g., *Lactococcus lactis* strain), e.g., optimal strain from the first study, and can then be fed a standard chow diet. For example, two *L. lactis*-associated feedings each day with the duration for each feeding determined by the outcome from the second. Blood Phe levels can be assessed regularly, e.g., semi-weekly for three weeks. Controls can be those employed in the first study, and can also include a low Phe diet cohort. Note: this study may not use deuterated Phe. A positive outcome can be a statistically significant improvement in Phe blood levels, e.g., sufficient to likely result in clinical efficacy. Other studies can combine bacterial therapy (e.g., *L. lactis* therapy) with dietary intervention.

Each study can utilize cohorts of 5 mice to provide sufficient power for statistical analyses, and mice can be reused after a washout. Phe can be assayed by tandem mass spectrometry, which is both sensitive and specific and requires minimal amounts of blood.

Example 11

Treatment of Oral Mucositis

Oral mucositis is a breakdown of the oral mucosa and is a common complication of cancer therapy, especially for treatment of head and neck cancer. TFF1 is secreted in the upper GI tract and is associated with protection and healing of mucosal surfaces. TFF1 shows promise as a treatment for oral mucositis. To increase delivery of TFF1 at the oral mucosa, *L. lactis* is engineered to express both an hTFF1-CmbA fusion along with "free" hTFF1, both on the chromosome. If this was done step wise, there would be risk that one htff1 gene would recombine with another htff1 gene on the chromosome. To minimize this risk, hTFF1-cmbA and htff1 can be constructed polycistronically, and are therefore able to transform and integrate into the chromosome at one step. Further, the third base in each codon can changed in one tff1 sequence so that its nucleotide sequence differs from the other tff1 sequence, but the translated hTFF1 is the same. For example, there are six alanine codons with the following frequency: UCU (18.6), UCC (4.0), UCA (20.6), UCG (3.9), AGU (16.7), and AGC (7.3). Therefore, UCC and UCG may be interchangeable. UCU, UCA, and to a lesser extent AGU, may be interchangeable.

After modifying the codon frequency, the PhllA>>SSusp45>>hTFF1>>rpmD>>SSusp45>>hTFF1-CmbA is constructed through PCR, and is cloned between the 5' thyA and 3' thyA on a conditionally replicative carrier plasmid derived from pORI19. Transformation into *L. lactis* and selection, as described elsewhere herein, lead to integration into chromosomal thyA locus.

The resulting strain is shown to secrete TFF1 and express a TFF-CmbA fusion that mediates increased binding to oral mucus compared with a strain expressing TFF1 alone. The strain is tested in models of mucositis, and the presence of the TFF-CmbA increases persistence in the oral cavity and increases delivery of therapeutic TFF1, such that the frequency of dosing may be decreased.

Example 12

Treatment of Diabetes

The *Lactococcus lactis* strain secreting hTFF3-CmbA, as described above, is modified to express human proinsulin PINS and human IL10. For example, a construct for hPINS expression may be hPINS with a SSusp45 secretion leader, under the control of the strong gapB promoter and after the gapB gene and rpmD spacer (i.e., PgapB>>gapB>>rpmD>>usp45>>PINS). For hIL-10, a construct may be PhllA>>SSusp45>>hi-10.

Because hTFF3-CmbA are already inserted into the thyA locus, PINS and IL-10 may be inserted into another genomic site, such as ptcC or trePP. PtcC and trePP mutations are associated with trehalose accumulation. The resulting strain is tested for expression of hIL-10, PINS and hTFF3-CmbA. The strain is then tested in NOD mice, an animal model of type 1 diabetes, against a strain lacking hTFF3-CmbA. The strain lacking hTFF3-CmbA has previously been shown to generate a Treg response to PINS, reverse the autoimmune response to beta cells of the pancreas, and thereby treat diabetes. The treatment is especially efficacious in recent onset disease. The presence of the hTFF-CmbA may increase gut colonization and persistence, resulting in a stronger Treg response.

While some embodiments have been shown and described herein, such embodiments are provided by way of example only. Numerous variations, changes, and substitutions will now occur to those skilled in the art without departing from the invention. It should be understood that various alternatives to the embodiments of the invention described herein will be employed in practicing the invention.

EXEMPLARY EMBODIMENTS

1. A bacterium comprising an exogenous nucleic acid encoding a fusion protein, wherein said fusion protein comprises a cell-adherence polypeptide.
2. The bacterium of embodiment 1, wherein said cell-adherence polypeptide is selected from the group consisting of cell and mucus-binding protein A (CmbA), mucus binding protein (Mub), mucus adhesion promoting protein (MapA), lactococcal mucin binding protein (MbpL), and any combination thereof.
3. The bacterium of embodiment 2, wherein said cell-adherence polypeptide is CmbA.
4. The bacterium of embodiment 3, wherein said CmbA is *Lactobacillus reuteri* CmbA.
5. The bacterium of any one of the preceding embodiments, wherein said fusion protein further comprises a mucin-binding polypeptide.
6. The bacterium of embodiment 5, wherein said mucin-binding polypeptide is a trefoil factor (TFF) polypeptide.
7. The bacterium according to embodiment 6, wherein said fusion protein comprises CmbA and a TFF.
8. The bacterium of any one of embodiments 1 to 7, wherein said exogenous nucleic acid encoding a fusion protein is integrated into the chromosome of said bacterium.
9. The bacterium of any one of embodiments 1 to 7, wherein said exogenous nucleic acid encoding a fusion protein is located on a plasmid.
10. The bacterium of any one of the preceding embodiments, wherein said fusion protein is expressed by said bacterium.
11. The bacterium of embodiment 10, wherein said fusion protein is anchored in a cell wall of said bacterium.
12. The bacterium of any one of the preceding embodiments, wherein said exogenous nucleic acid encoding a fusion protein further comprises a secretion leader sequence encoding a secretion signal peptide.
13. The bacterium of embodiment 12, wherein said secretion leader sequence is SSusp45.
14. The bacterium of embodiment 13, wherein said secretion leader sequence encodes a secretion signal peptide having an amino acid sequence that is at least 90% identical to SEQ ID NO: 5.
15. The bacterium of any one of embodiments 12 to 14, wherein said secretion signal peptide is bound to said mucin-binding polypeptide.
16. The bacterium of any one of embodiments 12 to 15, wherein said secretion signal peptide is bound to a linker.
17. The bacterium of any one of embodiments 12 to 16, wherein said secretion signal peptide is cleaved from said fusion protein.
18. The bacterium of embodiment 17, wherein said secretion signal peptide is cleaved from said fusion protein when said fusion protein is anchored in a cell wall of said bacterium.
19. The bacterium of any one of embodiments 1 to 18, wherein said exogenous nucleic acid encoding a fusion protein is transcriptionally regulated by a promoter selected from the group consisting of a thyA promoter (PthyA), an hila promoter (PhllA), and a gapB promoter.
20. The bacterium of embodiment 19, wherein said exogenous nucleic acid encoding a fusion protein is transcriptionally regulated by PthyA.
21. The bacterium of embodiment 19, wherein said exogenous nucleic acid encoding a fusion protein is transcriptionally regulated by PhllA.
22. A bacterium comprising a fusion protein anchored in a cell-wall of said bacterium, wherein said fusion protein comprises a TFF polypeptide and a CmbA polypeptide.
23. The bacterium of any one of embodiments 1 to 22, wherein said bacterium is a Gram-positive bacterium.
24. The bacterium of embodiment 23, wherein said Gram-positive bacterium is non-pathogenic.

25. The bacterium of any one of embodiments 1 to 24, wherein said bacterium is a lactic acid bacterium (LAB).
26. The bacterium of embodiment 25, wherein said LAB is selected from the group consisting of a *Lactococcus* species (sp.) bacterium, a *Lactobacillus* sp. bacterium, a *Bifidobacterium* sp. bacterium, a *Streptococcus* sp. bacterium, and an *Enterococcus* sp. bacterium.
27. The bacterium of embodiment 25, wherein said LAB is selected from the group consisting of *Lactococcus garvieae, Lactococcus lactis, Lactococcus piscium, Lactococcus plantarum, Lactococcus raffinolactis, Lactobacillus acetotolerans, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarius, Lactobacillus aviarius* subsp. *araffinosus, Lactobacillus aviarius* subsp. *aviarius, Lactobacillus bavaricus, Lactobacillus bifermentans, Lactobacillus brevis, Lactobacillus buchneri, Lactobacillus bulgaricus, Lactobacillus carnis, Lactobacillus casei, Lactobacillus casei* subsp. *alactosus, Lactobacillus casei* subsp. *casei, Lactobacillus casei* subsp. *pseudoplantarum, Lactobacillus casei* subsp. *rhamnosus, Lactobacillus casei* subsp. *tolerans, Lactobacillus catenaformis, Lactobacillus cellobiosus, Lactobacillus collinoides, Lactobacillus confusus, Lactobacillus coryniformis, Lactobacillus coryniformis* subsp. *coryniformis, Lactobacillus coryniformis* subsp. *torquens, Lactobacillus crispatus, Lactobacillus curvatus, Lactobacillus curvatus* subsp. *curvatus, Lactobacillus curvatus* subsp. *melibiosus, Lactobacillus delbrueckii, Lactobacillus delbrueckii* subsp. *bulgaricus, Lactobacillus delbrueckii* subsp. *delbrueckii, Lactobacillus delbrueckii* subsp. *lactis, Lactobacillus divergens, Lactobacillus farciminis, Lactobacillus fermentum, Lactobacillus fornicalis, Lactobacillus fructivorans, Lactobacillus fructosus, Lactobacillus gallinarum, Lactobacillus gasseri, Lactobacillus graminis, Lactobacillus halotolerans, Lactobacillus hamsteri, Lactobacillus helveticus, Lactobacillus heterohiochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefiranofaciens, Lactobacillus kefirgranum, Lactobacillus kunkeei, Lactobacillus lactis, Lactobacillus leichmannii, Lactobacillus lindneri, Lactobacillus malefermentans, Lactobacillus mali, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus paracasei* subsp. *paracasei, Lactobacillus paracasei* subsp. *tolerans, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus reuteri, Lactobacillus rhamnosus, Lactobacillus rimae, Lactobacillus rogosae, Lactobacillus ruminis, Lactobacillus sakei, Lactobacillus sakei* subsp. *carnosus, Lactobacillus sakei* subsp. *sakei, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis, Lactobacillus yamanashiensis* subsp. *mali, Lactobacillus yamanashiensis* subsp. *yamanashiensis, Lactobacillus zeae, Bifidobacterium adolescentis, Bifidobacterium angulatum, Bifidobacterium bifidum, Bifidobacterium breve, Bifidobacterium catenulatum, Bifidobacterium longum, Bifidobacterium infantis, Enterococcus alcedinis, Enterococcus aquimarinus, Enterococcus asini, Enterococcus avium, Enterococcus caccae, Enterococcus camelliae, Enterococcus canintestini, Enterococcus canis, Enterococcus casseliflavus, Enterococcus cecorum, Enterococcus columbae, Enterococcus devriesei, Enterococcus diestrammenae, Enterococcus dispar, Enterococcus durans, Enterococcus eurekensis, Enterococcus faecalis, Enterococcus faecium, Enterococcus gallinarum, Enterococcus gilvus, Enterococcus haemoperoxidus, Enterococcus hermanniensis, Enterococcus hirae, Enterococcus italicus, Enterococcus lactis, Enterococcus lemanii, Enterococcus malodoratus, Enterococcus moraviensis, Enterococcus mundtii, Enterococcus olivae, Enterococcus pallens, Enterococcus phoeniculicola, Enterococcus plantarum, Enterococcus pseudoavium, Enterococcus quebecensis, Enterococcus raffinosus, Enterococcus ratti, Enterococcus rivorum, Enterococcus rotai, Enterococcus saccharolyticus, Enterococcus silesiacus, Enterococcus solitarius, Enterococcus sulfureus, Enterococcus termitis, Enterococcus thailandicus, Enterococcus ureasiticus, Enterococcus ureilyticus, Enterococcus viikkiensis, Enterococcus villorum, Enterococcus xiangfangensis, Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus milleri, Streptococcus mitis, Streptococcus mutans, Streptococcus oralis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus viridans,* and *Streptococcus zooepidemicus.*
28. The bacterium of embodiment 27, wherein said bacterium is *Lactococcus lactis.*
29. The bacterium of embodiment 28, wherein said *Lactococcus lactis* is selected from the group consisting of *Lactococcus lactis* subsp. *cremoris, Lactococcus lactis* subsp. *hordniae,* and *Lactococcus lactis* subsp. *lactis.*
30. The bacterium of any one of embodiments 6 to 29, wherein said TFF polypeptide is selected from the group consisting of TFF1, TFF2, and TFF3.
31. The bacterium of any one of embodiments 6 to 29, wherein said TFF polypeptide is selected from the group consisting of human TFF, mouse TFF, pig TFF, dog TFF, cat TFF, cow TFF, sheep TFF, fish TFF, and amphibial TFF.
32. The bacterium of embodiment 31, wherein said TFF polypeptide is human TFF.
33. The bacterium of embodiment 32, wherein said human TFF is human TFF3.

34. The bacterium of any one of embodiment 6 to 29, wherein said TFF polypeptide has an amino acid sequence at least 80% identical to SEQ ID NO: 3.
35. The bacterium of any one of embodiments 6 to 29, wherein said TFF polypeptide is a TFF variant polypeptide.
36. The bacterium of embodiment 35, wherein said TFF variant polypeptide has enhanced mucin-binding capability compared to a corresponding wild-type TFF polypeptide.
37. The bacterium of any one of embodiments 1 to 36, wherein said CmbA polypeptide has an amino acid sequence at least 80% identical to SEQ ID NO: 1.
38. The bacterium of any one of embodiments 1 to 37, further comprising an exogenous nucleic acid encoding at least one therapeutic polypeptide.
39. The bacterium of embodiment 38, wherein said at least one therapeutic polypeptide is a cytokine.
40. The bacterium of embodiment 38 or 39, wherein said at least one therapeutic polypeptide is an interleukin (IL).
41. The bacterium of embodiment 40, wherein said interleukin is selected from the group consisting of IL-2, IL-10, IL-18, and any combinations thereof.
42. The bacterium of embodiment 38, wherein said at least one therapeutic polypeptide is an antigen.
43. The bacterium of embodiment 42, wherein said at least one therapeutic polypeptide is an antigen and an interleukin.
44. The bacterium of embodiment 43, wherein said interleukin is IL-2 or IL-10.
45. The bacterium of any one of embodiments 42 to 44, wherein said antigen is an autoantigen.
46. The bacterium of embodiment 45, wherein said autoantigen is a type-1 diabetes (T1D)-specific antigen.
47. The bacterium of embodiment 46, wherein said T1D-specific antigen is selected from the group consisting of proinsulin (PINS), glutamic acid decarboxylase (GAD65), insulinoma-associated protein 2 (IA-2), islet-specific glucose-6-phosphatase catalytic subunit-related protein (IGRP), zinc transporter 8 (ZnT8), chromogranin A, (prepro) islet amyloid polypeptide (ppI-APP), peripherin, citrullinated glucose-regulated protein (GRP), and any combinations thereof.
48. The bacterium of embodiment 38, wherein said at least one therapeutic polypeptide is an antibody or a fragment thereof.
49. The bacterium of embodiment 48, wherein said antibody is a single-domain antibody or a nanobody.
50. The bacterium of embodiment 48 or 49, wherein said antibody is selected from the group consisting of an anti TNFα antibody, an antibody to IL-4, an antibody to IL-5, an antibody to IL-13, an antibody to IL-15, an antibody to immunoglobulin E (IgE), and any combinations thereof.
51. The bacterium of embodiment 48 or 49, wherein said antibody is a fusion protein comprising a soluble TNF receptor and an Fc region of an antibody.
52. The bacterium of embodiment 38, wherein said at least one therapeutic polypeptide is an enzyme or fragment thereof.
53. The bacterium of embodiment 52, wherein said enzyme or fragment thereof is functional.
54. The bacterium of embodiment 52 or 53, wherein said enzyme or fragment thereof is selected from the group consisting of a phenylalanine ammonia lyase (PAL), an amino acid decarboxylase, and any combinations thereof.
55. The bacterium of embodiment 54, wherein said enzyme or fragment thereof is PAL.
56. The bacterium of embodiment 38, wherein said at least one therapeutic polypeptide is selected from the group consisting of glucagon-like peptide 1 (GLP-1), glucagon-like peptide 2 (GLP-2), glucagon, exendin-4, and any combinations thereof.
57. The bacterium of embodiment 38, wherein said at least one therapeutic polypeptide is a growth factor.
58. The bacterium of embodiment 57, wherein said growth factor is epidermal growth factor (EGF).
59. The bacterium of embodiment 58, wherein said EGF is human EGF or porcine EGF.
60. The bacterium of embodiment 38, wherein said at least one therapeutic polypeptide is a TFF.
61. The bacterium of embodiment 60, wherein said TFF is selected from the group consisting of TFF1, TFF2, TFF3, and any combinations thereof.
62. The bacterium of any one of embodiments 38 to 61, wherein said therapeutic polypeptide is a human polypeptide.
63. The bacterium of any one of embodiments 42 to 44, wherein said antigen is an allergen.
64. The bacterium of embodiment 63, wherein said allergen is selected from the group consisting of a tree pollen allergen, a weed pollen allergen, a grass pollen allergen, a food allergen, a dust-mite allergen, a mold allergen, an animal dander allergen, and any combinations thereof.
65. The bacterium of embodiment 64, wherein said allergen is a weed pollen allergen.
66. The bacterium of embodiment 65, wherein said weed pollen allergen is a ragweed pollen allergen.
67. The bacterium of embodiment 64, wherein said allergen is a tree pollen allergen.
68. The bacterium of embodiment 67, wherein said tree pollen allergen is a birch pollen allergen or a Japanese cedar pollen allergen.
69. The bacterium of embodiment 64, wherein said allergen is a food allergen.
70. The bacterium of embodiment 69, wherein said food allergen is selected from the group consisting of a peanut allergen, a milk allergen, an egg allergen, a gluten allergen (gliadin epitope), and any combinations thereof.
71. The bacterium of any one of embodiments 38 to 70, wherein said exogenous nucleic acid encoding at least one therapeutic polypeptide is transcriptionally regulated by a gapB promoter.
72. The bacterium of any one of embodiments 1 to 71, wherein said bacterium has an increased gastro-intestinal (GI) transit time when compared to a corresponding bacterium not comprising said exogenous nucleic acid or not comprising said fusion protein.
73. The bacterium of embodiment 72, wherein said GI transit time is increased by at least about 10%.
74. The bacterium of embodiment 73, wherein said GI transit time is increased by at least about 30%.
75. The bacterium of embodiment 72, wherein said GI transit time is increased from at least about 10% to about 50%.
76. The bacterium of any one of embodiments 1 to 75, wherein said bacterium has increased in vitro mucin-binding capability when compared to a corresponding bacterium not comprising said exogenous nucleic acid or not comprising said fusion protein.
77. The bacterium of embodiment 76, wherein said in vitro mucin-binding capability is increased by at least about 20%.
78. The bacterium of embodiment 77, wherein said in vitro mucin-binding capability is increased by at least about 50%.
79. The bacterium of embodiment 78, wherein said in vitro mucin-binding capability is increased by at least about 100% (about 2×).
80. The bacterium of embodiment 76, wherein said in vitro mucin-binding capability is increased from at least about 20% to about 500%.
81. The bacterium of any one of embodiments 76 to 80, wherein said in vitro mucin-binding capability is measured by binding said bacterium to mucins from porcine stomach followed by:
    (a) detecting light absorbance at 405 nm ($OD_{405}$); or
    (b) staining said bacterium with crystal violet and subsequently detecting light absorbance at 595 nm ($OD_{595}$).
82. The bacterium of any one of embodiments 1 to 81, wherein said bacterium has increased in vitro Caco-2 cell-binding capability when compared to a corresponding bacterium not comprising said exogenous nucleic acid or not comprising said fusion protein.
83. The bacterium of embodiment 82, wherein said in vitro Caco-2 binding capability is increased by at least about 10%.
84. The bacterium of embodiment 83, wherein said in vitro Caco-2 binding capability is increased by at least about 100% (about 2×).
85. The bacterium of embodiment 84, wherein said in vitro Caco-2 binding capability is increased by at least about 400% (about 5×).
86. The bacterium of embodiment 82, wherein said in vitro Caco-2 binding capability is increased from by at least about 10% to about 500%.
87. The bacterium of any one of embodiments 82 to 86, wherein said in vitro Caco-2 binding capability is measured by:
    (a) contacting a culture of said bacterium with Caco-2 cells;
    (b) washing said Caco-2 cells to remove unbound bacterial cells;
    (c) detaching bacterial cells bound to said Caco-2 cells, thereby forming detached bacterial cells; and
    (d) titering said detached bacterial cells.
88. The bacterium of any one of embodiments 1 to 87, wherein said bacterium exhibits increased adherence to intestinal mucosa when compared to a corresponding bacterium not comprising said exogenous nucleic acid or not comprising said fusion protein.
89. The bacterium of embodiment 88, wherein said adherence to intestinal mucosa is increased from at least about 10% to about 500%.
90. A composition comprising the bacterium of any one of embodiments 1 to 89.
91. A pharmaceutical composition comprising the bacterium of any one of embodiments 1 to 89, and a pharmaceutically acceptable carrier.
92. The bacterium of any one of embodiments 1 to 89, the composition of embodiment 90, or the pharmaceutical composition of embodiment 91, for use in the treatment or prevention of a disease selected from the group consisting of an autoimmune disease, an allergy, a metabolic disease, and a gastro-intestinal disease.
93. The bacterium of any one of embodiments 1 to 89, the composition of embodiment 90, or the pharmaceutical composition of embodiment 91, for use in the preparation of a medicament for the treatment or prevention of a disease.
94. The bacterium, the composition, or pharmaceutical composition of embodiment 93, wherein said disease is selected from the group consisting of an autoimmune disease, an allergy, a metabolic disease, a gastro-intestinal disease, and a nutritional defect.
95. A method for the treatment of a disease in a subject in need thereof comprising administering to said subject a therapeutically effective amount of the bacterium of any one of embodiments 1 to 89, the composition of embodiment 90, or the pharmaceutical composition of embodiment 91.
96. The method of embodiment 95, wherein said disease is selected from the group consisting of an autoimmune disease, an allergy, a metabolic disease, a gastro-intestinal disease, and any combination thereof.
97. The method of embodiment 96, wherein said disease is an autoimmune disease.
98. The method of embodiment 97, wherein said autoimmune disease is type-1 diabetes (T1D).
99. The method of embodiment 96, wherein said disease is a metabolic disease.
100. The method of embodiment 99, wherein said metabolic disease is phenylketonuria (PKU).
101. The method of embodiment 96, wherein said disease is a gastro-intestinal disease.
102. The method of embodiment 101, wherein said gastro-intestinal disease is celiac disease.
103. The method of embodiment 101, wherein said gastro-intestinal disease is inflammatory bowel disease (IBD).
104. The method of embodiment 103, wherein said IBD is Crohn's disease or ulcerative colitis.
105. A method for preparing a genetically modified bacterium comprising contacting a bacterium with an exogenous nucleic acid encoding a fusion protein, wherein said exogenous nucleic acid encoding a fusion protein comprises a sequence encoding a cell-adherence polypeptide.
106. The method of embodiment 105, wherein said contacting occurs under conditions sufficient for said bacterium to internalize said exogenous nucleic acid.
107. The method of embodiment 105 or 106, wherein said exogenous nucleic acid is located on a plasmid.
108. The method of embodiment 106 or 107, wherein said exogenous nucleic acid is integrated into a chromosome of said bacterium.
109. The method of any one of embodiments 105 to 108, further comprising culturing said bacterium and expressing said fusion protein in said bacterium.
110. The method of any one of embodiments 105 to 109, wherein said cell-adherence polypeptide is selected from the group consisting of cell and mucus-binding protein A (CmbA), Mub, MapA, MbpL, and any combinations thereof.
111. The method of embodiment 110, wherein said cell-adherence polypeptide is CmbA.
112. The method of embodiment 111, wherein said CmbA is *Lactobacillus reuteri* CmbA.
113. The method of any one of embodiments 105 to 112, wherein said exogenous nucleic acid encoding a fusion protein further comprises a sequence encoding a mucin-binding polypeptide.
114. The method of embodiment 113, wherein said mucin-binding polypeptide is a trefoil factor (TFF) polypeptide.
115. The method of embodiment 114, wherein said exogenous nucleic acid encoding a fusion protein comprises a sequence encoding CmbA and a sequence encoding a TFF polypeptide.
116. The method of any one of embodiments 105 to 115, wherein said exogenous nucleic acid encoding a fusion protein is integrated into the chromosome of said bacterium.
117. The method of embodiment 116, wherein said exogenous nucleic acid is integrated into the chromosome of said bacterium using homologous recombination.
118. The method of any one of embodiments 105 to 117, further comprising contacting said bacterium with an exogenous nucleic acid encoding a therapeutic polypeptide.
119. The method of embodiment 118, wherein said contacting said bacterium with an exogenous nucleic acid encoding a therapeutic polypeptide occurs prior to said contacting said bacterium with an exogenous nucleic acid encoding a fusion protein.
120. The method of embodiment 118, wherein said contacting said bacterium with an exogenous nucleic acid encoding a therapeutic polypeptide occurs subsequent to said contacting said bacterium with an exogenous nucleic acid encoding a fusion protein.
121. The method of any one of embodiments 105 to 120, wherein said genetically modified bacterium exhibits increased muco- and cell-adhesive properties when compared to a corresponding bacterium not comprising said exogenous nucleic acid encoding a fusion protein.
122. The method of any one of embodiments 105 to 121, further comprising combining a culture of said genetically modified bacterium with at least one cryopreserving agent to form a bacterial mixture.
123. The method of embodiment 122 further comprising freeze-drying said bacterial mixture to form a freeze-dried composition.
124. The method of any one of embodiments 105 to 121 or embodiment 123 further comprising combining said genetically modified bacterium, or said freeze-dried composition with a pharmaceutically acceptable carrier to form a pharmaceutical composition.
125. The method of embodiment 123 or 124 further comprising formulating said freeze-dried composition or said pharmaceutical composition into a pharmaceutical dosage form.
126. A genetically modified bacterium prepared by the method of any one of embodiments 105 to 125.
127. A unit dosage form comprising the bacterium of any one of embodiments 1 to 89, the composition of embodiment 90, or the pharmaceutical composition of embodiment 91.
128. The unit dosage form of embodiment 127, wherein said unit dosage form is an oral dosage form.
129. The unit dosage form of embodiment 128, wherein said oral dosage form is selected from the group consisting of a tablet, a capsule, a sachet, and a packaged liquid.
130. A method for enhancing growth in a mammal comprising administering to said mammal an effective amount of the bacterium of any one of embodiments 1 to 89, the composition of embodiment 90, the pharmaceutical composition of embodiment 91, or the unit dosage form of any one of embodiments 127 to 129.
131. The method of embodiment 130, wherein said mammal is selected from the group consisting of a human, a pig, a cow, and a sheep.
132. The method of embodiment 130 or 131, wherein said bacterium, said composition, said pharmaceutical composition, or said unit dosage form is formulated for administration to said mammal.
133. The method of any one of embodiments 130 to 132, wherein said bacterium comprises an exogenous nucleic acid encoding a growth factor.
134. The method of embodiment 133, wherein said growth factor is constitutively expressed in said bacterium.
135. The method of embodiment 133 or 134, wherein said growth factor is EGF.
136. The method of embodiment 135, wherein said mammal is a pig and said EGF is porcine EGF.
137. A method of increasing binding of a bacterium to intestinal mucosa comprising:
(a) contacting said microorganism with an exogenous nucleic acid encoding a fusion protein, wherein said exogenous nucleic acid encoding a fusion protein comprises a sequence encoding a CmbA polypeptide; and
(b) expressing said exogenous nucleic acid encoding a fusion protein in said bacterium.
138. The method of embodiment 137, wherein said exogenous nucleic acid encoding a fusion protein further comprises a sequence encoding a TFF polypeptide.
139. The method of embodiment 138, wherein expression of said exogenous nucleic acid encoding a fusion protein produces a fusion protein comprising said TFF and said CmbA.
140. A kit comprising (1) a bacterium according to any one of embodiments 1 to 89, a composition according to embodiment 90, a pharmaceutical composition of embodiment 91, or a unit dosage form of any one of embodiments 127 to 129, and (2) instructions for administering said bacterium, said composition, said pharmaceutical composition, or said unit dosage form to a mammal.
141. The kit of embodiment 140, wherein said mammal is a human.
142. A nucleic acid encoding a fusion protein, said nucleic acid comprising:
(i) a sequence encoding a cell-adherence polypeptide selected from the group consisting of cell and mucus-binding protein A (CmbA), Mub, MapA, MbpL, and any combinations thereof; and
(ii) a sequence encoding a mucin-binding polypeptide selected from a TFF polypeptide, MubBP, and a combination thereof.
143. The nucleic acid of embodiment 142, wherein said mucin-binding polypeptide is a TFF polypeptide.
144. The nucleic acid of embodiment 143, wherein said TFF polypeptide is TFF3.
145. The nucleic acid of any one of embodiments 142 to 144, wherein said cell-adherence polypeptide is CmbA.
146. A plasmid comprising the nucleic acid of any one of embodiments 142 to 145.
147. A bacterial host cell comprising the plasmid of embodiment 146.

What is claimed is:

1. A recombinant lactic acid bacterium (LAB) for treating a disease in a subject in need thereof comprising:
(i) a first exogenous nucleic acid encoding a fusion protein; and
(ii) a second exogenous nucleic acid encoding a therapeutic polypeptide, wherein said fusion protein comprises:
(a) an N-terminal trefoil factor (TFF) polypeptide; and
(b) a C-terminal cell adherence polypeptide comprising a cell-wall anchoring domain,
and wherein said therapeutic polypeptide, upon administering said recombinant LAB to said subject, is capable of being delivered to a mucosal tissue of said subject to treat said disease.

2. The recombinant LAB of claim 1, wherein said disease is type-1 diabetes (T1D) or celiac disease.

3. The recombinant LAB of claim 1, wherein said cell adherence polypeptide is a cell and mucus-binding protein A (CmbA), a mucus binding protein (Mub), a mucus adhesion promoting protein (MapA), or a lactococcal mucin binding protein (MbpL).

4. The recombinant LAB of claim 3, wherein said cell adherence polypeptide is a CmbA.

5. The recombinant LAB of claim 3, wherein said CmbA is a *Lactobacillus reuteri* CmbA.

6. The recombinant LAB of claim 3, wherein said CmbA comprises an amino acid sequence at least 80% identical to SEQ ID NO: 1.

7. The recombinant LAB of claim 1, wherein said TFF polypeptide is a TFF1, a TFF2, or a TFF3.

8. The recombinant LAB of claim 1, wherein said TFF polypeptide comprises an amino acid sequence at least 80% identical to SEQ ID NO: 3.

9. The recombinant LAB of claim 1, wherein said fusion protein comprises a CmbA and a human TFF3 polypeptide.

10. The recombinant LAB of claim 1, wherein said fusion protein or said therapeutic polypeptide further comprises a secretion signal peptide.

11. The recombinant LAB of claim 10, wherein said secretion signal peptide is a secretion leader of an unidentified secreted 45-kDa protein (SSusp45).

12. The recombinant LAB of claim 1, wherein said first exogenous nucleic acid is operably linked to a thyA promoter (PthyA), an hllA promoter (PhllA), or a gapB promoter (PgapB).

13. The recombinant LAB of claim 1, wherein said second exogenous nucleic acid is operably linked to a gapB promoter (PgapB).

14. The recombinant LAB of claim 1, wherein said therapeutic polypeptide is:
(i) an IL-2 or an IL-10;
(ii) a proinsulin (PINS), a glutamic acid decarboxylase (GAD65), an insulinoma-associated protein 2 (IA-2), an islet-specific glucose-6-phosphatase catalytic subunit-related protein (IGRP), a zinc transporter 8 (ZnT8), a chromogranin A, a (prepro) islet amyloid polypeptide (ppIAPP), a peripherin, or a citrullinated glucose-regulated protein (GRP); or
(iii) a gluten allergen comprising a gliadin epitope.

15. The recombinant LAB of claim 1, wherein said recombinant LAB is a *Lactobacillus* species (sp.) bacterium, a *Bifidobacterium* sp. bacterium, a *Streptococcus* sp. bacterium, an *Enterococcus* sp. bacterium, or a *Lactococcus* sp. bacterium.

16. The recombinant LAB of claim 15, wherein said LAB is a *Lactococcus lactis*.

17. The recombinant LAB of claim 1, wherein said recombinant LAB has at least one feature that is different from a corresponding LAB lacking said first exogenous nucleic acid, wherein said at least one feature is:
(i) an increased gastro-intestinal (GI) transit time of at least 10%;
(ii) an increased adherence to an intestinal mucosa of at least 10%;
(iii) an increased in vitro mucin-binding capability of at least 20%; or
(iv) an increased in vitro Caco-2 cell-binding capability of at least 10%.

18. The recombinant LAB of claim 1, wherein said recombinant LAB further comprises at least one mutation or insertion that increases trehalose accumulation in said recombinant LAB, wherein said at least one mutation or insertion is:
(i) an insertion of a first polycistronic expression cassette comprising, in 5' to 3' order, a usp45 promoter, a usp45 gene, an intergenic region that is immediately 5' to an rpmD gene, and a nucleic acid encoding an OtsB from *Escherichia coli;*
(ii) an insertion of a second polycistronic expression cassette comprising, in 5' to 3' order, an hllA promoter (PhllA) and a nucleic acid comprising trehalose transporter genes llmg_0453 and llmg_0454;
(iii) an inactivated endogenous trehalose 6-phosphate phosphorylase gene (trePP), wherein said trePP gene is inactivated by gene deletion and said recombinant LAB lacks TrePP activity; or
(iv) an inactivated endogenous cellobiose-specific PTS system IIC component (ptcC) gene, wherein said ptcC gene is inactivated by insertion of a premature stop codon and said recombinant LAB lacks PtcC activity.

19. The recombinant LAB of claim 1, wherein said therapeutic polypeptide comprises (i) a gluten allergen comprising gliadin epitope, and (ii) a secretion signal peptide.

20. A method for treating celiac disease in a subject in need thereof comprising administering to said subject a therapeutically effective amount of said recombinant LAB of claim 19.

21. The recombinant LAB of claim 1, wherein said recombinant LAB expresses a PINS and an IL-10,
wherein said PINS is expressed as a fusion protein comprising a Usp45 secretion leader (SSusp45) from a polycistronic expression cassette comprising, in 5' to 3' order, a gapB promoter, a gapB gene, an intergenic region that is immediately 5' to an rpmD gene, a nucleic acid sequence encoding said SSusp45, and a nucleic acid sequence encoding said PINS, and
wherein said IL-10 is expressed as a fusion protein comprising an SSusp45 from a polycistronic expression cassette comprising, in 5' to 3' order, a hllA promoter, a nucleic acid sequence encoding said SSusp 45, and a nucleic acid sequence encoding said IL-10.

22. A method for treating type-1 diabetes (T1D) in a subject in need thereof comprising administering to said subject a therapeutically effective amount of said recombinant LAB of claim 21.

* * * * *

SEQUENCE LISTING

<160> NUMBER OF SEQ ID NOS: 25

<210> SEQ ID NO 1
<211> LENGTH: 838
<212> TYPE: PRT
<213> ORGANISM: Lactobacillus reuteri
<220> FEATURE:
<221> NAME/KEY: MISC_FEATURE
<222> LOCATION: (1)..(50)
<223> OTHER INFORMATION: Signal sequence
<220> FEATURE:
<221> NAME/KEY: MISC_FEATURE
<222> LOCATION: (51)..(838)
<223> OTHER INFORMATION: Mature protein

<400> SEQUENCE: 1

```
Met Leu Ser Arg Lys Asn Tyr Lys Glu Thr Ile Arg Lys Gln Thr Pro
1               5                   10                  15

Thr Lys Gln Tyr Tyr Thr Ile Lys Lys Leu Thr Val Gly Val Thr Ser
            20                  25                  30

Val Leu Ile Gly Leu Ser Phe Met Gly Glu Leu Glu Gly Asp Ser Val
        35                  40                  45

His Ala Asp Thr Met Thr Ala Ser Ser Glu Ser Thr Ser Val Thr Ser
    50                  55                  60

Thr Thr Ala Gln Asp Gly Leu Lys Lys Ser Pro Gln Leu Tyr Leu Gln
65                  70                  75                  80

Val Thr Asp Thr Asn Asn Pro Ser Thr Pro Leu Ser Ala Ser Ser Thr
                85                  90                  95

Gly Thr Ser Lys Asn Val Thr Ser Ser Ala Ala Val Gln Val Lys Ser
            100                 105                 110

Ala Ser Asp Glu Glu Asp Ser Asp Ser Thr Leu Ala Lys Gly Glu Asn
        115                 120                 125

Lys Phe Ala Arg Ser Ala Val Lys Asp Ser Val Thr Asp Gly Lys Thr
    130                 135                 140

Ser Thr Ala Glu Ile Asn Pro Ala Lys Leu Ser Ser Pro Ala Leu Ile
145                 150                 155                 160

Thr Gln Leu Asn Gln Ser Leu Ala Lys Ser Ser Thr Ser Asp Ala Ala
                165                 170                 175

Lys Ala Asn Asp Glu Leu Glu Ile Lys Ala Thr Asp Pro Thr Asn Tyr
            180                 185                 190

Pro Asn Cys Gly Asp Val Tyr Gly Pro Leu Phe Glu Leu Asp Ala Ser
        195                 200                 205

Gly Gln Leu Val Asn Lys Asp Glu Val Ile Ser Leu Lys Asp Met Tyr
    210                 215                 220

Ile Phe Gln Ile Leu Lys Leu Val Asn Thr Lys Asp Ser Asp Phe Gln
225                 230                 235                 240

Tyr Val Ile Leu Thr Met Asn Arg Lys Asp Thr Ala Asp Arg Ser Val
                245                 250                 255

Tyr Leu Phe Val Thr Gly Ser Asn Tyr Ser Asn Ala Val Val Val Lys
            260                 265                 270

Val Lys Pro Asn Asp Thr Tyr Glu Leu Ser Lys Thr Gly Tyr Ser Val
        275                 280                 285

Thr Tyr Thr Glu Pro Thr Thr Ile Asn Gly His Tyr Val Asp Gly Thr
    290                 295                 300

Phe Tyr Val Thr Gly Ser Thr Tyr Asp Asp Gly Phe Ile Met Pro Asp
305                 310                 315                 320

Trp Gln Leu Gln His Leu Gln Ile Ile Tyr Ser Leu Gly Asn Tyr Asp
```

-continued

```
                325                 330                 335
Pro Ser Asn Thr Asp Ala Thr Ser Val Cys Glu Ile Met Pro Ser Tyr
                340                 345                 350
Glu Lys Val Pro Val Ile Lys Tyr Ser Gly Val Pro Ser Asn Ile Ser
                355                 360                 365
Gln Pro Lys Val Tyr Ile Thr Gly Phe Thr Gly Gln Glu Phe Asn Val
                370                 375                 380
Thr Asp Ile Ile Asn Asn Tyr Lys Lys Val Phe Lys Gly Tyr Tyr Leu
385                 390                 395                 400
Gln Asn Pro Asn Val Ala Ser Met Gly Thr Leu Ser Gln Phe Glu Asn
                405                 410                 415
Gly Gly Tyr Tyr Leu Lys Thr Tyr Tyr Asp Asn Asp Gly Asn Val Asp
                420                 425                 430
Phe Lys Gly Leu Tyr His Gln Ile Asp Asp Gln Gly Thr Met Ser Val
                435                 440                 445
Ser Val Leu Asn Ala Asp Asn Lys Thr Ile Val Gly Pro Glu Asn Ile
                450                 455                 460
Leu Ala Gly Lys Ser His Asn Phe Asn Phe Asn Gly His Asn Trp Ile
465                 470                 475                 480
Ala Arg Asn Pro Tyr Val Thr Ser Ser Ala His Glu Val Ile Leu Lys
                485                 490                 495
Tyr Ala Lys Leu Gly Ser Val Ile Pro Val Asp Glu Asn Gly Asn Lys
                500                 505                 510
Ile Asn Asp Gly Trp Gln Tyr Val Asn Asp Pro Asp Asp Ala Ser Lys
                515                 520                 525
Ala Thr Ser Pro Tyr Glu Lys Ala Pro Val Ile Asp Gly Tyr Val Ala
                530                 535                 540
Val Asn Pro Asp Glu Thr Ile Val Leu Pro His Asn Leu Ser Ser Asp
545                 550                 555                 560
Thr Lys Ile Tyr Tyr Arg Lys Arg Ile Lys Val Thr Tyr Ser Gly Ser
                565                 570                 575
Asp Ser Lys Thr Tyr Asp Gly Asn Pro Ala Asn Phe Glu Pro Thr Thr
                580                 585                 590
Val Gln Trp Ser Gly Leu Lys Gly Leu Asn Thr Ser Thr Leu Thr Ser
                595                 600                 605
Ala Asp Phe Thr Trp Asn Thr Ala Asp Lys Lys Ala Pro Thr Asp Ala
                610                 615                 620
Gly Lys Tyr Thr Leu Ser Leu Asn Thr Gly Glu Ala Ala Leu Arg
625                 630                 635                 640
Lys Ala Asn Pro Asn Tyr Asp Leu Lys Thr Ile Ser Gly Ser Tyr Thr
                645                 650                 655
Tyr Thr Ile Asn Pro Leu Gly Ile Val Thr Val Asn Tyr Lys Gly Tyr
                660                 665                 670
Asp Lys Lys Val Tyr Asp Gly Gln Pro Gly Thr Ile Asn Pro Gly Lys
                675                 680                 685
Leu Thr Trp Ser Lys Leu Pro Asp Gly Thr Ser Leu Lys Met Pro Thr
                690                 695                 700
Trp Ser Ile Asp Asp Phe Ala Trp Glu Thr Ala Asp Gly Leu Ala Pro
705                 710                 715                 720
Thr Ala Val Gly Thr Tyr Arg Ile Ile Leu Thr Asp Ala Gly Lys Ala
                725                 730                 735
Ala Leu Lys Lys Ile Asn Pro Asn Tyr Asp Leu Ser Ser Ile Thr Gly
                740                 745                 750
```

```
Val Phe Thr Tyr Glu Ile Lys Pro Ala Gln Thr Pro Glu Ile Leu Gly
        755                 760                 765

Gln Thr Pro Glu Gln Pro Gly Gln Asn Thr Asn Gln Ser Gly Ala
    770                 775                 780

Glu Asn Gly Phe Gly Ser Ser Thr Arg Pro Asn Ala Ser Thr Asn Ser
785                 790                 795                 800

Asn Leu Asn Gln Leu Pro Gln Thr Gly Asn Glu His Ser Asn Thr Ala
                805                 810                 815

Leu Ala Gly Leu Ala Leu Ala Phe Leu Thr Ala Met Leu Gly Leu Gly
                820                 825                 830

Lys Lys Arg Lys His Asp
        835

<210> SEQ ID NO 2
<211> LENGTH: 2517
<212> TYPE: DNA
<213> ORGANISM: Lactobacillus reuteri
<220> FEATURE:
<221> NAME/KEY: misc_feature
<222> LOCATION: (1)..(150)
<223> OTHER INFORMATION: Signal sequence
<220> FEATURE:
<221> NAME/KEY: misc_feature
<222> LOCATION: (151)..(2514)
<223> OTHER INFORMATION: Mature protein
<220> FEATURE:
<221> NAME/KEY: misc_feature
<222> LOCATION: (2515)..(2517)
<223> OTHER INFORMATION: Stop codon

<400> SEQUENCE: 2
atgctatcaa gaaaaaatta taaggaaact atacgaaaac agacacctac aaaacagtac    60
tatactatta agaaattaac tgttggggtt acttcggtat taattggtct atcctttatg   120
ggagaactag aagggatag cgttcatgcg gacacgatga cagcaagcag tgagtcaaca    180
agtgttacgt cgacgactgc tcaggatggt ttaaaaaat ctccacaact ctatttgcaa    240
gttactgata caaataaccc aagtacacca ttaagtgctt catccacagg gactagtaag   300
aatgttacct catcagctgc ggtacaagtg aagtccgcta gtgatgaaga agatagtgat   360
tctacactag ctaagggaga aaataaattt gctcggtcag cagtaaaaga ttcagtcact   420
gatgggaaaa caagtacagc agaaattaat ccggcaaaat taagcagtcc tgctttaata   480
acgcaactca accaatcctt agctaagagc agtacgagtg atgcagcaaa agctaatgat   540
gagttagaaa ttaaagcaac agatccgact aattatccaa actgtggcga tgtgtatggg   600
ccattatttg aattggatgc tagcggacag cttgttaata agatgaagt tatatctctt   660 aaagatatgt atattttcca aatattgaaa ttagtaaata caaagatag tgactttcaa   720 tatgtaatat aacaatgaa tcgtaaagat actgcagata ggtctgtata tcttttttgta   780 actggaagca attatagtaa tgctgttgtt gttaaagtaa agccaaatga tacttatgaa   840
ttaagtaaaa ctggatatag tgttacttat acagaaccaa caactataaa tggacattat   900
gttgatggaa cttttatgt tacaggaagt acttacgatg atggtttat aatgccagat   960 tggcaactgc agcaccttca gattatatat agttaggaa attatgatcc aagcaatact  1020
gacgcaacat cagtttgtga ataatgcca agttatgaaa aggtaccggt aattaaatat  1080
agtggagtac cttcaaatat tagccaacct aaggtttaca ttaccgggtt tacgggtcaa  1140
gagtttaacg ttacagatat tattaacaat tataagaaag tttttaaggg ctactatctt  1200
```

```
caaaatccta atgtggcgtc catgggaact ctttcccaat ttgagaatgg tggttattac    1260
ttaaagacat attatgataa tgatggtaat gttgacttta agggcttgta tcatcaaatt    1320
gatgatcagg gaacaatgag tgtgagtgtt cttaatgcag ataataaaac aattgttgga    1380
cctgaaaata ttcttgctgg taaatcgcat aactttaact ttaatggtca taactggatt    1440
gcgcggaatc cttatgtcac tagttcagct cacgaagtca tattaaagta tgctaagtta    1500
ggttcagtta ttcctgttga tgaaaacgga aataaaataa cgatggatg caatatgtt     1560 aatgatccag atgatgcttc caaagccact agcccatatg aaaaagcgcc agttatcgat    1620
ggttatgtag ctgtaaatcc agatgaaacg atcgttcttc ctcataactt aagtagtgac    1680
acaaagattt attaccgaaa gaggattaaa gttacctata gtggtagtga cagcaagacc    1740
tacgatggta acccagctaa cttcgagcca cgacagttc agtggagtgg cttgaaagga     1800
ctgaacactt caaccttaac gtccgctgac ttcacgtgga atactgcgga taagaaggca    1860
ccaacggatg ccgtaagta cacacttagt ttgaatacga ccggagaagc agccttacgt      1920
aaggctaacc cgaactatga tctcaagaca attagcggta gttacaccta cacgattaat    1980
ccactaggga ttgtgactgt aaattacaag ggctatgata agaaagtcta tgatggtcaa    2040
cctgaaacga ttaatccggg taaattaacg tggagtaagt tgccagatgg tacttcattg    2100
aagatgccaa catggagtat agatgatttc gcttgggaaa cagctgatgg cttagcacca    2160
acggcagtag gaacttatcg gattatcttg acggatgctg gtaaggctgc actaaagaag    2220
attaatccaa attatgactt aagcagtatt actggtgtct ttacttatga aattaagcca    2280
gcacagacac cagaaatctt aggccaaaca cctgagcaac aaccaggcca aaatactaat    2340
caatcaggag ctgaaaacgg ctttggttct tctacaaggc ctaatgcatc aactaactcc    2400
aatcttaatc aacttccaca gactggtaat gagcattcta atactgcact tgctggtcta    2460
gcattggctt tcttgactgc tatgcttggt ttgggcaaga agcgtaaaca tgattaa       2517
```

<210> SEQ ID NO 3
<211> LENGTH: 59
<212> TYPE: PRT
<213> ORGANISM: Homo sapiens

<400> SEQUENCE: 3

```
Glu Glu Tyr Val Gly Leu Ser Ala Asn Gln Cys Ala Val Pro Ala Lys
1               5                   10                  15

Asp Arg Val Asp Cys Gly Tyr Pro His Val Thr Pro Lys Glu Cys Asn
            20                  25                  30

Asn Arg Gly Cys Cys Phe Asp Ser Arg Ile Pro Gly Val Pro Trp Cys
        35                  40                  45

Phe Lys Pro Leu Gln Glu Ala Glu Cys Thr Phe
    50                  55
```

<210> SEQ ID NO 4
<211> LENGTH: 180
<212> TYPE: DNA
<213> ORGANISM: Homo sapiens

<400> SEQUENCE: 4

```
gaagaatacg ttggtctttc agctaaccaa tgtgctgttc cagctaaaga tcgtgttgat      60
tgtggttacc cacacgttac tccaaaagaa tgtaacaacc gtggttgttg ttttgattca     120
cgtatcccag gtgttccatg gtgttttaaa ccacttcaag aagctgaatg tacttttaa      180
```

<210> SEQ ID NO 5
<211> LENGTH: 27
<212> TYPE: PRT
<213> ORGANISM: Lactococcus lactis

<400> SEQUENCE: 5

Met Lys Lys Lys Ile Ile Ser Ala Ile Leu Met Ser Thr Val Ile Leu
1               5                   10                  15

Ser Ala Ala Pro Leu Ser Gly Val Tyr Ala
            20                  25

<210> SEQ ID NO 6
<211> LENGTH: 81
<212> TYPE: DNA
<213> ORGANISM: Lactococcus lactis

<400> SEQUENCE: 6
atgaaaaaaa agattatctc agctatttta atgtctacag tgatactttc tgctgcagcc      60
ccgttgtcag gtgtttacgc c                                                81

<210> SEQ ID NO 7
<211> LENGTH: 81
<212> TYPE: DNA
<213> ORGANISM: Lactococcus lactis

<400> SEQUENCE: 7
atgaagaaga aaatcattag tgccatctta atgtctacag tgattctttc agctgcagct      60
cctttatcag gcgtttatgc a                                                81

<210> SEQ ID NO 8
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(27)
<223> OTHER INFORMATION: SSusp45
<220> FEATURE:
<221> NAME/KEY: MISC_FEATURE
<222> LOCATION: (28)..(86)
<223> OTHER INFORMATION: hTFF3

<400> SEQUENCE: 8

Met Lys Lys Lys Ile Ile Ser Ala Ile Leu Met Ser Thr Val Ile Leu
1               5                   10                  15

Ser Ala Ala Pro Leu Ser Gly Val Tyr Ala Glu Glu Tyr Val Gly
            20                  25                  30

Leu Ser Ala Asn Gln Cys Ala Val Pro Ala Lys Asp Arg Val Asp Cys
        35                  40                  45

Gly Tyr Pro His Val Thr Pro Lys Glu Cys Asn Asn Arg Gly Cys Cys
    50                  55                  60

Phe Asp Ser Arg Ile Pro Gly Val Pro Trp Cys Phe Lys Pro Leu Gln
65                  70                  75                  80

Glu Ala Glu Cys Thr Phe
                85

<210> SEQ ID NO 9
<211> LENGTH: 261
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(258)
<223> OTHER INFORMATION: CDS
<220> FEATURE:
<221> NAME/KEY: misc_feature
<222> LOCATION: (1)..(81)
<223> OTHER INFORMATION: SSusp45
<220> FEATURE:
<221> NAME/KEY: misc_feature
<222> LOCATION: (82)..(258)
<223> OTHER INFORMATION: hTFF3
<220> FEATURE:
<221> NAME/KEY: misc_feature
<222> LOCATION: (259)..(261)
<223> OTHER INFORMATION: Stop codon

<400> SEQUENCE: 9
atgaaaaaaa agattatctc agctatttta atgtctacag tgatactttc tgctgcagcc      60
ccgttgtcag gtgtttacgc cgaagaatac gttggtcttt cagctaacca atgtgctgtt     120
ccagctaaag atcgtgttga ttgtggttac ccacacgtta ctccaaaaga atgtaacaac     180
cgtggttgtt gttttgattc acgtatccca ggtgttccat ggtgttttaa accacttcaa     240
gaagctgaat gtactttta a                                                261

<210> SEQ ID NO 10
<211> LENGTH: 874
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(27)
<223> OTHER INFORMATION: SSusp45
<220> FEATURE:
<221> NAME/KEY: MISC_FEATURE
<222> LOCATION: (28)..(86)
<223> OTHER INFORMATION: hTFF3
<220> FEATURE:
<221> NAME/KEY: MISC_FEATURE
<222> LOCATION: (87)..(874)
<223> OTHER INFORMATION: CmbA

<400> SEQUENCE: 10

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Glu Glu Tyr Val Gly
                20                  25                  30

Leu Ser Ala Asn Gln Cys Ala Val Pro Ala Lys Asp Arg Val Asp Cys
            35                  40                  45

Gly Tyr Pro His Val Thr Pro Lys Glu Cys Asn Asn Arg Gly Cys Cys
        50                  55                  60

Phe Asp Ser Arg Ile Pro Gly Val Pro Trp Cys Phe Lys Pro Leu Gln
65                  70                  75                  80

Glu Ala Glu Cys Thr Phe Asp Thr Met Thr Ala Ser Ser Glu Ser Thr
                85                  90                  95

Ser Val Thr Ser Thr Thr Ala Gln Asp Gly Leu Lys Lys Ser Pro Gln
                100                 105                 110

Leu Tyr Leu Gln Val Thr Asp Thr Asn Asn Pro Ser Thr Pro Leu Ser
            115                 120                 125
```

-continued

```
Ala Ser Ser Thr Gly Thr Ser Lys Asn Val Thr Ser Ser Ala Ala Val
130                 135                 140

Gln Val Lys Ser Ala Ser Asp Glu Glu Asp Ser Asp Ser Thr Leu Ala
145                 150                 155                 160

Lys Gly Glu Asn Lys Phe Ala Arg Ser Ala Val Lys Asp Ser Val Thr
                165                 170                 175

Asp Gly Lys Thr Ser Thr Ala Glu Ile Asn Pro Ala Lys Leu Ser Ser
            180                 185                 190

Pro Ala Leu Ile Thr Gln Leu Asn Gln Ser Leu Ala Lys Ser Ser Thr
            195                 200                 205

Ser Asp Ala Ala Lys Ala Asn Asp Glu Leu Glu Ile Lys Ala Thr Asp
210                 215                 220

Pro Thr Asn Tyr Pro Asn Cys Gly Asp Val Tyr Gly Pro Leu Phe Glu
225                 230                 235                 240

Leu Asp Ala Ser Gly Gln Leu Val Asn Lys Asp Glu Val Ile Ser Leu
                245                 250                 255

Lys Asp Met Tyr Ile Phe Gln Ile Leu Lys Leu Val Asn Thr Lys Asp
            260                 265                 270

Ser Asp Phe Gln Tyr Val Ile Leu Thr Met Asn Arg Lys Asp Thr Ala
            275                 280                 285

Asp Arg Ser Val Tyr Leu Phe Val Thr Gly Ser Asn Tyr Ser Asn Ala
290                 295                 300

Val Val Val Lys Val Lys Pro Asn Asp Thr Tyr Glu Leu Ser Lys Thr
305                 310                 315                 320

Gly Tyr Ser Val Thr Tyr Thr Glu Pro Thr Thr Ile Asn Gly His Tyr
                325                 330                 335

Val Asp Gly Thr Phe Tyr Val Thr Gly Ser Thr Tyr Asp Asp Gly Phe
            340                 345                 350

Ile Met Pro Asp Trp Gln Leu Gln His Leu Gln Ile Ile Tyr Ser Leu
            355                 360                 365

Gly Asn Tyr Asp Pro Ser Asn Thr Asp Ala Thr Ser Val Cys Glu Ile
370                 375                 380

Met Pro Ser Tyr Glu Lys Val Pro Val Ile Lys Tyr Ser Gly Val Pro
385                 390                 395                 400

Ser Asn Ile Ser Gln Pro Lys Val Tyr Ile Thr Gly Phe Thr Gly Gln
                405                 410                 415

Glu Phe Asn Val Thr Asp Ile Ile Asn Asn Tyr Lys Lys Val Phe Lys
            420                 425                 430

Gly Tyr Tyr Leu Gln Asn Pro Asn Val Ala Ser Met Gly Thr Leu Ser
            435                 440                 445

Gln Phe Glu Asn Gly Gly Tyr Tyr Leu Lys Thr Tyr Tyr Asp Asn Asp
450                 455                 460

Gly Asn Val Asp Phe Lys Gly Leu Tyr His Gln Ile Asp Asp Gln Gly
465                 470                 475                 480

Thr Met Ser Val Ser Val Leu Asn Ala Asp Asn Lys Thr Ile Val Gly
                485                 490                 495

Pro Glu Asn Ile Leu Ala Gly Lys Ser His Asn Phe Asn Phe Asn Gly
            500                 505                 510

His Asn Trp Ile Ala Arg Asn Pro Tyr Val Thr Ser Ser Ala His Glu
            515                 520                 525

Val Ile Leu Lys Tyr Ala Lys Leu Gly Ser Val Ile Pro Val Asp Glu
530                 535                 540

Asn Gly Asn Lys Ile Asn Asp Gly Trp Gln Tyr Val Asn Asp Pro Asp
```

```
                545                 550                 555                 560
Asp Ala Ser Lys Ala Thr Ser Pro Tyr Glu Lys Ala Pro Val Ile Asp
                565                 570                 575

Gly Tyr Val Ala Val Asn Pro Asp Glu Thr Ile Val Leu Pro His Asn
                580                 585                 590

Leu Ser Ser Asp Thr Lys Ile Tyr Arg Lys Arg Ile Lys Val Thr
                595                 600                 605

Tyr Ser Gly Ser Asp Ser Lys Thr Tyr Asp Gly Asn Pro Ala Asn Phe
                610                 615                 620

Glu Pro Thr Thr Val Gln Trp Ser Gly Leu Lys Gly Leu Asn Thr Ser
625                 630                 635                 640

Thr Leu Thr Ser Ala Asp Phe Thr Trp Asn Thr Ala Asp Lys Lys Ala
                645                 650                 655

Pro Thr Asp Ala Gly Lys Tyr Thr Leu Ser Leu Asn Thr Thr Gly Glu
                660                 665                 670

Ala Ala Leu Arg Lys Ala Asn Pro Asn Tyr Asp Leu Lys Thr Ile Ser
                675                 680                 685

Gly Ser Tyr Thr Tyr Thr Ile Asn Pro Leu Gly Ile Val Thr Val Asn
                690                 695                 700

Tyr Lys Gly Tyr Asp Lys Lys Val Tyr Asp Gly Gln Pro Gly Thr Ile
705                 710                 715                 720

Asn Pro Gly Lys Leu Thr Trp Ser Lys Leu Pro Asp Gly Thr Ser Leu
                725                 730                 735

Lys Met Pro Thr Trp Ser Ile Asp Asp Phe Ala Trp Glu Thr Ala Asp
                740                 745                 750

Gly Leu Ala Pro Thr Ala Val Gly Thr Tyr Arg Ile Ile Leu Thr Asp
                755                 760                 765

Ala Gly Lys Ala Ala Leu Lys Lys Ile Asn Pro Asn Tyr Asp Leu Ser
                770                 775                 780

Ser Ile Thr Gly Val Phe Thr Tyr Glu Ile Lys Pro Ala Gln Thr Pro
785                 790                 795                 800

Glu Ile Leu Gly Gln Thr Pro Glu Gln Pro Gly Gln Asn Thr Asn
                805                 810                 815

Gln Ser Gly Ala Glu Asn Gly Phe Gly Ser Ser Thr Arg Pro Asn Ala
                820                 825                 830

Ser Thr Asn Ser Asn Leu Asn Gln Leu Pro Gln Thr Gly Asn Glu His
                835                 840                 845

Ser Asn Thr Ala Leu Ala Gly Leu Ala Leu Ala Phe Leu Thr Ala Met
850                 855                 860

Leu Gly Leu Gly Lys Lys Arg Lys His Asp
865                 870

<210> SEQ ID NO 11
<211> LENGTH: 2625
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(2622)
<223> OTHER INFORMATION: CDS
<220> FEATURE:
<221> NAME/KEY: misc_feature
<222> LOCATION: (1)..(81)
<223> OTHER INFORMATION: SSusp45
<220> FEATURE:
```

```
<221> NAME/KEY: misc_feature
<222> LOCATION: (82)..(258)
<223> OTHER INFORMATION: hTFF3
<220> FEATURE:
<221> NAME/KEY: misc_feature
<222> LOCATION: (259)..(2622)
<223> OTHER INFORMATION: CmbA
<220> FEATURE:
<221> NAME/KEY: misc_feature
<222> LOCATION: (2623)..(2625)
<223> OTHER INFORMATION: Stop codon

<400> SEQUENCE: 11
```

| | | | | | |
|---|---|---|---|---|---|
| atgaaaaaaa | agattatctc | agctatttta | atgtctacag | tgatactttc | tgctgcagcc | 60 |
| ccgttgtcag | gtgtttacgc | cgaagaatac | gttggtcttt | cagctaacca | atgtgctgtt | 120 |
| ccagctaaag | atcgtgttga | ttgtggttac | ccacacgtta | ctccaaaaga | atgtaacaac | 180 |
| cgtggttgtt | gttttgattc | acgtatccca | ggtgttccat | ggtgttttaa | accacttcaa | 240 |
| gaagctgaat | gtactttga | cacgatgaca | gcaagcagtg | agtcaacaag | tgttacgtcg | 300 |
| acgactgctc | aggatggttt | aaaaaaatct | ccacaactct | atttgcaagt | tactgataca | 360 |
| aataacccaa | gtacaccatt | aagtgcttca | tccacaggga | ctagtaagaa | tgttacctca | 420 |
| tcagctgcgg | tacaagtgaa | gtccgctagt | gatgaagaag | atagtgattc | tacactagct | 480 |
| aagggagaaa | ataaatttgc | tcggtcagca | gtaaagatt | cagtcactga | tgggaaaaca | 540 |
| agtacagcag | aaattaatcc | ggcaaaatta | agcagtcctg | ctttaataac | gcaactcaac | 600 |
| caatccttag | ctaagagcag | tacgagtgat | gcagcaaaag | ctaatgatga | gttagaaatt | 660 |
| aaagcaacag | atccgactaa | ttatccaaac | tgtggcgatg | tgtatgggcc | attatttgaa | 720 |
| ttggatgcta | gcggacagct | tgttaataaa | gatgaagtta | tatctcttaa | agatatgtat | 780 |
| attttccaaa | tattgaaatt | agtaaataca | aaagatagtg | actttcaata | tgtaatatta | 840 |
| acaatgaatc | gtaaagatac | tgcagatagg | tctgtatatc | ttttgtaac | tggaagcaat | 900 |
| tatagtaatg | ctgttgttgt | taaagtaaag | ccaaatgata | cttatgaatt | aagtaaaact | 960 |
| ggatatagtg | ttacttatac | agaaccaaca | actataaatg | gacattatgt | tgatggaact | 1020 |
| tttatgtta | caggaagtac | ttacgatgat | ggttttataa | tgccagattg | gcaactgcag | 1080 |
| caccttcaga | ttatatatag | tttaggaaat | tatgatccaa | gcaatactga | cgcaacatca | 1140 |
| gtttgtgaaa | taatgccaag | ttatgaaaag | gtaccggtaa | ttaaatatag | tggagtacct | 1200 |
| tcaaatatta | gccaacctaa | ggtttacatt | accgggttta | cgggtcaaga | gtttaacgtt | 1260 |
| acagatatta | ttaacaatta | taagaaagtt | tttaagggct | actatcttca | aaatcctaat | 1320 |
| gtggcgtcca | tgggaactct | ttcccaattt | gagaatggtg | gttattactt | aaagacatat | 1380 |
| tatgataatg | atggtaatgt | tgactttaag | ggcttgtatc | atcaaattga | tgatcaggga | 1440 |
| acaatgagtg | tgagtgttct | taatgcagat | aataaaacaa | ttgttggacc | tgaaaatatt | 1500 |
| cttgctggta | aatcgcataa | ctttaacttt | aatggtcata | actggattgc | gcggaatcct | 1560 |
| tatgtcacta | gttcagctca | cgaagtcata | ttaaagtatg | ctaagttagg | ttcagttatt | 1620 |
| cctgttgatg | aaaacggaaa | taaaataaac | gatggatggc | aatatgttaa | tgatccagat | 1680 |
| gatgcttcca | aagccactag | cccatatgaa | aaagcgccag | ttatcgatgg | ttatgtagct | 1740 |
| gtaaatccag | atgaaacgat | cgttcttcct | cataacttaa | gtagtgacac | aaagatttat | 1800 |
| taccgaaaga | ggattaaagt | tacctatagt | ggtagtgaca | gcaagaccta | cgatggtaac | 1860 |
| ccagctaact | tcgagccaac | gacagttcag | tggagtggct | tgaaaggact | gaacacttca | 1920 |
| accttaacgt | ccgctgactt | cacgtggaat | actgcggata | agaaggcacc | aacggatgcc | 1980 |

```
ggtaagtaca cacttagttt gaatacgacc ggagaagcag ccttacgtaa ggctaacccg    2040
aactatgatc tcaagacaat tagcggtagt tacacctaca cgattaatcc actagggatt    2100
gtgactgtaa attacaaggg ctatgataag aaagtctatg atggtcaacc tggaacgatt    2160
aatccgggta aattaacgtg gagtaagttg ccagatggta cttcattgaa gatgccaaca    2220
tggagtatag atgatttcgc ttgggaaaca gctgatggct agcaccaac ggcagtagga     2280 acttatcgga ttatcttgac ggatgctggt aaggctgcac taaagaagat taatccaaat    2340
tatgacttaa gcagtattac tggtgtcttt acttatgaaa ttaagccagc acagacacca    2400
gaaatcttag gccaaacacc tgagcaacaa ccaggccaaa atactaatca atcaggagct    2460
gaaaacggct ttggttcttc tacaaggcct aatgcatcaa ctaactccaa tcttaatcaa    2520
cttccacaga ctggtaatga gcattctaat actgcacttg ctggtctagc attggctttc    2580
ttgactgcta tgcttggttt gggcaagaag cgtaaacatg attaa                    2625
```

```
<210> SEQ ID NO 12
<211> LENGTH: 16
<212> TYPE: DNA
<213> ORGANISM: Unknown
<220> FEATURE:
<223> OTHER INFORMATION: Description of Unknown: rpmD sequence

<400> SEQUENCE: 12
taaggaggaa aaaatg                                                      16

<210> SEQ ID NO 13
<211> LENGTH: 10
<212> TYPE: DNA
<213> ORGANISM: Unknown
<220> FEATURE:
<223> OTHER INFORMATION: Description of Unknown: rpmD sequence

<400> SEQUENCE: 13
ggaggaaaaa                                                             10

<210> SEQ ID NO 14
<211> LENGTH: 985
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Lys Lys Lys Ile Ile Ser Ala Ile Leu Met Ser Thr Val Ile Leu
1               5                   10                  15

Ser Ala Ala Pro Leu Ser Gly Val Tyr Ala Phe Asn Gly Ala Val
                20                  25                  30

Val His Ala Asp Thr Pro Ser Asn Asp Lys Pro Val Val Thr Thr
            35                  40                  45

Ile Ala Ser Asn Ser Ser Ala Val Glu Ala Glu Thr Ala Ser Ser Ser
    50                  55                  60

Ser Ser Ser Ala Val Lys Ala Glu Thr Thr Ser Ala Ser Ser Ser Ser
65                  70                  75                  80

Ala Val Lys Ala Glu Thr Ala Ser Ser Ser Ser Ser Ala Val Lys
                85                  90                  95

Ala Glu Thr Thr Ser Ala Ser Ser Ser Ser Ala Val Lys Ala Glu Thr
                100                 105                 110
```

```
Ala Ser Ser Ser Ser Ser Ala Val Lys Ala Glu Thr Ser Ala
            115                 120                 125

Ser Ser Ser Ser Ala Val Lys Ala Glu Thr Thr Ser Ala Ser Ser Ser
        130                 135                 140

Ser Ala Val Lys Ala Glu Thr Ala Ser Ser Ser Ser Ser Ala Val
145                 150                 155                 160

Lys Ala Glu Thr Thr Ser Ala Ser Ser Ser Ala Ala Lys Ala Asp
                165                 170                 175

Thr Thr Ser Ala Ala Ser Ser Ala Ala Lys Ser Asp Ser Ser Leu
            180                 185                 190

Val Lys Gly Arg Val Tyr Ala Ser Thr Tyr Leu Glu Ser Asn Lys Asn
        195                 200                 205

Tyr Tyr Thr Asp Pro Ala Ile Ser Arg Gly Phe Leu Asp Ser Pro Ile
    210                 215                 220

Ser Lys Glu Leu Leu Gly Asp Gln Asn Trp Asn Met Phe Gln Val Ala
225                 230                 235                 240

Val Ser Lys Asn Leu Val Ser Tyr Asn Pro Gly Met Thr Phe Asn Gln
                245                 250                 255

Tyr Tyr Leu Ala Asn Asn Ile Ser Pro Glu Asp Asn Phe Ile Val Tyr
            260                 265                 270

Pro Arg Leu Thr Asn Gln Ile Val Arg Leu Lys Ser Gly Ala Tyr Leu
        275                 280                 285

Asn Ala Asn Pro Asn Pro Lys Gly Ala Lys Asp Asp Ser Gly Asn Ile
    290                 295                 300

Val Asp Tyr Ile Thr Tyr Val Gly Pro Thr Asp Asp Arg Gly Ala Tyr
305                 310                 315                 320

Trp Gly Asp Lys Glu Leu Glu Asp Pro Val Leu Phe Ser Arg Leu Thr
                325                 330                 335

Val Gly Glu Leu Pro Ser Ala Ser Glu Gly Thr Leu Gly Leu Phe Asn
            340                 345                 350

Ser Gly Thr Tyr Leu Phe Pro Thr Gln Ile Gly Tyr Gly Glu Asn Ala
        355                 360                 365

Thr Val Asn Asp Tyr Met Leu Thr Pro Gly Asn Asp Phe Ile Ile Pro
    370                 375                 380

Thr Arg Phe Asn Thr Ile Arg Asn Asp Val Tyr Leu Thr Met Arg Ser
385                 390                 395                 400

Arg Ala Tyr Phe Gly Ala Gly Leu Gln Gly Ala Gln Ala Ser Leu Thr
                405                 410                 415

Ala Thr Ser Asn Gly Lys Pro Val Val Gly Ser Ser Glu Asn Ser Lys
            420                 425                 430

Phe Tyr Ile Asp Thr Asp Ser Asn Val Tyr Leu Thr Lys Gln Gly Phe
        435                 440                 445

Asp Gln Leu Gly Asn Phe Gly Lys Ile Met Ala Pro Phe Val Tyr Thr
    450                 455                 460

Ser Ala Ser Asn Asp Leu Lys Lys Val Gly Ile Asp Lys Phe Ser Ala
465                 470                 475                 480

Met Met Asn Gln Gly Leu Ser Ser Ile Gln Ser Lys Ser Gly Ala Asn
                485                 490                 495

Thr Ile Val Ser Gly Asn Gly Gln Ile Gln Leu Ser Gly Phe Asn
            500                 505                 510

Arg Glu Thr Asp Leu Asp Gly Ala Phe Ser Ser Ile Ser Asp Arg
        515                 520                 525

Glu Asn Asp Ala Leu Lys Asn Thr Asp Val Asn Phe Tyr Met Tyr Thr
```

```
            530                 535                 540
Lys Gly Asn Thr Glu Thr Asn Val Thr Thr Pro Leu Ala Pro Asn Gly
545                 550                 555                 560

Tyr His Leu Tyr Ser Pro Asn Val Ser Glu Phe Lys Ile Gln Thr Thr
                565                 570                 575

Arg Pro Tyr Phe Ser Trp Thr Gly Asp Ile Ser Asn Ala Ile Lys Ile
                580                 585                 590

Ser Glu Ala Asn Ala Asp Phe Asp Asp Leu Leu Gly Ser Asn Ser Leu
                595                 600                 605

Gln Val Thr Asp Asn Gly Val Asp Ser Asp Gly Thr Pro Ile Ser Val
            610                 615                 620

Asp Leu Asn Arg Val Arg Ile Arg Ile Ser Glu Asp Gly Gly Ser Thr
625                 630                 635                 640

Tyr Ser Asn Asp Ser Tyr Thr Leu Asn Asp Leu Lys Ala Leu Leu Thr
                645                 650                 655

Ser Gly Asn Ile Thr Val Pro Lys Ile Val Ala Tyr Thr Tyr Ser
                660                 665                 670

Ala Thr Asp Ser Lys Thr Asp Asn Ile Gly Lys Leu Pro Ser Glu Ile
                675                 680                 685

Asp Asp Asn Thr Gly Ala Tyr Ala Val Pro Phe Thr Arg Thr Leu Thr
            690                 695                 700

Asn Asp Ile Pro Asp Lys Lys Ser Asn Ile Thr Val Lys Tyr Ile Asp
705                 710                 715                 720

Ile Ser Gly Asn Thr Ile Ser Asp Asn Ile Val Lys Ala Gly Asn Val
                725                 730                 735

Gly Asp Ser Tyr Thr Thr Glu Gln Lys Ala Ile Pro Gly Tyr Thr Phe
                740                 745                 750

Lys Ala Val Gln Gly Asn Pro Thr Gly Gln Phe Thr Ser Asp Ala Gln
                755                 760                 765

Thr Val Thr Tyr Val Tyr Thr Lys Asp Pro Val Ala Gly Gly Ser Val
            770                 775                 780

Thr Ala Lys Tyr Val Asp Thr Ser Gly Asn Ala Ile Ser Asp Asn Val
785                 790                 795                 800

Val Lys Thr Gly Asn Ile Gly Asp Thr Tyr Ser Thr Lys Gln Lys Thr
                805                 810                 815

Ile Pro Gly Tyr Thr Phe Lys Glu Val Gln Gly Ser Val Ser Gly Gln
                820                 825                 830

Phe Thr Asn Gln Glu Gln Thr Val Thr Tyr Val Tyr Thr Lys Asp Pro
                835                 840                 845

Val Ala Gly Ala His Ile Ile Ala Lys Tyr Val Asp Glu Asn Gly Asn
850                 855                 860

Thr Ile Ser Asp Asn Val Lys Ser Gly Asn Ile Gly Asp Ser Tyr
865                 870                 875                 880

Thr Thr Glu Gln Lys Ala Ile Pro Gly Tyr Thr Phe Lys Ala Val Gln
                885                 890                 895

Gly Asn Pro Thr Gly Gln Phe Thr Ser Asp Ala Gln Thr Val Thr Tyr
                900                 905                 910

Ile Tyr Thr Lys Val Lys Thr Ser Gly Gly Ser Glu Thr Pro Thr Pro
                915                 920                 925

Ser Lys Thr Ile Ala Thr Lys Ser Ser Thr Asn Thr Ile Ser Ser Ser
            930                 935                 940

Thr Leu Pro Lys Thr Gly Asp Ser Gln Val Ser Thr Leu Phe Gly Met
945                 950                 955                 960
```

```
Val Val Gly Phe Phe Ile Phe Gly Ala Gly Thr Leu Ser Leu Phe Phe
            965                 970                 975
Asn Ser Lys Arg Lys Arg Lys Ser Lys
        980                 985

<210> SEQ ID NO 15
<211> LENGTH: 3180
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (208)..(3162)
<223> OTHER INFORMATION: CDS

<400> SEQUENCE: 15
agctttagaa gaagaaaaag cagctgttga attagagggt tcagaaactg cctgatggat    60 atttttata aatctggttt gaacaaatta tattgacatc tcttttcta tcctgataat    120 tctgagaggt tattttggga aatactattg aaccatatcg aggtggtgtg gtataatgaa    180
gggaattaaa aaagatagga aaatttcatg aaaaaaaaga ttatctcagc tattttaatg    240
tctacagtga tactttctgc tgcagccccg ttgtcaggtg tttacgcttt caatggagcg    300
gtcgtgcacg cggatacacc gagcaatgac aaacctgtgg ttgtaacaac cattgcgtca    360
aactcatctg ccgttgaagc tgagactgcc agcagttctt catcaagtgc cgtaaaagcg    420
gaaacgacca gcgcctcttc ttcaagtgct gtaaaagctg agacagcctc tagcagttca    480
agctcagccg taaaggcaga aactacgagt gcatcatctt catcagcggt aaaggcggag    540
accgctagct cttcttctag tagtgctgtg aaagccgaga cgacgagcgc atcttcatct    600
tctgctgtta aggcggaaac aacaagcgct tctagctcaa gcgccgtcaa agcagaaaca    660
gcgagttcat cttctagtag tgcagttaaa gccgaaacta cctctgccag ctcatcttca    720
gcagcaaagg cggataccac cagcgcagct agttcatctg cggcaaagag cgacagttca    780
cttgtgaaag gcgtgtttta tgcctctacg tatttagagt caaacaagaa ctattatacc    840
gatccggcta tcagtcgtgg cttttttagac agtccgatat ctaaagagtt acttggtgat    900
caaaattgga atatgtttca agttgctgtc agcaagaacc ttgtctcata taatccagga    960
atgacgttta accaatatta cttggcgaat aatatctcac cagaagataa tttcatcgtt   1020
tatcctcgtt taaccaatca aatagtaaga ttaaagagtg gagcctattt gaacgcgaac   1080
cctaacccta aggggcgaa agacgatagt ggcaacatag tcgactacat aacttatgtt   1140
ggccctacgg acgatcgtgg tgcgtactgg ggggacaaag agcttgaaga tccggtgctt   1200
ttctctcgac ttactgtggg tgagttgccg agtgcttctg agggcacgct tggcttgttt   1260
aacagtggaa catatctttt ccctacacaa ataggctacg gtgaaaacgc cacagttaac   1320
gattacatgc ttaccccctgg taatgacttc atcataccaa ctcgatttaa tacgatccgt   1380
aatgacgtgt acttaacgat gcgatctcgt gcatacttcg gggctggatt acaaggggca   1440
caggcaagtt taaccgcaac ctctaatgga aaaccggtag tggggtcatc agagaacagc   1500
aaattttaca tagacacaga cagtaatgtc tatcttacaa aacaggggtt tgatcaactt   1560
ggtaactttg gtaaaataat ggctccattc gtttatacga gcgcttcaaa cgatttgaag   1620
aaggtcggaa tagacaaatt ctcagccatg atgaaccaag ggttgagtag catacaaagc   1680
aagtctgggg caaacaccat cgtatcaggg aacggcggcc agattcaatt gagcggtttc   1740
```

```
aatagagaaa cagacttgga tggagcattc tcatcttcaa taagcgatcg tgagaacgat    1800
gcattaaaga atacagatgt caacttctat atgtatacga aaggcaacac agaaactaat    1860
gtgacgacgc cgttggcccc gaatgggtac cacctttact caccaaacgt atctgaattc    1920
aagatacaga ctaccagacc ttacttctca tggacgggag acataagtaa tgctataaaa    1980
atttctgaag ccaatgcgga tttcgatgat ttacttggta gtaactcatt acaggttact    2040
gataatgggg tggacagcga cggtaccccct atatctgtcg accttaatcg tgtcagaata    2100
agaatatctg aggacggagg gagtacatat tctaacgatt cttatacgct taatgactta    2160
aaagccttat tgaccagcgg aaacatcact gtccctaaga tagttatcgc ttatacctac    2220
tctgcgactg attcaaaaac tgataacatc ggtaagttac cgtctgaaat tgacgacaac    2280
acaggcgcgt acgccgttcc gttcacacgt acgttgacga atgacattcc agataaaaaa    2340
agtaacatta cggtcaagta tatcgatatc tctggtaata ccatatctga taacatagtt    2400
aaagccggta atgttggcga ttcatataca acagaacaaa aagcaatacc gggatacacc    2460
ttcaaagccg tacaaggtaa tccaaccggt caattcacgt ctgatgctca aacagtgacg    2520
tacgtttaca cgaaggatcc agtggcaggc ggcagcgtca ccgctaagta tgtcgatacc    2580
agtgggaacg ccatctctga taacgttgtt aaaaccggta acatcggcga tacctacagt    2640
actaagcaga agaccatacc gggatatact ttcaaagagg ttcaaggatc tgttagcgga    2700
caatttacca atcaggaaca aacggtcact tatgtataca ctaaagatcc ggtcgctggt    2760
gcccatatca tagcaaaata cgtagacgag aatggtaaca cgatatcaga caacgttgtg    2820
aagtcaggta acattgggga ttcttacact actgagcaaa aggcaattcc tggatacact    2880
tttaaagctg ttcagggaaa cccaacggga caattcacca gtgacgccca gacggtgacc    2940
tacatataca ctaaagtgaa aacatctggt gggagcgaaa ccccaacgcc gtcaaaaacg    3000
attgcaacca gtcaagtac aaacacaatc tctagttcta cacttccgaa gacgggcgat    3060
agtcaagtgt ctactttatt cggcatggtg gtggggttct tcatatttgg ggcgggaacc    3120
ttgagcttat ttttttaacag taagcgaaaa agaaagtcaa agtaaattaa tctataagtt    3180
```

<210> SEQ ID NO 16
<211> LENGTH: 998
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Met Val Ser Lys Asn Asn Val Gln Phe Tyr Asp Lys Lys Asn Asp Asn
1               5                   10                  15

Gln Gln Arg Trp Gly Leu Arg Lys Thr Ser Phe Gly Leu Ala Ser Leu
            20                  25                  30

Leu Leu Gly Thr Ser Phe Val Leu Phe Asn Gly Ala Val Val His Ala
        35                  40                  45

Asp Thr Pro Ser Asn Asp Lys Pro Val Val Thr Thr Ile Ala Ser
    50                  55                  60

Asn Ser Ser Ala Val Glu Ala Glu Thr Ala Ser Ser Ser Ser Ser Ser
65                  70                  75                  80

Ala Val Lys Ala Glu Thr Thr Ser Ala Ser Ser Ser Ala Val Lys
                85                  90                  95

Ala Glu Thr Ala Ser Ser Ser Ser Ser Ser Ala Val Lys Ala Glu Thr

```
                100             105                 110
Thr Ser Ala Ser Ser Ser Ala Val Lys Ala Glu Thr Ala Ser Ser
        115                 120                 125
Ser Ser Ser Ser Ala Val Lys Ala Glu Thr Thr Ser Ala Ser Ser
        130                 135                 140
Ser Ala Val Lys Ala Glu Thr Thr Ser Ala Ser Ser Ser Ala Val
145                 150                 155                 160
Lys Ala Glu Thr Ala Ser Ser Ser Ser Ala Val Lys Ala Glu
                165                 170                 175
Thr Thr Ser Ala Ser Ser Ser Ala Ala Lys Ala Asp Thr Thr Ser
                180                 185                 190
Ala Ala Ser Ser Ser Ala Ala Lys Ser Asp Ser Ser Leu Val Lys Gly
                195                 200                 205
Arg Val Tyr Ala Ser Thr Tyr Leu Glu Ser Asn Lys Asn Tyr Tyr Thr
                210                 215                 220
Asp Pro Ala Ile Ser Arg Gly Phe Leu Asp Ser Pro Ile Ser Lys Glu
225                 230                 235                 240
Leu Leu Gly Asp Gln Asn Trp Asn Met Phe Gln Val Ala Val Ser Lys
                245                 250                 255
Asn Leu Val Ser Tyr Asn Pro Gly Met Thr Phe Asn Gln Tyr Tyr Leu
                260                 265                 270
Ala Asn Asn Ile Ser Pro Glu Asp Asn Phe Ile Val Tyr Pro Arg Leu
                275                 280                 285
Thr Asn Gln Ile Val Arg Leu Lys Ser Gly Ala Tyr Leu Asn Ala Asn
                290                 295                 300
Pro Asn Pro Lys Gly Ala Lys Asp Asp Ser Gly Asn Ile Val Asp Tyr
305                 310                 315                 320
Ile Thr Tyr Val Gly Pro Thr Asp Asp Arg Gly Ala Tyr Trp Gly Asp
                325                 330                 335
Lys Glu Leu Glu Asp Pro Val Leu Phe Ser Arg Leu Thr Val Gly Glu
                340                 345                 350
Leu Pro Ser Ala Ser Glu Gly Thr Leu Gly Leu Phe Asn Ser Gly Thr
                355                 360                 365
Tyr Leu Phe Pro Thr Gln Ile Gly Tyr Gly Glu Asn Ala Thr Val Asn
                370                 375                 380
Asp Tyr Met Leu Thr Pro Gly Asn Asp Phe Ile Ile Pro Thr Arg Phe
385                 390                 395                 400
Asn Thr Ile Arg Asn Asp Val Tyr Leu Thr Met Arg Ser Arg Ala Tyr
                405                 410                 415
Phe Gly Ala Gly Leu Gln Gly Ala Gln Ala Ser Leu Thr Ala Thr Ser
                420                 425                 430
Asn Gly Lys Pro Val Val Gly Ser Ser Glu Asn Ser Lys Phe Tyr Ile
                435                 440                 445
Asp Thr Asp Ser Asn Val Tyr Leu Thr Lys Gln Gly Phe Asp Gln Leu
                450                 455                 460
Gly Asn Phe Gly Lys Ile Met Ala Pro Phe Val Tyr Thr Ser Ala Ser
465                 470                 475                 480
Asn Asp Leu Lys Lys Val Gly Ile Asp Lys Phe Ser Ala Met Met Asn
                485                 490                 495
Gln Gly Leu Ser Ser Ile Gln Ser Lys Ser Gly Ala Asn Thr Ile Val
                500                 505                 510
Ser Gly Asn Gly Gly Gln Ile Gln Leu Ser Gly Phe Asn Arg Glu Thr
                515                 520                 525
```

```
Asp Leu Asp Gly Ala Phe Ser Ser Ile Ser Asp Arg Glu Asn Asp
    530                 535                 540
Ala Leu Lys Asn Thr Asp Val Asn Phe Tyr Met Tyr Thr Lys Gly Asn
545                 550                 555                 560
Thr Glu Thr Asn Val Thr Thr Pro Leu Ala Pro Asn Gly Tyr His Leu
                565                 570                 575
Tyr Ser Pro Asn Val Ser Glu Phe Lys Ile Gln Thr Thr Arg Pro Tyr
                580                 585                 590
Phe Ser Trp Thr Gly Asp Ile Ser Asn Ala Ile Lys Ile Ser Glu Ala
            595                 600                 605
Asn Ala Asp Phe Asp Asp Leu Leu Gly Ser Asn Ser Leu Gln Val Thr
    610                 615                 620
Asp Asn Gly Val Asp Ser Asp Gly Thr Pro Ile Ser Val Asp Leu Asn
625                 630                 635                 640
Arg Val Arg Ile Arg Ile Ser Glu Asp Gly Gly Ser Thr Tyr Ser Asn
                645                 650                 655
Asp Ser Tyr Thr Leu Asn Asp Leu Lys Ala Leu Leu Thr Ser Gly Asn
            660                 665                 670
Ile Thr Val Pro Lys Ile Val Ile Ala Tyr Thr Tyr Ser Ala Thr Asp
    675                 680                 685
Ser Lys Thr Asp Asn Ile Gly Lys Leu Pro Ser Glu Ile Asp Asp Asn
    690                 695                 700
Thr Gly Ala Tyr Ala Val Pro Phe Thr Arg Thr Leu Thr Asn Asp Ile
705                 710                 715                 720
Pro Asp Lys Lys Ser Asn Ile Thr Val Lys Tyr Ile Asp Ile Ser Gly
                725                 730                 735
Asn Thr Ile Ser Asp Asn Ile Val Lys Ala Gly Asn Val Gly Asp Ser
            740                 745                 750
Tyr Thr Thr Glu Gln Lys Ala Ile Pro Gly Tyr Thr Phe Lys Ala Val
    755                 760                 765
Gln Gly Asn Pro Thr Gly Gln Phe Thr Ser Asp Ala Gln Thr Val Thr
770                 775                 780
Tyr Val Tyr Thr Lys Asp Pro Val Ala Gly Gly Ser Val Thr Ala Lys
785                 790                 795                 800
Tyr Val Asp Thr Ser Gly Asn Ala Ile Ser Asp Asn Val Val Lys Thr
                805                 810                 815
Gly Asn Ile Gly Asp Thr Tyr Ser Thr Lys Gln Lys Thr Ile Pro Gly
            820                 825                 830
Tyr Thr Phe Lys Glu Val Gln Gly Ser Val Ser Gly Gln Phe Thr Asn
    835                 840                 845
Gln Glu Gln Thr Val Thr Tyr Val Tyr Thr Lys Asp Pro Val Ala Gly
850                 855                 860
Ala His Ile Ile Ala Lys Tyr Val Asp Glu Asn Gly Asn Thr Ile Ser
865                 870                 875                 880
Asp Asn Val Val Lys Ser Gly Asn Ile Gly Asp Ser Tyr Thr Thr Glu
                885                 890                 895
Gln Lys Ala Ile Pro Gly Tyr Thr Phe Lys Ala Val Gln Gly Asn Pro
            900                 905                 910
Thr Gly Gln Phe Thr Ser Asp Ala Gln Thr Val Thr Tyr Ile Tyr Thr
    915                 920                 925
Lys Val Lys Thr Ser Gly Gly Ser Glu Thr Pro Thr Pro Ser Lys Thr
930                 935                 940
```

```
Ile Ala Thr Lys Ser Ser Thr Asn Thr Ile Ser Ser Thr Leu Pro
945                 950                 955                 960

Lys Thr Gly Asp Ser Gln Val Ser Thr Leu Phe Gly Met Val Val Gly
                965                 970                 975

Phe Phe Ile Phe Gly Ala Gly Thr Leu Ser Leu Phe Phe Asn Ser Lys
                980                 985                 990

Arg Lys Arg Lys Ser Lys
        995
```

<210> SEQ ID NO 17
<211> LENGTH: 3240
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (208)..(3201)
<223> OTHER INFORMATION: CDS

<400> SEQUENCE: 17

| | | | | | |
|---|---|---|---|---|---|
| agctttagaa | gaagaaaaag | cagctgttga | attagagggt | tcagaaactg | cctgatggat | 60 |
| attttttata | aatctggttt | gaacaaatta | tattgacatc | tcttttcta | tcctgataat | 120 |
| tctgagaggt | tattttggga | aatactattg | aaccatatcg | aggtggtgtg | gtataatgaa | 180 |
| gggaattaaa | aaagatagga | aaatttcatg | gtgtcaaaga | ataacgtgca | gttttacgac | 240 |
| aagaaaaatg | ataatcaaca | gcgatggggc | ttgagaaaaa | cttcatttgg | tttagcgagc | 300 |
| cttttgcttg | gcacgtcttt | cgtttattc | aatggagcgg | tcgtgcacgc | ggatacaccg | 360 |
| agcaatgaca | aacctgtggt | tgtaacaacc | attgcgtcaa | actcatctgc | cgttgaagct | 420 |
| gagactgcca | gcagttcttc | atcaagtgcc | gtaaaagcgg | aaacgaccag | cgcctcttct | 480 |
| tcaagtgctg | taaaagctga | gacagcctct | agcagttcaa | gctcagccgt | aaaggcagaa | 540 |
| actacgagtg | catcatcttc | atcagcggta | aaggcggaga | ccgctagctc | ttcttctagt | 600 |
| agtgctgtga | aagccgagac | gacgagcgca | tcttcatctt | ctgctgttaa | ggcggaaaca | 660 |
| acaagcgctt | ctagctcaag | cgccgtcaaa | gcagaaacag | cgagttcatc | ttctagtagt | 720 |
| gcagttaaag | ccgaaactac | ctctgccagc | tcatcttcag | cagcaaaggc | ggataccacc | 780 |
| agcgcagcta | gttcatctgc | ggcaaagagc | gacagttcac | ttgtgaaagg | gcgtgtttat | 840 |
| gcctctacgt | atttagagtc | aaacaagaac | tattataccg | atccggctat | cagtcgtggc | 900 |
| ttttagaca | gtccgatatc | taaagagtta | cttggtgatc | aaaattggaa | tatgtttcaa | 960 |
| gttgctgtca | gcaagaacct | tgtctcatat | aatccaggaa | tgacgtttaa | ccaatattac | 1020 |
| ttggcgaata | atatctcacc | agaagataat | ttcatcgttt | atcctcgttt | aaccaatcaa | 1080 |
| atagtaagat | taaagagtgg | agcctatttg | aacgcgaacc | ctaaccctaa | ggggcgaaa | 1140 |
| gacgatagtg | gcaacatagt | cgactacata | acttatgttg | gccctacgga | cgatcgtggt | 1200 |
| gcgtactggg | gggacaaaga | gcttgaagat | ccggtgcttt | tctctcgact | tactgtgggt | 1260 |
| gagttgccga | gtgcttctga | gggcacgctt | ggcttgttta | acagtggaac | atatcttttc | 1320 |
| cctacacaaa | taggctacgg | tgaaaacgcc | acagttaacg | attacatgct | taccctggt | 1380 |
| aatgacttca | tcataccaac | tcgatttaat | acgatccgta | atgacgtgta | cttaacgatg | 1440 |
| cgatctcgtg | catacttcgg | ggctggatta | caaggggcac | aggcaagttt | aaccgcaacc | 1500 |
| tctaatggaa | aaccggtagt | ggggtcatca | gagaacagca | aattttacat | agacacagac | 1560 |

| | |
|---|---|
| agtaatgtct atcttacaaa acaggggttt gatcaacttg gtaactttgg taaaataatg | 1620 |
| gctccattcg tttatacgag cgcttcaaac gatttgaaga aggtcggaat agacaaattc | 1680 |
| tcagccatga tgaaccaagg gttgagtagc atacaaagca agtctggggc aaacaccatc | 1740 |
| gtatcaggga acggcggcca gattcaattg agcggtttca atagagaaac agacttggat | 1800 |
| ggagcattct catcttcaat aagcgatcgt gagaacgatg cattaaagaa tacagatgtc | 1860 |
| aacttctata tgtatacgaa aggcaacaca gaaactaatg tgacgacgcc gttggccccg | 1920 |
| aatgggtacc acctttactc accaaacgta tctgaattca agatacagac taccagacct | 1980 |
| tacttctcat ggacgggaga cataagtaat gctataaaaa tttctgaagc caatgcggat | 2040 |
| ttcgatgatt tacttggtag taactcatta caggttactg ataatggggt ggacagcgac | 2100 |
| ggtacccta tatctgtcga ccttaatcgt gtcagaataa gaatatctga ggacggaggg | 2160 |
| agtacatatt ctaacgattc ttatacgctt aatgacttaa aagccttatt gaccagcgga | 2220 |
| aacatcactg tccctaagat agttatcgct tatacctact ctgcgactga ttcaaaaact | 2280 |
| gataacatcg gtaagttacc gtctgaaatt gacgacaaca caggcgcgta cgccgttccg | 2340 |
| ttcacacgta cgttgacgaa tgacattcca gataaaaaaa gtaacattac ggtcaagtat | 2400 |
| atcgatatct ctggtaatac catatctgat aacatagtta aagccggtaa tgttggcgat | 2460 |
| tcatatacaa cagaacaaaa agcaataccg ggatacacct tcaaagccgt acaaggtaat | 2520 |
| ccaaccggtc aattcacgtc tgatgctcaa acagtgacgt acgtttacac gaaggatcca | 2580 |
| gtggcaggcg gcagcgtcac cgctaagtat gtcgatacca gtgggaacgc catctctgat | 2640 |
| aacgttgtta aaaccggtaa catcggcgat acctacagta ctaagcagaa gaccataccg | 2700 |
| ggatatactt tcaaagaggt tcaaggatct gttagcggac aatttaccaa tcaggaacaa | 2760 |
| acggtcactt atgtatacac taaagatccg gtcgctggtg cccatatcat agcaaaatac | 2820 |
| gtagacgaga atggtaacac gatatcagac aacgttgtga agtcaggtaa cattggggat | 2880 |
| tcttacacta ctgagcaaaa ggcaattcct ggatacactt ttaaagctgt tcagggaaac | 2940 |
| ccaacgggac aattcaccag tgacgcccag acggtgacct acatatacac taaagtgaaa | 3000 |
| acatctggtg ggagcgaaac cccaacgccg tcaaaaacga ttgcaaccaa gtcaagtaca | 3060 |
| aacacaatct ctagttctac acttccgaag acgggcgata gtcaagtgtc tactttattc | 3120 |
| ggcatggtgg tggggttctt catatttggg gcgggaacct tgagcttatt ttttaacagt | 3180 |
| aagcgaaaaa gaaagtcaaa gtaaattaat ctataagtta ctgacaaaac tgtcagtaac | 3240 |

<210> SEQ ID NO 18
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Lys Lys Lys Ile Ile Ser Ala Ile Leu Met Ser Thr Val Ile Leu
1               5                   10                  15

Ser Ala Ala Pro Leu Ser Gly Val Tyr Ala Ser Ser Ala Val Asn
            20                  25                  30

Ser Glu Leu Val His Lys Gly Glu Leu Thr Ile Gly Leu Glu Gly Thr
        35                  40                  45

Tyr Ser Pro Tyr Ser Tyr Arg Lys Asn Asn Lys Leu Thr Gly Phe Glu
    50                  55                  60

Val Asp Leu Gly Lys Ala Val Ala Lys Lys Met Gly Leu Lys Ala Asn
 65                  70                  75                  80

Phe Val Pro Thr Lys Trp Asp Ser Leu Ile Ala Gly Leu Gly Ser Gly
                 85                  90                  95

Lys Phe Asp Val Val Met Asn Asn Ile Thr Gln Thr Pro Glu Arg Ala
            100                 105                 110

Lys Gln Tyr Asn Phe Ser Thr Pro Tyr Ile Lys Ser Arg Phe Ala Leu
        115                 120                 125

Ile Val Pro Thr Asp Ser Asn Ile Lys Ser Leu Lys Asn Ile Lys Gly
    130                 135                 140

Lys Lys Ile Ile Ala Gly Thr Gly Thr Asn Asn Ala Asn Val Val Lys
145                 150                 155                 160

Lys Tyr Lys Gly Asn Leu Thr Pro Asn Gly Asp Phe Ala Ser Ser Leu
                165                 170                 175

Asp Met Ile Lys Gln Gly Arg Ala Ala Gly Thr Ile Asn Ser Arg Glu
            180                 185                 190

Ala Trp Tyr Ala Tyr Ser Lys Lys Asn Ser Thr Lys Gly Leu Lys Met
        195                 200                 205

Ile Asp Val Ser Ser Glu Gln Asp Pro Ala Lys Ile Ser Ala Leu Phe
    210                 215                 220

Asn Lys Lys Asp Thr Ala Ile Gln Ser Ser Tyr Asn Lys Ala Leu Lys
225                 230                 235                 240

Glu Leu Gln Gln Asp Gly Thr Val Lys Lys Leu Ser Glu Lys Tyr Phe
                245                 250                 255

Gly Ala Asp Ile Thr Glu
            260

<210> SEQ ID NO 19
<211> LENGTH: 957
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (153)..(938)
<223> OTHER INFORMATION: CDS

<400> SEQUENCE: 19
tggatatttt ttataaatct ggtttgaaca aattatattg acatctcttt ttctatcctg     60
ataattctga gaggttattt tgggaaatac tattgaacca tatcgaggtg gtgtggtata    120
atgaagggaa ttaaaaaaga taggaaaatt tcatgaaaaa aaagattatc tcagctatt t    180 taatgtctac agtgatactt tctgctgcag ccccgttgtc aggtgtttac gcttcatcag    240
ctgttaattc agaattagtt cataagggag aattaacaat tggtcttgag ggaacgtact    300
ctccgtactc ttatcgtaaa ataacaaat taactggctt tgaagtagat cttggtaaag    360
cagttgctaa aaagatgggc ttaaaagcta actttgtacc aactaaatgg gattcgctaa    420
ttgccggtct tggttcaggt aagtttgatg tagtaatgaa caacattaca cagacacctg    480
aacgggccaa gcaatataat ttctctaccc catatatcaa gtcccggttt gcattaattg    540
ttcctactga tagtaacatc aaaagcttga agaatattaa aggcaagaag attattgctg    600
gtacgggaac taataatgcg aatgtggtaa aaaaatataa gggtaacctt acaccaaatg    660
gcgattttgc tagttcctta gatatgatca agcaaggtcg ggctgccggg acaattaact    720
cccgtgaagc ttggtacgct tacagcaaga agaacagtac taagggtctc aagatgattg    780

```
atgtttctag tgaacaagat ccagctaaga tttcagcact ttttaacaag aaagatactg      840
ctattcaatc ttcctacaac aaggcactta aggaacttca acaagacgga acagtcaaga      900
agctatctga aaagtacttc ggtgcagata ttactgaata aattaatcta taagtta        957
```

```
<210> SEQ ID NO 20
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20
```

Met Lys Phe Trp Lys Lys Ala Leu Leu Thr Ile Val Ala Leu Thr Val
1               5                   10                  15

Gly Thr Pro Ala Gly Ile Thr Ser Val Ser Ala Ala Ser Ser Ala Val
            20                  25                  30

Asn Ser Glu Leu Val His Lys Gly Glu Leu Thr Ile Gly Leu Glu Gly
        35                  40                  45

Thr Tyr Ser Pro Tyr Ser Tyr Arg Lys Asn Asn Lys Leu Thr Gly Phe
    50                  55                  60

Glu Val Asp Leu Gly Lys Ala Val Ala Lys Lys Met Gly Leu Lys Ala
65                  70                  75                  80

Asn Phe Val Pro Thr Lys Trp Asp Ser Leu Ile Ala Gly Leu Gly Ser
                85                  90                  95

Gly Lys Phe Asp Val Val Met Asn Asn Ile Thr Gln Thr Pro Glu Arg
            100                 105                 110

Ala Lys Gln Tyr Asn Phe Ser Thr Pro Tyr Ile Lys Ser Arg Phe Ala
        115                 120                 125

Leu Ile Val Pro Thr Asp Ser Asn Ile Lys Ser Leu Lys Asn Ile Lys
    130                 135                 140

Gly Lys Lys Ile Ile Ala Gly Thr Gly Thr Asn Asn Ala Asn Val Val
145                 150                 155                 160

Lys Lys Tyr Lys Gly Asn Leu Thr Pro Asn Gly Asp Phe Ala Ser Ser
                165                 170                 175

Leu Asp Met Ile Lys Gln Gly Arg Ala Ala Gly Thr Ile Asn Ser Arg
            180                 185                 190

Glu Ala Trp Tyr Ala Tyr Ser Lys Asn Ser Thr Lys Gly Leu Lys
        195                 200                 205

Met Ile Asp Val Ser Ser Glu Gln Asp Pro Ala Lys Ile Ser Ala Leu
    210                 215                 220

Phe Asn Lys Lys Asp Thr Ala Ile Gln Ser Ser Tyr Asn Lys Ala Leu
225                 230                 235                 240

Lys Glu Leu Gln Gln Asp Gly Thr Val Lys Lys Leu Ser Glu Lys Tyr
                245                 250                 255

Phe Gly Ala Asp Ile Thr Glu
            260

```
<210> SEQ ID NO 21
<211> LENGTH: 960
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
```

```
<222> LOCATION: (153)..(941)
<223> OTHER INFORMATION: CDS

<400> SEQUENCE: 21
tggatatttt ttataaatct ggtttgaaca aattatattg acatctcttt ttctatcctg    60
ataattctga gaggttattt tgggaaatac tattgaacca tatcgaggtg gtgtggtata   120
atgaagggaa ttaaaaaaga taggaaaatt tcatgaaatt ttggaagaaa gcactattaa   180
caattgtagc cttaacggtc ggtaccccctg caggaatcac aagtgtttct gctgcttcat   240
cagctgttaa ttcagaatta gttcataagg gagaattaac aattggtctt gagggaacgt   300
actctccgta ctcttatcgt aaaaataaca aattaactgg ctttgaagta gatcttggta   360
aagcagttgc taaaaagatg ggcttaaaag ctaactttgt accaactaaa tgggattcgc   420
taattgccgg tcttggttca ggtaagtttg atgtagtaat gaacaacatt acacagacac   480
ctgaacgggc caagcaatat aatttctcta ccccatatat caagtcccgg tttgcattaa   540
ttgttcctac tgatagtaac atcaaaagct tgaagaatat taaaggcaag aagattattg   600
ctggtacggg aactaataat gcgaatgtgg taaaaaaata aagggtaac cttacaccaa   660
atggcgattt tgctagttcc ttagatatga tcaagcaagg tcgggctgcc gggacaatta   720
actcccgtga agcttggtac gcttacagca agaagaacag tactaagggt ctcaagatga   780
ttgatgtttc tagtgaacaa gatccagcta agatttcagc acttttttaac aagaaagata   840
ctgctattca atcttcctac aacaaggcac ttaaggaact tcaacaagac ggaacagtca   900
agaagctatc tgaaaagtac ttcggtgcag atattactga ataaattaat ctataagtta   960
```

```
<210> SEQ ID NO 22
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22
```

Met Lys Lys Ile Ile Ser Ala Ile Leu Met Ser Thr Val Ile Leu
1               5                   10                  15

Ser Ala Ala Pro Leu Ser Gly Val Tyr Ala Glu Ala Gln Thr Glu
                20                  25                  30

Thr Cys Thr Val Ala Pro Arg Glu Arg Gln Asn Cys Gly Phe Pro Gly
                35                  40                  45

Val Thr Pro Ser Gln Cys Ala Asn Lys Gly Cys Cys Phe Asp Asp Thr
50                  55                  60

Val Arg Gly Val Pro Trp Cys Phe Tyr Pro Asn Thr Ile Asp Val Pro
65                  70                  75                  80

Pro Glu Glu Glu Cys Glu Phe Asp Pro Lys Glu Glu Asp Asn Asn Lys
                85                  90                  95

Pro Gly Lys Glu Asp Gly Asn Lys Pro Gly Lys Glu Asp Gly Asn Lys
                100                 105                 110

Pro Gly Lys Glu Asp Asn Lys Lys Pro Gly Lys Glu Asp Gly Asn Lys
            115                 120                 125

Pro Gly Lys Glu Asp Asn Lys Lys Pro Gly Lys Glu Asp Gly Asn Lys
                130                 135                 140

Pro Gly Lys Glu Asp Gly Asn Lys Pro Gly Lys Glu Asp Gly Asn Lys
145                 150                 155                 160

Pro Gly Lys Glu Asp Gly Asn Lys Pro Gly Lys Glu Asp Gly Asn Gly

```
                    165                 170                 175
Val His Val Val Lys Pro Gly Asp Thr Val Asn Asp Ile Ala Lys Ala
            180                 185                 190

Asn Gly Thr Thr Ala Asp Lys Ile Ala Ala Asp Asn Lys Leu Ala Asp
        195                 200                 205

Lys Asn Met Ile Lys Pro Gly Gln Glu Leu Val Val Asp Lys Lys Gln
    210                 215                 220

Pro Ala Asn His Ala Asp Ala Asn Lys Ala Gln Ala Leu Pro Glu Thr
225                 230                 235                 240

Gly Glu Glu Asn Pro Phe Ile Gly Thr Thr Val Phe Gly Gly Leu Ser
                245                 250                 255

Leu Ala Leu Gly Ala Ala Leu Leu Ala Gly Arg Arg Arg Glu Leu
            260                 265                 270

<210> SEQ ID NO 23
<211> LENGTH: 1020
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (153)..(965)
<223> OTHER INFORMATION: CDS

<400> SEQUENCE: 23
tggatatttt ttataaatct ggtttgaaca aattatattg acatctcttt ttctatcctg      60
ataattctga gaggttattt tgggaaatac tattgaacca tatcgaggtg gtgtggtata    120
atgaagggaa ttaaaaaaga taggaaaatt tcatgaaaaa aaagattatc tcagctattt    180
taatgtctac agtgatactt tctgctgcag ccccgttgtc aggtgtttac gccgaagctc    240
aaactgaaac ttgtactgtt gctccacgtg aacgtcaaaa ctgtggtttt ccaggtgtta    300
ctccatcaca atgtgctaac aaaggttgtt gttttgatga tactgttcgt ggtgttccat    360
ggtgttttta cccaaacact atcgatgttc caccagaaga agaatgtgaa tttgatccaa    420
aagaggaaga caacaacaag cctggtaaag aagacggcaa caaacctggt aaagaagacg    480
gcaacaaacc tggtaaagaa gacaacaaaa acctggcaa agaagacggc aacaaacctg    540
gtaaagaaga caacaaaaaa cctggcaaag aagatgcaa caaacctggt aaagaagacg    600
gcaacaagcc tggtaaagaa gatggcaaca gcctggtaa agaagatggc aacaagcctg    660
gtaaagaaga cggcaacgga gtacatgtcg ttaaacctgg tgatacagta atgacattg    720 caaaagcaaa cggcactact gctgacaaaa ttgctgcaga taacaaatta gctgataaaa    780
acatgatcaa acctggtcaa gaacttgttg ttgataagaa gcaaccagca aaccatgcag    840
atgctaacaa agctcaagca ttaccagaaa ctggtgaaga aaatccattc atcggtacaa    900
ctgtatttgg tggattatca ttagcgttag gtgcagcgtt attagctgga cgtcgtcgcg    960
aactataaaa ttaatctata agttactgac aaaactgtca gtaactttt tgtgggaaa    1020

<210> SEQ ID NO 24
<211> LENGTH: 716
<212> TYPE: PRT
<213> ORGANISM: Petroselinum crispum

<400> SEQUENCE: 24

Met Glu Asn Gly Asn Gly Ala Thr Thr Asn Gly His Val Asn Gly Asn
1               5                   10                  15
```

```
Gly Met Asp Phe Cys Met Lys Thr Glu Asp Pro Leu Tyr Trp Gly Ile
             20                  25                  30

Ala Ala Glu Ala Met Thr Gly Ser His Leu Asp Glu Val Lys Lys Met
         35                  40                  45

Val Ala Glu Tyr Arg Lys Pro Val Val Lys Leu Gly Gly Thr Leu
 50                  55                  60

Thr Ile Ser Gln Val Ala Ala Ile Ser Ala Arg Asp Gly Ser Gly Val
 65                  70                  75                  80

Thr Val Glu Leu Ser Glu Ala Ala Arg Ala Gly Val Lys Ala Ser Ser
                 85                  90                  95

Asp Trp Val Met Asp Ser Met Asn Lys Gly Thr Asp Ser Tyr Gly Val
             100                 105                 110

Thr Thr Gly Phe Gly Ala Thr Ser His Arg Arg Thr Lys Gln Gly Gly
             115                 120                 125

Ala Leu Gln Lys Glu Leu Ile Arg Phe Leu Asn Ala Gly Ile Phe Gly
130                 135                 140

Asn Gly Ser Asp Asn Thr Leu Pro His Ser Ala Thr Arg Ala Ala Met
145                 150                 155                 160

Leu Val Arg Ile Asn Thr Leu Leu Gln Gly Tyr Ser Gly Ile Arg Phe
                 165                 170                 175

Glu Ile Leu Glu Ala Ile Thr Lys Phe Leu Asn Gln Asn Ile Thr Pro
             180                 185                 190

Cys Leu Pro Leu Arg Gly Thr Ile Thr Ala Ser Gly Asp Leu Val Pro
             195                 200                 205

Leu Ser Tyr Ile Ala Gly Leu Leu Thr Gly Arg Pro Asn Ser Lys Ala
         210                 215                 220

Val Gly Pro Thr Gly Val Ile Leu Ser Pro Glu Glu Ala Phe Lys Leu
225                 230                 235                 240

Ala Gly Val Glu Gly Gly Phe Phe Glu Leu Gln Pro Lys Glu Gly Leu
                 245                 250                 255

Ala Leu Val Asn Gly Thr Ala Val Gly Ser Gly Met Ala Ser Met Val
             260                 265                 270

Leu Phe Glu Ala Asn Ile Leu Ala Val Leu Ala Glu Val Met Ser Ala
         275                 280                 285

Ile Phe Ala Glu Val Met Gln Gly Lys Pro Glu Phe Thr Asp His Leu
         290                 295                 300

Thr His Lys Leu Lys His His Pro Gly Gln Ile Glu Ala Ala Ala Ile
305                 310                 315                 320

Met Glu His Ile Leu Asp Gly Ser Ala Tyr Val Lys Ala Ala Gln Lys
                 325                 330                 335

Leu His Glu Met Asp Pro Leu Gln Lys Pro Lys Gln Asp Arg Tyr Ala
             340                 345                 350

Leu Arg Thr Ser Pro Gln Trp Leu Gly Pro Gln Ile Glu Val Ile Arg
             355                 360                 365

Ser Ser Thr Lys Met Ile Glu Arg Glu Ile Asn Ser Val Asn Asp Asn
         370                 375                 380

Pro Leu Ile Asp Val Ser Arg Asn Lys Ala Ile His Gly Gly Asn Phe
385                 390                 395                 400

Gln Gly Thr Pro Ile Gly Val Ser Met Asp Asn Thr Arg Leu Ala Ile
             405                 410                 415

Ala Ala Ile Gly Lys Leu Met Phe Ala Gln Phe Ser Glu Leu Val Asn
             420                 425                 430
```

```
Asp Phe Tyr Asn Asn Gly Leu Pro Ser Asn Leu Ser Gly Gly Arg Asn
            435                 440                 445

Pro Ser Leu Asp Tyr Gly Phe Lys Gly Ala Glu Ile Ala Met Ala Ser
    450                 455                 460

Tyr Cys Ser Glu Leu Gln Phe Leu Ala Asn Pro Val Thr Asn His Val
465                 470                 475                 480

Gln Ser Ala Glu Gln His Asn Gln Asp Val Asn Ser Leu Gly Leu Ile
                485                 490                 495

Ser Ser Arg Lys Thr Ser Glu Ala Val Glu Ile Leu Lys Leu Met Ser
            500                 505                 510

Thr Thr Phe Leu Val Gly Leu Cys Gln Ala Ile Asp Leu Arg His Leu
            515                 520                 525

Glu Glu Asn Leu Lys Ser Thr Val Lys Asn Thr Val Ser Ser Val Ala
    530                 535                 540

Lys Arg Val Leu Thr Met Gly Val Asn Gly Glu Leu His Pro Ser Arg
545                 550                 555                 560

Phe Cys Glu Lys Asp Leu Leu Arg Val Val Asp Arg Glu Tyr Ile Phe
                565                 570                 575

Ala Tyr Ile Asp Asp Pro Cys Ser Ala Thr Tyr Pro Leu Met Gln Lys
            580                 585                 590

Leu Arg Gln Thr Leu Val Glu His Ala Leu Lys Asn Gly Asp Asn Glu
        595                 600                 605

Arg Asn Leu Ser Thr Ser Ile Phe Gln Lys Ile Ala Thr Phe Glu Asp
    610                 615                 620

Glu Leu Lys Ala Leu Leu Pro Lys Glu Val Glu Ser Ala Arg Ala Ala
625                 630                 635                 640

Leu Glu Ser Gly Asn Pro Ala Ile Pro Asn Arg Ile Glu Glu Cys Arg
                645                 650                 655

Ser Tyr Pro Leu Tyr Lys Phe Val Arg Lys Glu Leu Gly Thr Glu Tyr
            660                 665                 670

Leu Thr Gly Glu Lys Val Thr Ser Pro Gly Glu Glu Phe Glu Lys Val
        675                 680                 685

Phe Ile Ala Met Ser Lys Gly Glu Ile Ile Asp Pro Leu Leu Glu Cys
    690                 695                 700

Leu Glu Ser Trp Asn Gly Ala Pro Leu Pro Ile Cys
705                 710                 715

<210> SEQ ID NO 25
<211> LENGTH: 3300
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1091)..(3238)
<223> OTHER INFORMATION: CDS
<220> FEATURE:
<221> NAME/KEY: misc_feature
<222> LOCATION: (1091)..(3241)
<223> OTHER INFORMATION: PAL
<220> FEATURE:
<221> NAME/KEY: misc_feature
<222> LOCATION: (3239)..(3241)
<223> OTHER INFORMATION: Stop codon

<400> SEQUENCE: 25
ttgttaactt agtcaattta aaaggtttgc cttttataaa atctaatccc tataaggagg      60
```

| | |
|---|---|
| aaactactaa tggtagttaa agttggtatt aacggtttcg gtcgtatcgg tcgtcttgct | 120 |
| ttccgtcgta ttcaaaatgt tgaaggtgtt gaagttgttg caatcaacga cttgacagat | 180 |
| ccagcaatgc ttgctcactt gcttaaatac gatacaactc aaggtcgttt tgatggtaaa | 240 |
| gttgaagtta aagatggtgg ttttgaagtt aacggtaaat tcgttaaagt tactgctgaa | 300 |
| tctaacccag ctaacatcaa ctgggctgaa gttggtgcag aaatcgttct tgaagcaact | 360 |
| ggtttcttcg caactaaaga aaaagctgaa caacacttgc acgctaatgg tgctaagaaa | 420 |
| gttgttatca ctgcacctgg tggatcagat gttaaaacaa tcgttttcaa cactaaccac | 480 |
| gaagtacttg atggaactga acagtaatt tcagctggtt catgtacaac caactgtctt | 540 |
| gctccaatgg ctgatacttt gaacaaacaa ttcggtatca aagttggtac aatgactaca | 600 |
| gttcacggtt acactggtga ccaaatgact cttgatggcc cacaccgtgg tggagatttc | 660 |
| cgtcgcgcac gtgctgcagc tgaaaacatc gtacctaact caacaggtgc tgctaaagcc | 720 |
| atcggtcttg tattgccaga acttcaaggt aaacttcaag gacatgctca acgtgtacca | 780 |
| gttccaactg gttcattgac tgaacttgtt actatccttg ataaagaagt tacagttgac | 840 |
| gaaatcaacg cagctatgaa agctgcttca aatgaatcat ttggttacaa cgaagaccaa | 900 |
| atcgtttcat ctgatatcgt tggtatctca aactcttcac tctttgatgc tactcaaact | 960 |
| gaagttactt cagctaacgg agctcaactt gttaaaactg tatcttggta cgataacgaa | 1020 |
| atgtcataca cttcaaacct tgttcgtaca cttgcatact tcgctaaaat cgctaaataa | 1080 |
| ggaggaaaaa atggaaaatg gtaatggtgc aactacgaat gggcatgtga acgggaatgg | 1140 |
| aatggacttc tgtatgaaga cagaagatcc tctttattgg ggtattgcag ctgaagcgat | 1200 |
| gactggttca cacttggatg aagtaaaaaa aatggtcgcc gagtacagaa aacctgtcgt | 1260 |
| taaattagga ggagagacac ttacaattag tcaggttgct gctattagtg cgcgagatgg | 1320 |
| aagtggtgta actgtggaac ttagtgaggc agcacgcgct ggagttaaag cttcttctga | 1380 |
| ttgggtaatg gacagtatga ataaaggaac tgattcatac ggtgtaacaa ctggtttcgg | 1440 |
| cgctacttct catcgtcgta cgaaacaggg aggagctctt caaaaagaac ttattagatt | 1500 |
| tcttaacgca ggaattttcg gtaatggctc agataatact cttccacatt ctgcaacacg | 1560 |
| agctgcaatg cttgtcagaa ttaatacttt acttcaagga tactcaggca ttcgttttga | 1620 |
| aatacttgaa gcaattacaa aatttttgaa ccaaaatatt actccttgct taccacttcg | 1680 |
| tggaacaatt acagcttcag gtgatttagt tccattatct tacattgctg gtcttcttac | 1740 |
| tggtcgacct aatagtaaag ctgtaggtcc tacgggggtt attttatctc cagaagaggc | 1800 |
| attcaagtta gctggtgttg aaggtgggtt tttcgaattg caaccaaagg aaggacttgc | 1860 |
| attggtgaat ggcacagctg ttggctctgg aatggctagt atggttttat ttgaagctaa | 1920 |
| tattcttgcg gtattagctg aagtaatgtc tgcaattttt gccgaagtca tgcaaggaaa | 1980 |
| accagaattt actgatcatt taactcacaa attgaaacac catcctggac aaatcgaagc | 2040 |
| agctgcaatt atggaacata tattagatgg gtcagcttat gttaaagctg ctcagaaact | 2100 |
| tcacgaaatg gatcctttac aaaaacctaa gcaagatcgt tatgctctta gaacgagtcc | 2160 |
| acaatggttg gggccacaaa ttgaggttat tcgctcatca actaaaatga ttgaaagaga | 2220 |
| aatcaattca gttaatgaca atcctttaat tgatgtttca cgtaataaag cgattcatgg | 2280 |
| tggtaacttc caaggaacac caatcggtgt ttcaatggat aatactagat tagctattgc | 2340 |
| ggctattgga aaacttatgt ttgcacaatt ttctgaactt gttaacgatt tctataacaa | 2400 |
| cggattacca tcaaatttaa gtggcgggcg caatccaagt ttggattatg gttttaaagg | 2460 |

```
tgctgaaatt gccatggcat cttattgttc agaacttcaa tttttagcca atccagttac    2520
aaaccacgta caaagtgcgg aacaacataa tcaagatgtc aactctttgg gccttatttc    2580
ttcacgaaaa acaagtgagg ccgtcgagat attaaaatta atgtcaacaa catttcttgt    2640
cggcctttgc caagcaattg atttacgtca tcttgaagaa aatttaaaat caactgttaa    2700
aaacacagta tcttctgttg ctaaacgagt tttaaccatg ggagttaatg gtgaattaca    2760
tccatcacgc ttttgtgaaa aagatctttt acgcgtcgtc gatcgtgaat atattttgc     2820 atatattgat gacccatgta gtgcaacata tcctttaatg cagaaactta gacaaacatt    2880
agttgagcat gccttgaaga atggtgataa tgagcgtaat ctttctacat caatttttca    2940
aaaaattgca accttcgagg acgaacttaa agcattatta cctaaagaag tggaatcagc    3000
tagagccgct ttggaaagtg gaaacccagc cattccaaat cgaattgaag aatgtcgttc    3060
atatcctctt tataaatttg ttcgaaaaga gcttggtacg gaatatctta ctggcgaaaa    3120
ggtaacatca cctggtgaag agtttgaaaa agttttatt gccatgagta aaggtgaaat     3180
tattgatcct ttacttgaat gtcttgagtc atggaatgga gccccttac ctatctgtta     3240 attttccgat tttaacggta taaaaaccag tcttcgggct ggttttttta ttttataaag    3300
```